(12) United States Patent
Alailima et al.

(10) Patent No.: US 11,839,472 B2
(45) Date of Patent: Dec. 12, 2023

(54) PLATFORMS TO IMPLEMENT SIGNAL DETECTION METRICS IN ADAPTIVE RESPONSE-DEADLINE PROCEDURES

(71) Applicant: Akili Interactive Labs, Inc., Boston, MA (US)

(72) Inventors: Titiimaea Alailima, Cambridge, MA (US); Jeffrey Bower, Norwood, MA (US); Matthew Omernick, Larkspur, CA (US); Walter Edward Martucci, Westwood, MA (US); Adam Piper, Sebastopol, CA (US); Paul Rand Pierce, Seattle, WA (US); Ashley Mateus, Cambridge, MA (US); Scott Kellogg, Mattapoisett, MA (US)

(73) Assignee: Akili Interactive Labs, Inc., Boston, MA (US)

( * ) Notice: Subject to any disclaimer, the term of this patent is extended or adjusted under 35 U.S.C. 154(b) by 1089 days.

(21) Appl. No.: 16/318,463

(22) PCT Filed: Jul. 19, 2017

(86) PCT No.: PCT/US2017/042938
§ 371 (c)(1),
(2) Date: Jan. 17, 2019

(87) PCT Pub. No.: WO2018/017767
PCT Pub. Date: Jan. 25, 2018

(65) Prior Publication Data
US 2019/0261908 A1    Aug. 29, 2019

Related U.S. Application Data

(60) Provisional application No. 62/364,297, filed on Jul. 19, 2016.

(51) Int. Cl.
*A61B 5/16* (2006.01)
*G16H 20/70* (2018.01)
(Continued)

(52) U.S. Cl.
CPC ............ *A61B 5/162* (2013.01); *A61B 5/0051* (2013.01); *A61B 5/0077* (2013.01); *A61B 5/11* (2013.01);
(Continued)

(58) Field of Classification Search
CPC ....... A61B 5/162; A61B 5/168; A61B 5/4088; A61B 5/7455; A61B 5/7475; G16H 20/70; G09B 7/02; G09B 19/00
See application file for complete search history.

(56) References Cited

U.S. PATENT DOCUMENTS 6,585,518 B1   7/2003   Jenkins et al.
8,016,416 B1   9/2011   Straus
(Continued)

FOREIGN PATENT DOCUMENTS

EP   2031572 A2    3/2009
JP   2006503359 A  1/2006
(Continued)

OTHER PUBLICATIONS

Ratcliff, R., "The Diffusion Decision Model: Theory and Data for Two-Choice Decision Tasks", Apr. 2008, Neural Computation, 20, 873-922 (Year: 2008).*
(Continued)

*Primary Examiner* — Jay Trent Liddle
*Assistant Examiner* — Alyssa N Brandley
(74) *Attorney, Agent, or Firm* — Gregory Finch; Finch Paolino, LLC

(57) ABSTRACT

Example systems, methods, and apparatus, including cognitive platforms, are provided for applying signal detection
(Continued)

metrics in computer-implemented adaptive response-deadline procedures to data collected based at least in part on user interaction(s) with computerized tasks and/or interferences. The apparatus can include a response classifier for generating a quantifier of the cognitive abilities of an individual. The apparatus also can be configured to adapt the tasks and/or interferences to enhance the individual's cognitive abilities.

32 Claims, 35 Drawing Sheets

(51) Int. Cl.
| | |
|---|---|
| A61B 5/00 | (2006.01) |
| G09B 19/00 | (2006.01) |
| G09B 5/00 | (2006.01) |
| A61B 5/11 | (2006.01) |
| A61P 25/00 | (2006.01) |
| G16H 50/70 | (2018.01) |
| G09B 7/02 | (2006.01) |
| G16H 50/30 | (2018.01) |
| G16H 40/63 | (2018.01) |
| A61B 5/145 | (2006.01) |
| A61B 5/024 | (2006.01) |
| A61B 5/0533 | (2021.01) |
| A61B 5/0205 | (2006.01) |
| A61B 5/08 | (2006.01) |
| A61B 5/021 | (2006.01) |
| A61B 5/369 | (2021.01) |
| A61B 5/389 | (2021.01) |

(52) U.S. Cl.
CPC ............ *A61B 5/1124* (2013.01); *A61B 5/16* (2013.01); *A61B 5/168* (2013.01); *A61B 5/4076* (2013.01); *A61B 5/4082* (2013.01); *A61B 5/4088* (2013.01); *A61B 5/4833* (2013.01); *A61B 5/4839* (2013.01); *A61B 5/4842* (2013.01); *A61B 5/4848* (2013.01); *A61B 5/7267* (2013.01); *A61B 5/7405* (2013.01); *A61B 5/7455* (2013.01); *A61B 5/7475* (2013.01); *A61P 25/00* (2018.01); *G09B 5/00* (2013.01); *G09B 7/02* (2013.01); *G09B 19/00* (2013.01); *G16H 20/70* (2018.01); *G16H 40/63* (2018.01); *G16H 50/30* (2018.01); *G16H 50/70* (2018.01); *A61B 5/021* (2013.01); *A61B 5/024* (2013.01); *A61B 5/0205* (2013.01); *A61B 5/02405* (2013.01); *A61B 5/0533* (2013.01); *A61B 5/0816* (2013.01); *A61B 5/1122* (2013.01); *A61B 5/14532* (2013.01); *A61B 5/14542* (2013.01); *A61B 5/369* (2021.01); *A61B 5/389* (2021.01); *A61B 2562/0204* (2013.01); *A61B 2562/0219* (2013.01); *A61B 2562/0247* (2013.01)

(56) References Cited

U.S. PATENT DOCUMENTS

| | | | |
|---|---|---|---|
| 8,343,012 | B2 | 1/2013 | Redmann |
| 9,265,458 | B2 | 2/2016 | Stack |
| 9,566,029 | B2 | 2/2017 | Faubert et al. |
| 11,122,998 | B2 | 9/2021 | Martucci et al. |
| 2004/0175683 | A1 | 9/2004 | Duffy et al. |
| 2005/0175972 | A1 | 8/2005 | Goldman et al. |
| 2005/0199010 | A1 | 9/2005 | Coleman et al. |
| 2006/0089335 | A1 | 4/2006 | Liu et al. |
| 2007/0141541 | A1 | 6/2007 | Chan et al. |
| 2007/0299319 | A1 | 12/2007 | Chan et al. |
| 2008/0028276 | A1 | 1/2008 | Li et al. |
| 2009/0031217 | A1 | 1/2009 | Tysbo |
| 2010/0092929 | A1 | 4/2010 | Hallowell et al. |
| 2010/0094155 | A1 | 4/2010 | Prichep |
| 2010/0152249 | A1 | 6/2010 | Rasgon |
| 2010/0292545 | A1* | 11/2010 | Berka ............... A61B 5/374 600/301 |
| 2011/0005532 | A1 | 1/2011 | Faubert et al. |
| 2012/0059229 | A1 | 3/2012 | Faubert et al. |
| 2012/0088222 | A1 | 4/2012 | Considine et al. |
| 2012/0090446 | A1 | 4/2012 | Moreno |
| 2012/0108997 | A1 | 5/2012 | Guan et al. |
| 2012/0196257 | A1 | 8/2012 | Verghese et al. |
| 2012/0208169 | A1 | 8/2012 | Nutley et al. |
| 2012/0214143 | A1 | 8/2012 | Severson et al. |
| 2012/0258436 | A1 | 10/2012 | Lee |
| 2012/0271194 | A1 | 10/2012 | MacLullich et al. |
| 2013/0091453 | A1 | 4/2013 | Kotler et al. |
| 2013/0344000 | A1 | 12/2013 | Kaplin et al. |
| 2014/0019059 | A1 | 1/2014 | Shankle et al. |
| 2014/0279746 | A1 | 9/2014 | De Bruin et al. |
| 2014/0315169 | A1 | 10/2014 | Bohbot |
| 2014/0323013 | A1 | 10/2014 | Gonzalez-Heydrich et al. |
| 2014/0370479 | A1* | 12/2014 | Gazzaley ............ A61B 5/168 434/322 |
| 2015/0004577 | A1 | 1/2015 | Wu et al. |
| 2015/0024357 | A1 | 1/2015 | Faubert et al. |
| 2015/0112899 | A1 | 4/2015 | Dagum |
| 2015/0119731 | A1 | 4/2015 | Yasumura et al. |
| 2015/0187227 | A1 | 7/2015 | Zhang et al. |
| 2015/0199010 | A1* | 7/2015 | Coleman ............. H04L 12/16 345/156 |
| 2016/0078780 | A1 | 3/2016 | Alexander et al. |
| 2016/0125748 | A1 | 5/2016 | Ashford |
| 2016/0125758 | A1* | 5/2016 | Hong ................ G09B 7/02 434/236 |
| 2016/0155355 | A1 | 6/2016 | Merzenich et al. |
| 2016/0262680 | A1 | 9/2016 | Martucci et al. |
| 2016/0310059 | A1 | 10/2016 | Faubert et al. |
| 2016/0351069 | A1 | 12/2016 | Faubert et al. |
| 2018/0286272 | A1* | 10/2018 | Mcdermott ........... A63F 13/69 |

FOREIGN PATENT DOCUMENTS

| | | |
|---|---|---|
| JP | 2014508309 A | 4/2014 |
| JP | 2014508309 A | 4/2014 |
| WO | WO-2004036499 A1 | 4/2004 |
| WO | 2012064999 A1 | 5/2012 |
| WO | WO-2012064999 A1 | 5/2012 |
| WO | 2013111746 A1 | 8/2013 |
| WO | WO-2014138925 A1 | 9/2014 |
| WO | WO-2015049234 A1 | 4/2015 |
| WO | WO-2015179522 A1 | 11/2015 |
| WO | WO-2015192021 A1 | 12/2015 |

OTHER PUBLICATIONS

Aleksandar, T., "Machine learning approach for classification of ADHD adults", 2014, International Journal of Psychophysiology, 93, 162-166 (Year: 2014).*

Anguera, et al., "Video game training enhances cognitive control in older adults," Nature, (Sep. 2013), vol. 501. 36 pages.

Annex to European Patent Office Communication dated Sep. 19, 2018, for Application No. 15795907.3, 5 pg.

Australian Examination Report No. 1 dated Nov. 26, 2018 for Application No. 2015264260, 3 pages.

Baniqued, et al., "Selling Points: What Cognitive Abilities are Tapped by Casual Video Games?," Acta psycholgica, (2013), vol. 142, No. 1, pp. 74-86.

Caron, "Gaming & Culture—Of gyroscopes and gaming: the tech behind the Wii MotionPlus," Aug. 26, 2008, https://arstechnica.com/gaming/2008/08/wii-motion-sensor/, pp. 1-8.

Charron, et al., Divided Representation of Concurrent Goals in the Human Frontal Lobes, Science, (Apr. 2010), vol. 328, No. 5975, pp. 360-363.

(56) References Cited

OTHER PUBLICATIONS

Colich, et al., "Neural Aspects of Inhibition Following Emotional Primes in Depressed Adolescents," J Clin Child Adolesc Psychol., (2016), vol. 45, No. 1, pp. 21-30.
Communication Pursuant to Article 94(3) dated Sep. 19, 2018, for Application No. 15795907.3, 2 pg.
Communication Pursuant to Rule 161(2) and 162 dated Jan. 4, 2017, for Application No. 15795907.3, 2 pg.
Communication Pursuant to Rule 161(2) and 162 dated Feb. 28, 2019, for Application No. 17831833.3, 3 pg.
Communication Pursuant to Rule 161(2) and 162 dated Mar. 12, 2019, for Application No. 17837724.8, 3 pg.
International Search Report and Written Opinion dated Nov. 28, 2018, for Application No. PCT/US2018/00179, 18 pg.
Extended European Search Report dated Oct. 11, 2018, for Application No. 16762544.9, 11 pg.
Hastie, et al., The Elements of Statistical Learning, 2nd Edition, Springer (2009), 44 pages.
International Preliminary Report on Patentability dated Nov. 22, 2016 for International Application No. PCT/US2015/031780 (14 pages).
International Search Report and Written Opinion dated Aug. 19, 2015 for International Application No. PCT/US2015/031780 (12 pages).
International Search Report and Written Opinion dated Dec. 4, 2018 for International Application No. PCT/US2018/045206 (19 pages).
International Search Report and Written Opinion dated Nov. 7, 2017 for International Application No. PCT/US2017/048698 (30 pages).
International Search Report and Written Opinion dated Oct. 13, 2017 for International Application No. PCT/US2017/045385 (30 pages).
International Search Report and Written Opinion dated Sep. 29, 2017 for International Application No. PCT/US2017/042938 (21 pages).
International Search Report and Written Opinion dated Dec. 28, 2017 for International Application No. PCT/US2017/058103. 18 pages.
International Search Report and Written Opinion dated Mar. 7, 2018 for International Application No. PCT/US2017/66214. 13 pages.
International Search Report and Written Opinion dated Mar. 29, 2018 for International Application No. PCT/US2018/13182. 12 pages.
Japanese Notice of Reasons for Rejection dated Dec. 7, 2018, for Application No. 2017-513600, 5 page.
Junco, et al. "Perceived Academic Effects of Instant Messaging Use," Computers & Education, (2011), vol. 56, pp. 370-378.
Kautz, et al., "Fostering and Measuring Skills: Improving Cognitive and Non-Cognitive Skills to Promote Lifetime Success," National Bureau of Economic Research, (Sep. 2007), 87 pages.
Laricchiuta, et al., Individual differences in response to positive and negative stimuli: endocannabinoid-based insight on approach and avoidance behaviors, Frontiers in Systems Neuroscience, (Dec. 2014), vol. 8, Article 238, 22 pages.
Mayer, et al., "Nine Ways to Reduce Cognitive Load in Multimedia Learning," Education Psychologist, (2003), vol. 38, No. 1, pp. 43-52.
Pashler, "Dual-Task Interference in Simple Tasks: Data and Theory," Psychological Bulletin, (1994), vol. 116, No. 2, pp. 220-244.
Written Opinion dated May 26, 2016, for Application No. PCT/US2016/022115, 13 pg.
Compass, "Psilocybin therapy Background and Key findings from prior published studies," Compass Pathways Powerpoint presentation, (2018), 11 pages.
Compass, Transforming mental health through psychoactive care pathways, Compass Pathways Powerpoint presentation, (Jan. 2018), 19 pages.
Rucker, et al., "Psychedelics in the treatment of unipolar mood disorders: a systematic review," Journal of Psychopharmacology, (2016), pp. 1-10.
Hawkins, G.E. et al., "Toward a Model-Based Cognitive Neuroscience of Mind Wandering." Neuroscience 310 (2015): 290-305. Elsevier Ltd.
Supplementary Partial European Search Report. Application No. EP 17831833.3. Feb. 10, 2020. European Patent Office, The Hague, Netherlands.
Tenev, A., et al., "Machine learning approach for classification of ADHD adults." International Journal of Psychophysiology, vol. 93, No. 1. Jan. 27, 2013. pp. 162-166. Elsevier B.V.
Ahmadi, A. et al., "Light-weight Single Trial EEG Signal Processing Algorithms: Computational Profiling for Low Power Design." IEEE 2011 Annual International Conference, Engineering in Medicine and Biology Society. Aug. 30, 2011, pp. 4426-4430.
Office Action, Australian application No. 2017299614, dated May 26, 2022. IP Australia, Phillip, AU.
Office Action, English translation. Japanese application No. 2019-502690, dated Apr. 19, 2021. Japan Patent Office, Tokyo, JP.
Office Action, English translation. Japanese application No. 2019-502690, dated Feb. 14, 2022. Japan Patent Office, Tokyo, JP.
Extended European Search Report, European application No. 17831833.3, dated Jun. 26, 2020. European Patent Office, Munich, DE.
Office Action, European application No. 17831833.3, dated Sep. 28, 2022. European Patent Office, Rijswijk, NL.
Office Action, English translation. Korean application No. 10-2019-7004637, dated Nov. 25, 2021. Korean Intellectual Property Office, Daejeon, KR.

\* cited by examiner

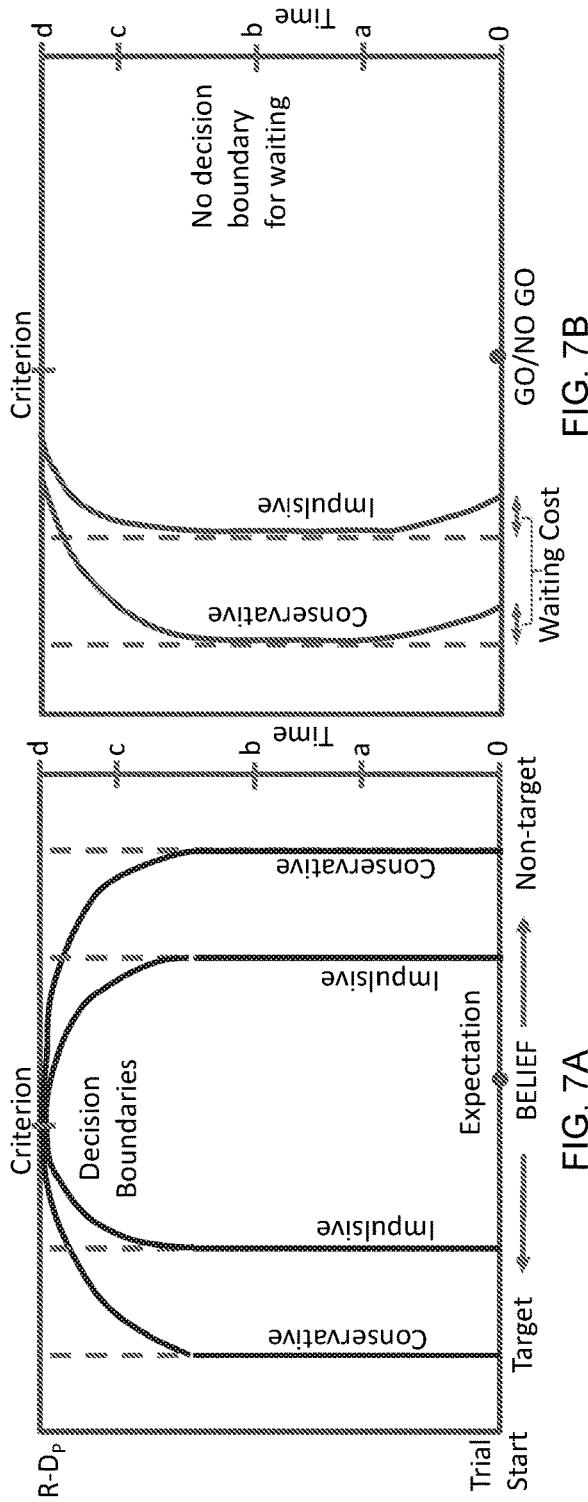
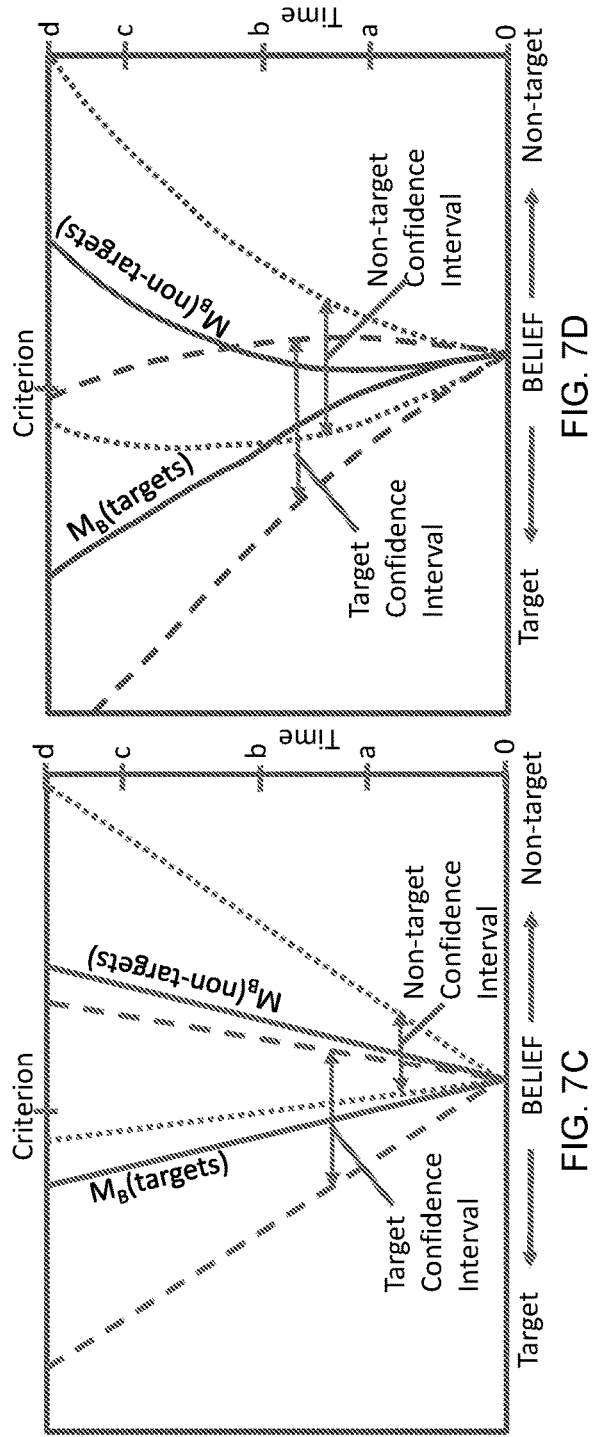
FIG. 7A
FIG. 7B
FIG. 7C
FIG. 7D

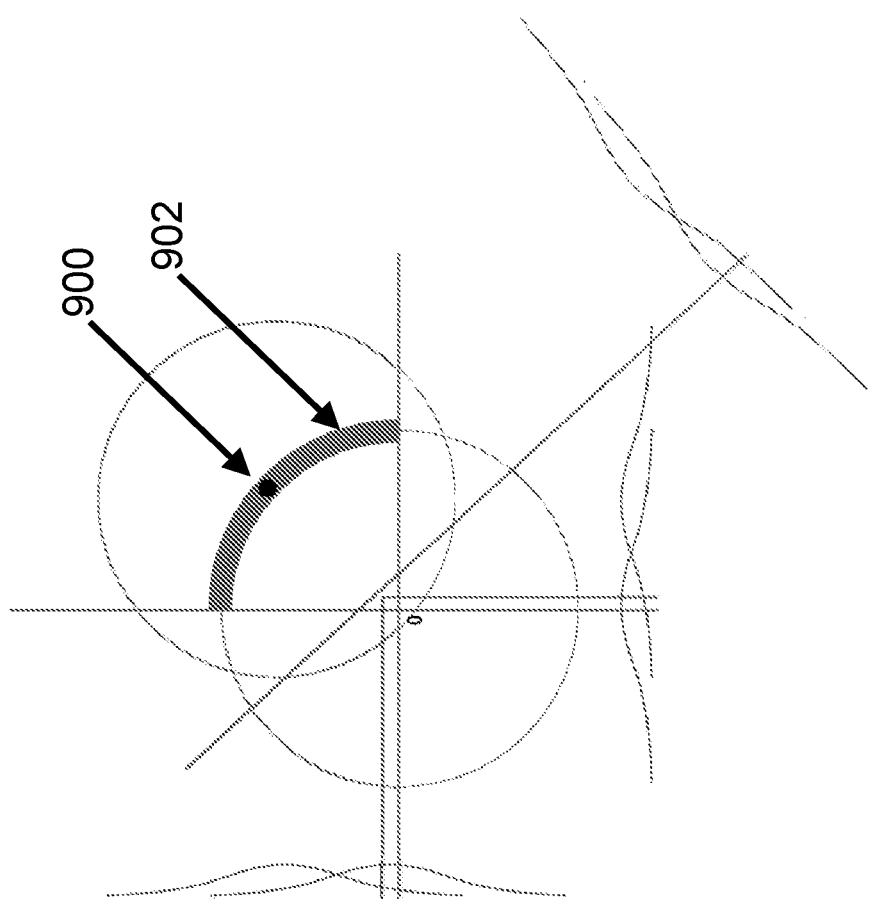

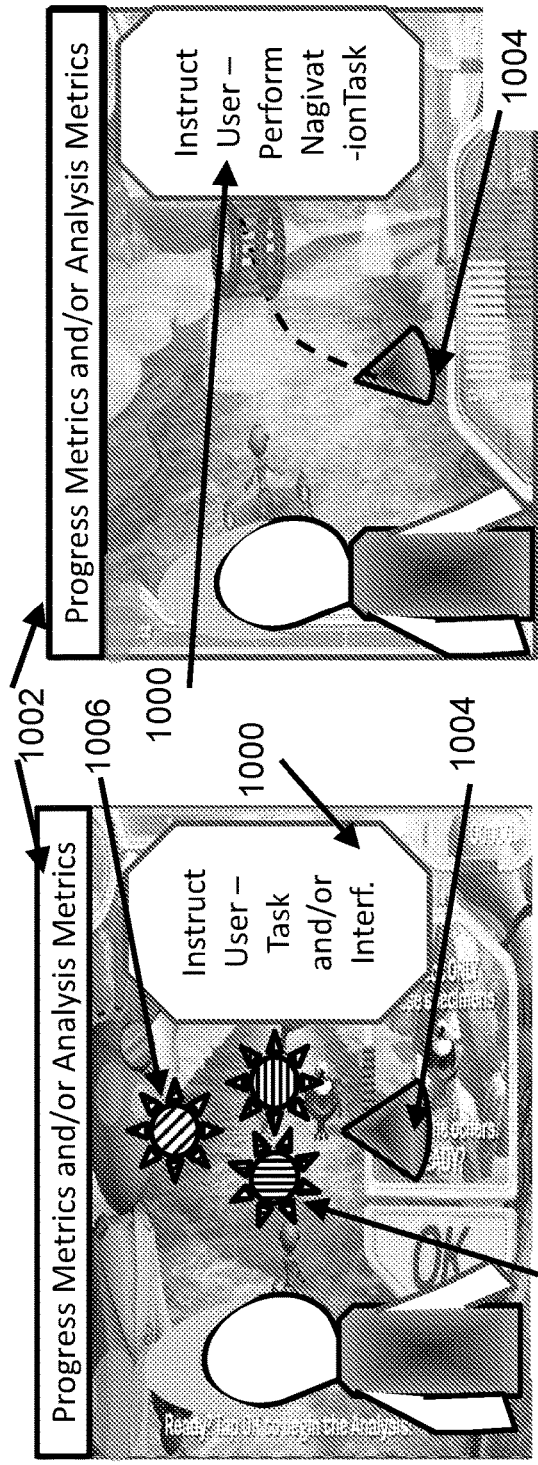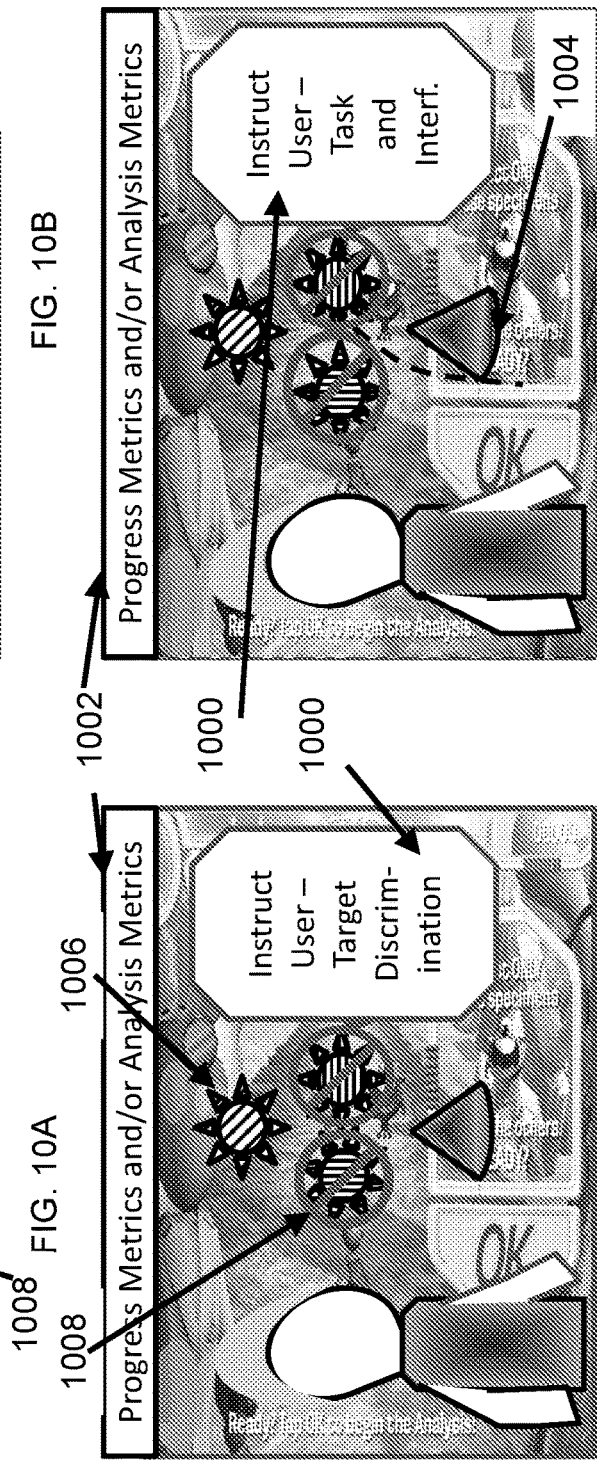
FIG. 10A FIG. 10B FIG. 10C FIG. 10D

PLATFORMS TO IMPLEMENT SIGNAL DETECTION METRICS IN ADAPTIVE RESPONSE-DEADLINE PROCEDURES

CROSS-REFERENCE TO RELATED APPLICATIONS

This application is the national stage application of International (PCT) Patent Application Serial No. PCT/US2017/042938, filed Jul. 19, 2017, which claims priority benefit of U.S. provisional application No. 62/364,297, entitled "SIGNAL DETECTION METRICS IN ADAPTIVE RESPONSE-DEADLINE PROCEDURES," filed on Jul. 19, 2016, and of U.S. design application numbed 29/579,480 entitled "GRAPHICAL USER INTERFACE FOR A DISPLAY SCREEN OR PORTION THEREOF," filed on Sep. 30, 2016; each of these three applications is incorporated herein by reference in its entirety, including drawings.

BACKGROUND OF THE DISCLOSURE

In the normal course of aging, individuals can experience a certain amount of cognitive decline. This can cause an individual to experience increased difficulty in challenging situations, such as time-limited, attention-demanding conditions. In both older and younger individuals, certain cognitive conditions, diseases, or executive function disorders can result in compromised performance at tasks that require attention, memory, motor function, reaction, executive function, decision-making skills, problem-solving skills, language processing, or comprehension.

SUMMARY OF THE DISCLOSURE

In view of the foregoing, apparatus, systems and methods are provided for quantifying aspects of cognition (including cognitive abilities). In certain configurations, the apparatus, systems and methods can be implemented for enhancing certain cognitive abilities.

Example apparatus, systems and methods are configured for applying signal detection metrics in computer-implemented adaptive response-deadline procedures to data collected based at least in part on user interaction(s) with computerized tasks and/or interferences. For example, the apparatus can include a response classifier for generating a quantifier of the cognitive abilities of an individual. As another example, the apparatus also can be configured to adapt the tasks and/or interferences to enhance the individual's cognitive abilities.

In a general aspect, an apparatus for generating a quantifier of cognitive skills in an individual using a response classifier is provided. The apparatus includes a user interface; a memory to store processor-executable instructions; and a processing unit communicatively coupled to the user interface and the memory, in which upon execution of the processor-executable instructions by the processing unit, the processing unit is configured to render a task with an interference at the user interface, one or more of the task and the interference being time-varying and having a response deadline, such that the user interface imposes a limited time period for receiving at least one type of response from an individual; and the user interface being configured to measure data indicative of two or more differing types of responses to the task or to the interference. The processing unit is further configured to receive data indicative of a first response of an individual to the task and a second response of the individual to the interference; analyze the data indicative of the first response and the second response to compute at least one response profile representative of a performance of the individual; determine a decision boundary metric from the response profile, the decision boundary metric comprising a quantitative measure of a tendency of the individual to provide at least one type of response of the two or more differing types of responses to the task or the interference; and execute a response classifier based at least in part on the computed values of decision boundary metric, to generate a classifier output indicative of the cognitive response capabilities of the individual.

In another general aspect, a computer-implemented method for generating a quantifier of cognitive skills in an individual using a response classifier is provided. The method includes rendering a task with an interference at a user interface; measuring data indicative of two or more differing types of responses to the task or to the interference; receiving data indicative of a first response of an individual to the task and a second response of the individual to the interference. The method includes analyzing the data indicative of the first response and the second response to compute at least one response profile representative of the performance of the individual. The method includes determining a decision boundary metric from the response profile, the decision boundary metric comprising a quantitative measure of a tendency of the individual to provide at least one type of response of the two or more differing types of responses to the interference. The method includes executing a response classifier based at least in part on the decision boundary metric, to generate a classifier output indicative of the individual's cognitive response capabilities.

In another general aspect, an apparatus for enhancing cognitive skills in an individual is provided. The apparatus includes a user interface; a memory to store processor-executable instructions; and a processing unit communicatively coupled to the user interface and the memory, in which upon execution of the processor-executable instructions by the processing unit, the processing unit is configured to render a primary task with an interference at the user interface, one or more of the task and the interference being time-varying and having a response deadline, such that the user interface imposes a limited time period for receiving at least one type of response from an individual; and the user interface being configured to measure data indicative of two or more differing types of responses to the task or to the interference. The processing unit is configured to receive data indicative of a first response of an individual to the task and a second response of the individual to the interference; and analyze the data indicative of the first response and the second response to compute at least one response profile representative of a performance of the individual. The processing unit is configured to determine a first decision boundary metric based at least in part on the at least one response profile, the first decision boundary metric comprising a quantitative measure of a tendency of the individual to provide at least one type of response of the two or more differing types of responses to the interference. The processing unit is configured to, based at least in part on the computed first decision boundary metric, adjust the task and/or the interference to derive a modification in the computed at least one decision boundary metric such that a further response to the task and/or a further response to the interference is modified as compared to an earlier response to the task and/or an earlier response to the interference, thereby indicating a modification of the cognitive response capabilities of the individual.

In another general aspect, a computer-implemented method for enhancing cognitive skills in an individual is provided. The method includes rendering a task with an interference at a user interface; measuring data indicative of two or more differing types of responses to the task or to the interference; receiving data indicative of a first response of an individual to the task and a second response of the individual to the interference; and analyzing the data indicative of the first response and the second response to compute at least one response profile representative of the performance of the individual. The method includes determining a first decision boundary metric based at least in part on the at least one response profile, the first decision boundary metric comprising a quantitative measure of a tendency of the individual to provide at least one type of response of the two or more differing types of responses to the interference. The method includes, based at least in part on the computed first decision boundary metric, adapting the task and/or the interference to derive a modification in the computed first decision boundary metric such that the first response and/or the second response is modified, thereby indicating a modification of the cognitive response capabilities of the individual.

In another general aspect, an apparatus for enhancing cognitive skills in an individual is provided. The apparatus includes a user interface; a memory to store processor-executable instructions; and a processing unit communicatively coupled to the user interface and the memory, in which upon execution of the processor-executable instructions by the processing unit, the processing unit is configured to receive data indicative of one or more of an amount, concentration, or dose titration of a pharmaceutical agent, drug, or biologic being or to be administered to an individual. The processing unit is configured to render a primary task with an interference at the user interface, one or more of the task and the interference being time-varying and having a response deadline, such that the user interface imposes a limited time period for receiving at least one type of response from an individual; and the user interface being configured to measure data indicative of two or more differing types of responses to the task or to the interference. The processing unit is configured to receive data indicative of a first response of an individual to the task and a second response of the individual to the interference, from a first session; analyze the data indicative of the first response and the second response to compute a first response profile representative of a first performance of the individual; and determine a first decision boundary metric based at least in part on the at least one response profile, the first decision boundary metric comprising a quantitative measure of a tendency of the individual to provide at least one type of response of the two or more differing types of responses to the interference. The processing unit is configured to, based at least in part on the computed first decision boundary metric and the amount or concentration of a pharmaceutical agent, drug, or biologic, adapt the task and/or the interference to generate a second session. The processing unit is configured to analyze collected data indicative of the first response and the second response from the second session, to compute a second response profile and a second decision boundary metric representative of a second performance of the individual. The processing unit is configured to, based at least in part on the first decision boundary metric and second decision boundary metric, generate an output to the user interface indicative of at least one of: (i) a likelihood of the individual experiencing an adverse event in response to administration of the pharmaceutical agent, drug, or biologic, (ii) a recommended change in one or more of the amount, concentration, or dose titration of the pharmaceutical agent, drug, or biologic, (iii) a change in the individual's cognitive response capabilities, (iv) a recommended treatment regimen, (v) a recommendation of at least one of a behavioral therapy, counseling, or physical exercise, or (vi) a degree of effectiveness of at least one of a behavioral therapy, counseling, or physical exercise.

In another general aspect, a computer-implemented method for enhancing cognitive skills in an individual is provided. The method includes receiving data indicative of one or more of an amount, concentration, or dose titration of a pharmaceutical agent, drug, or biologic being or to be administered to an individual. The method includes rendering a task with an interference at a user interface; measuring data indicative of two or more differing types of responses to the task or to the interference; receiving data indicative of a first response of an individual to the task and a second response of the individual to the interference; and analyzing the data indicative of the first response and the second response to compute a first response profile representative of the performance of the individual. The method includes determining a first decision boundary metric based at least in part on the at least one response profile, the first decision boundary metric comprising a quantitative measure of a tendency of the individual to provide at least one type of response of the two or more differing types of responses to the interference. The method includes, based at least in part on the computed first decision boundary metric and the amount or concentration of a pharmaceutical agent, drug, or biologic, adapting the task and/or the interference such that the at least one response profile is modified. The method includes analyzing the collected data indicative of the first response and the second response to compute a second decision boundary metric representative of a second performance of the individual. The method includes, based at least in part on the first decision boundary metric and second decision boundary metric, generate an output to the user interface indicative of at least one of (i) a change in one or more of the amount, concentration, or dose titration of the pharmaceutical agent, drug, or biologic, (ii) a likelihood of the individual experiencing an adverse event in response to administration of the pharmaceutical agent, drug, or biologic, (iii) a change in the individual's cognitive response capabilities, (iv) a recommended treatment regimen, (v) a recommendation of at least one of a behavioral therapy, counseling, or physical exercise, or (vi) a degree of effectiveness of at least one of a behavioral therapy, counseling, or physical exercise.

The details of one or more of the above aspects and implementations are set forth in the accompanying drawings and the description below. Other features, aspects, and advantages will become apparent from the description, the drawings, and the claims.

BRIEF DESCRIPTION OF DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which:

FIGS. 7A-7B show plots of the curves for values of conservative and impulsive measures, according to the principles herein.

FIGS. 7C-7D show example plots of the formation of belief for linear belief accumulation and non-linear belief accumulation, respectively, according to the principles herein.

FIG. 9 shows an example projected two-dimensional (2D) representation of a three-dimensional (3D) joint distribution, according to the principles herein.

FIGS. 10A-10D show example user interfaces with instructions to a user that can be rendered to an example user interface, according to the principles herein.

DETAILED DESCRIPTION

Figure 1:
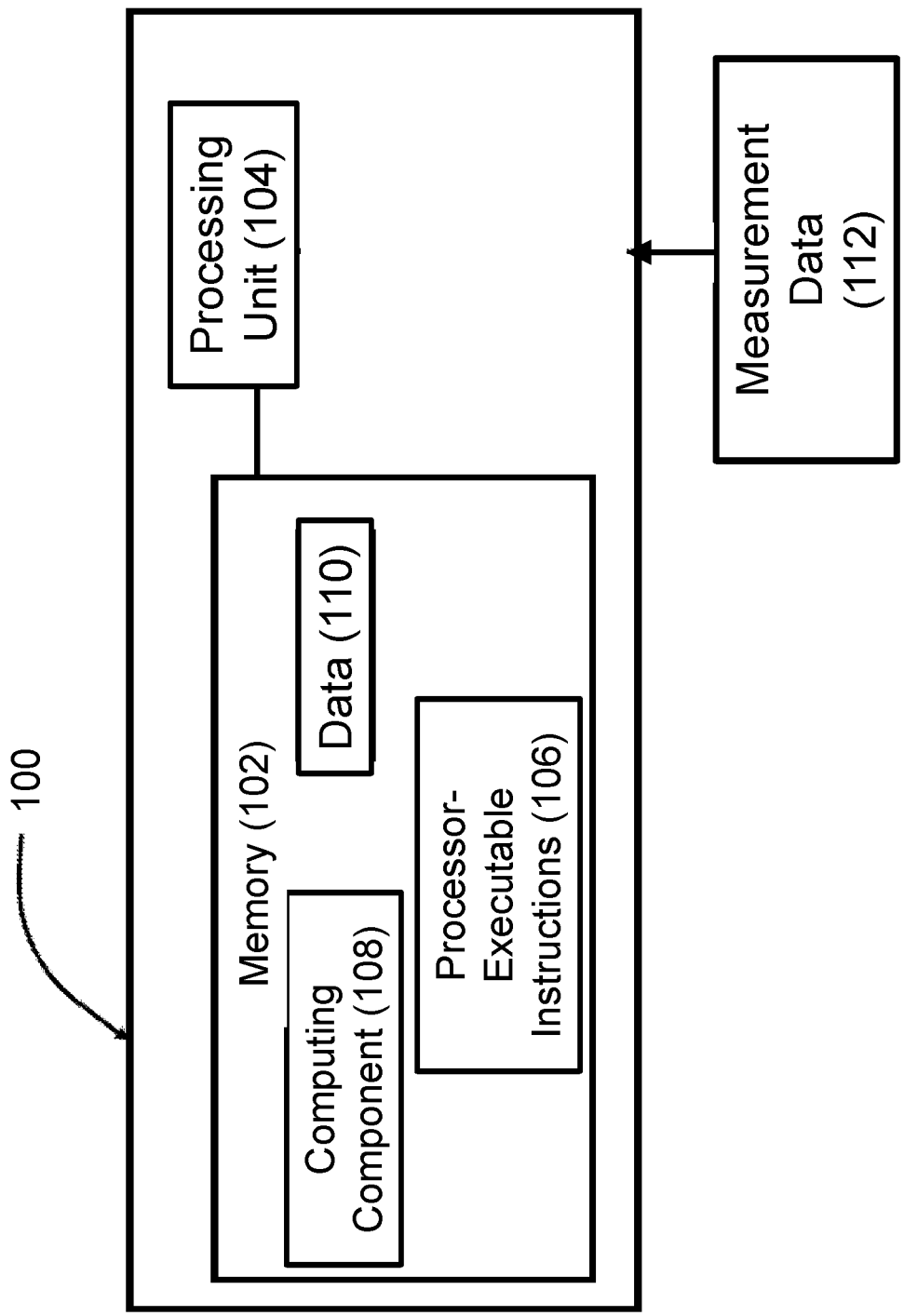
FIG. 1 shows a block diagram of an example system, according to the principles herein.

It should be appreciated that all combinations of the concepts discussed in greater detail below (provided such concepts are not mutually inconsistent) are contemplated as being part of the inventive subject matter disclosed herein. It also should be appreciated that terminology explicitly employed herein that also may appear in any disclosure incorporated by reference should be accorded a meaning most consistent with the particular concepts disclosed herein.

Following below are more detailed descriptions of various concepts related to, and embodiments of, inventive methods, apparatus and systems comprising a cognitive platform configured for applying signal detection metrics in computer-implemented adaptive response-deadline procedures.

It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

As used herein, the term "includes" means includes but is not limited to, the term "including" means including but not limited to. The term "based on" means based at least in part on.

As used herein, the term "target" refers to a type of stimulus that is specified to an individual (e.g., in instructions) to be the focus for an interaction. A target differs from a non-target in at least one characteristic or feature. Two targets may differ from each other by at least one characteristic or feature, but overall are still instructed to an individual as a target, in an example where the individual is instructed/required to make a choice (e.g., between two different degrees of a facial expression or other characteristic/feature difference, such as but not limited to between a happy face and a happier face or between an angry face and an angrier face).

As used herein, the term "non-target" refers to a type of stimulus that is not to be the focus for an interaction, whether indicated explicitly or implicitly to the individual.

As used herein, the term "task" refers to a goal and/or objective to be accomplished by an individual. The task may require the individual to provide or withhold a response to a particular stimulus. The "task" can be configured as a baseline cognitive function that is being measured.

As used herein, the term "interference" refers to a stimulus presented to the individual such that it interferes with the individual's performance of a primary task. In any example herein, an interference is a type of task that is presented/rendered in such a manner that it diverts or interferes with an individual's attention in performing another task. In some examples herein, the interference is configured as a secondary task that is presented simultaneously with a primary task, either over a short, discrete time period or over an extended time period (less than the time frame over which the primary task is presented), or over the entire period of time of the primary task. In any example herein, the interference can be presented/rendered continuously, or continually (i.e., repeated in a certain frequency, irregularly, or somewhat randomly). For example, the interference can be presented at the end of the primary task or at discrete, interim periods during presentation of the primary task. The degree of interference can be modulated based on the type, amount, and/or temporal length of presentation of the interference relative to the primary task.

As used herein, the term "stimulus," refers to a sensory event configured to evoke a specified functional response from an individual. The degree and type of response can be quantified based on the individual's interactions with a measuring component (including using sensor devices or other measuring components). Non-limiting examples of a stimulus include a navigation path (with an individual being instructed to control an avatar or other processor-rendered guide to navigate the path), or a discrete object, whether a target or a non-target, rendered to a user interface (with an individual being instructed to control a computing component to provide input or other indication relative to the discrete object). In any example herein, the task and/or interference includes a stimulus.

As used herein, a "trial" includes at least one iteration of rendering of a task and/or interference and at least one receiving of the individual's response(s) to the task and/or interference. As non-limiting examples, a trial can include at least a portion of a single-tasking task and/or at least a portion of a multi-tasking task. For example, a trial can be a period of time during a navigation task (including a visuo-motor navigation task) in which the individual's performance is assessed, such as but not limited to, assessing whether or the degree of success to which an individual's actions in interacting with the platform result in a guide (including a computerized avatar) navigating along at least a portion of a certain path or in an environment for a time interval (such as but not limited to, fractions of a second, a second, several seconds, or more) and/or causes the guide (including computerized avatar) to cross (or avoid crossing) performance milestones along the path or in the environment. In another example, a trial can be a period of time during a targeting task in which the individual's performance is assessed, such as but not limited to, assessing whether or the degree of success to which an individual's actions in interacting with the platform result in identification/selection of a target versus a non-target (e.g., red object versus yellow object), or discriminates between two different types of targets (a happy face versus a happier face). In these examples, the segment of the individual's performance that is designated as a trial for the navigation task does not need to be co-extensive or aligned with the segment of the individual's performance that is designated as a trial for the targeting task.

As used herein, a "session" refers to at least one trial or can include at least one trial and at least one other type of measurement and/or other user interaction. As a non-limiting example, a session can include at least one trial and one or more of a measurement using a physiological or monitoring component and/or a cognitive testing component. As another non-limiting example, a session can include at least one trial and receipt of data indicative of one or more measures of an individual's condition, including physiological condition and/or cognitive condition.

In any example herein, an object may be rendered as a depiction of a physical object (including a polygonal or other object), a face (human or non-human), or a caricature, other type of object.

In any of the examples herein, instructions can be provided to the individual to specify how the individual is expected to perform the task and/or interference in a trial and/or a session. In non-limiting examples, the instructions can inform the individual of the expected performance of a navigation task (e.g., stay on this path, go to these parts of the environment, cross or avoid certain milestone objects in the path or environment), a targeting task (e.g., describe or show the type of object that is the target object versus the non-target object, or describe or show the type of object that is the target object versus the non-target object, or two different types of target object that the individual is expected to choose between (e.g., happy face versus happier face)), and/or describe how the individual's performance is to be scored. In examples, the instructions may be provided visually (e.g., based on a rendered user interface) or via sound. In various examples, the instructions may be provided once prior to the performance two or more trials or sessions, or repeated each time prior to the performance of a trial or a session, or some combination thereof.

While some example systems, methods, and apparatus described herein are based on an individual being instructed/required to decide/select between a target versus a non-target may, in other example implementations, the example systems, methods, and apparatus can be configured such that the individual is instructed/required to decide/choose between two different types of targets (such as but not limited to between two different degrees of a facial expression or other characteristic/feature difference).

In addition, while example systems, methods, and apparatus may be described herein relative to an individual, in other example implementations, the example systems, methods, and apparatus can be configured such that two or more individuals, or members of a group (including a clinical population), perform the tasks and/or interferences, either individually or concurrently.

The instant disclosure is directed to the application of signal detection metrics such as criterion, bias, and sensitivity indices to computer-implemented adaptive time-deadline procedures.

The example systems, methods, and apparatus according to the principles herein can be implemented, using at least one processing unit of a programmed computing device, to characterize the response profiles of individuals and groups on the spectrum between impulsive (tend to respond with limited information) or conservative (tend to withhold response until maximum information is acquired) in psychophysical computer-implemented adaptive testing procedures.

As described in greater detail below, the computing device can include an application (an "App") to perform such functionalities as analyzing the data. For example, the data from the at least one sensor component can be analyzed as described herein by a processor executing the App on an example computing device to provide the computed response profile, decision boundary metric (such as but not limited to response criteria), response classifier, and other metrics and analyses described herein.

An example system according to the principles herein provides for generating a quantifier of cognitive skills in an individual (using a machine learning response classifier) and/or enhancing cognitive skills in an individual. In an example implementation, the example system employs an App running on a mobile communication device or other hand-held devices. Non-limiting examples of such mobile communication devices or hand-held device include a smartphone, such as but not limited to an iPhone®, a BlackBerry®, or an Android-based smartphone, a tablet, a slate, an electronic-reader (e-reader), a digital assistant, or other electronic reader or hand-held, portable, or wearable computing device, or any other equivalent device, an Xbox®, a Wii®, or other computing system that can be used to render game-like elements. In some example implementations, the example system can include a head-mounted device, such as smart eyeglasses with built-in displays, a smart goggle with built-in displays, or a smart helmet with built-in displays, and the user can hold a controller or an input device having one or more sensors in which the controller or the input device communicates wirelessly with the head-mounted device. In some example implementations, the computing system may be stationary, such as a desktop computing system that includes a main computer and a desktop display (or a projector display), in which the user provides inputs to the App using a keyboard, a computer mouse, a joystick, handheld consoles, wristbands, or other wearable devices having sensors that communicate with the main computer using wired or wireless communication. In examples herein, the sensors can be configured to measure movements of the user's hands, feet, and/or any other part of the body. In some example implementations, the example system can be formed as a virtual reality (VR) system (a simulated environment including as an immersive, interactive 3-D experience for a user), an augmented reality (AR) system (including a live direct or indirect view of a physical, real-world environment whose elements are augmented by computer-generated sensory input such as but not limited to sound, video, graphics and/or GPS data), or a mixed reality (MR) system (also referred to as a hybrid reality which merges the real and virtual worlds to produce new environments and visualizations where physical and digital objects co-exist and interact substantially in real time).

FIG. 1 shows an example apparatus 100 according to the principles herein that can be used to implement the cognitive platform according to the principles herein. The example apparatus 100 includes at least one memory 102 and at least one processing unit 104. The at least one processing unit 104 is communicatively coupled to the at least one memory 102.

Example memory 102 can include, but is not limited to, hardware memory, non-transitory tangible media, magnetic storage disks, optical disks, flash drives, computational device memory, random access memory, such as but not limited to DRAM, SRAM, EDO RAM, any other type of memory, or combinations thereof. Example processing unit 104 can include, but is not limited to, a microchip, a processor, a microprocessor, a special purpose processor, an application specific integrated circuit, a microcontroller, a field programmable gate array, any other suitable processor, or combinations thereof.

The at least one memory 102 is configured to store processor-executable instructions 106 and a computing component 108. In a non-limiting example, the computing component 108 can be used to compute signal detection metrics in computer-implemented adaptive response-deadline procedures. As shown in FIG. 1, the memory 102 also can be used to store data 110, such as but not limited to measurement data 112. In various examples, the measurement data 112 can include physiological measurement data of an individual received from a physiological component (not shown) and/or data indicative of the response of an individual to a task and/or an interference rendered at a user interface of the apparatus 100 (as described in greater detail below), and/or data indicative of one or more of an amount, concentration, or dose titration, or other treatment regimen of a drug, pharmaceutical agent, biologic, or other medication being or to be administered to an individual.

In a non-limiting example, the at least one processing unit 104 executes the processor-executable instructions 106 stored in the memory 102 at least to compute signal detection metrics in computer-implemented adaptive response-deadline procedures using the computing component 108. The at least one processing unit 104 also executes processor-executable instructions 106 to control a transmission unit to transmit values indicative of the computed signal detection metrics and/or controls the memory 102 to store values indicative of the signal detection metrics.

In another non-limiting example, the at least one processing unit 104 executes the processor-executable instructions 106 stored in the memory 102 at least to apply signal detection metrics in computer-implemented adaptive response-deadline procedures.

In any example herein, the user interface may be a graphical user interface.

In another non-limiting example, the measurement data 112 can be collected from measurements using one or more physiological or monitoring components and/or cognitive testing components. In any example herein, the one or more physiological components are configured for performing physiological measurements. The physiological measurements provide quantitative measurement data of physiological parameters and/or data that can be used for visualization of physiological structure and/or functions.

In any example herein, the measurement data 112 can include reaction time, response variance, correct hits, omission errors, number of false alarms (such as but not limited to a response to a non-target), learning rate, spatial deviance, subjective ratings, and/or performance threshold, or data from an analysis, including percent accuracy, hits, and/or misses in the latest completed trial or session. Other non-limiting examples of measurement data 112 include response time, task completion time, number of tasks completed in a set amount of time, preparation time for task, accuracy of responses, accuracy of responses under set conditions (e.g., stimulus difficulty or magnitude level and association of multiple stimuli), number of responses a participant can register in a set time limit number of responses a participant can make with no time limit, number of attempts at a task needed to complete a task, movement stability, accelerometer and gyroscope data, and/or self-rating.

For a target discrimination task, the cognitive platform may require a temporally-specific and/or a position-specific response from an individual, including to select between a target and a non-target (e.g., in a GO/NO-GO task) or to select between two differing types of targets, e.g., in a two-alternative forced choice (2AFC) task (including choosing between two differing degrees of a facial expression or other characteristic/feature difference). For a navigation task, the cognitive platform may require a position-specific and/or a motion-specific response from the user. For a facial expression recognition or object recognition task, the cognitive platform may require temporally-specific and/or position-specific responses from the user. In non-limiting examples, the user response to tasks, such as but not limited to targeting and/or navigation and/or facial expression recognition or object recognition task(s), can be recorded using an input device of the cognitive platform. Non-limiting examples of such input devices can include a device for capturing a touch, swipe or other gesture relative to a user interface, an audio capture device (e.g., a microphone input), or an image capture device (such as but not limited to a touch-screen or other pressure-sensitive or touch-sensitive surface, or a camera), including any form of graphical user interface configured for recording a user interaction. In other non-limiting examples, the user response recorded using the cognitive platform for tasks, such as but not limited to targeting and/or navigation and/or facial expression recognition or object recognition task(s), can include user actions that cause changes in a position, orientation, or movement of a computing device including the cognitive platform. Such changes in a position, orientation, or movement of a computing device can be recorded using an input device disposed in or otherwise coupled to the computing device, such as but not limited to a sensor. Non-limiting examples of sensors include a motion sensor, position sensor, and/or an image capture device (such as but not limited to a camera).

In any example herein, the multi-tasking tasks can include any combination of two or more tasks. The multi-task interactive elements of an implementation include interactive mechanics configured to engage the individual in multiple temporally-overlapping tasks, i.e., tasks that may require multiple, substantially simultaneous responses from an individual. In non-limiting examples herein, in an individual's performance of at least a portion of a multi-tasking task, the system, method, and apparatus are configured to measure data indicative of the individual's multiple responses in real-time, and also to measure a first response from the individual to a task (as a primary task) substantially simultaneously with measuring a second response from the individual to an interference (as a secondary task).

In an example implementation involving multi-tasking tasks, the computer device is configured (such as using at least one specially-programmed processing unit) to cause the cognitive platform to present to a user two or more different types of tasks, such as but not limited to, target discrimination and/or navigation and/or facial expression recognition or object recognition tasks, during a short time frame (including in real-time and/or substantially simultaneously). The computer device is also configured (such as using at least one specially-programmed processing unit) to collect data indicative of the type of user response received for the multi-tasking tasks, within the short time frame (including in real-time and/or substantially simultaneously). In these examples, the two or more different types of tasks can be presented to the individual within the short time frame (including in real-time and/or substantially simultaneously), and the computing device can be configured to receive data indicative of the user response(s) relative to the two or more different types of tasks within the short time frame (including in real-time and/or substantially simultaneously).

In some examples, the short time frame can be of any time interval at a resolution of up to about 1.0 millisecond or greater. The time intervals can be, but are not limited to, durations of time of any division of a periodicity of about 2.0 milliseconds or greater, up to any reasonable end time. The time intervals can be, but are not limited to, about 3.0 millisecond, about 5.0 millisecond, about 10 milliseconds, about 25 milliseconds, about 40 milliseconds, about 50 milliseconds, about 60 milliseconds, about 70 milliseconds, about 100 milliseconds, or greater. In other examples, the short time frame can be, but is not limited to, fractions of a second, about a second, between about 1.0 and about 2.0 seconds, or up to about 2.0 seconds, or more.

In any example herein, the cognitive platform can be configured to collect data indicative of a reaction time of a user's response relative to the time of presentation of the tasks (including an interference with a task). For example, the computing device can be configured to cause the platform product or cognitive platform to provide smaller or larger reaction time window for a user to provide a response to the tasks as an example way of adjusting the difficulty level.

In any example herein, the one or more physiological components can include any means of measuring physical characteristics of the body and nervous system, including electrical activity, heart rate, blood flow, and oxygenation levels, to provide the measurement data 112. This can include camera-based heart rate detection, measurement of galvanic skin response, blood pressure measurement, electroencephalogram, electrocardiogram, magnetic resonance imaging, near-infrared spectroscopy, and/or pupil dilation measures, to provide the measurement data 112. The one or more physiological components can include one or more sensors for measuring parameter values of the physical characteristics of the body and nervous system, and one or more signal processors for processing signals detected by the one or more sensors.

Other examples of physiological measurements to provide measurement data 112 include, but are not limited to, the measurement of body temperature, heart or other cardiac-related functioning using an electrocardiograph (ECG), electrical activity using an electroencephalogram (EEG), event-related potentials (ERPs), functional magnetic resonance imaging (fMRI), blood pressure, electrical potential at a portion of the skin, galvanic skin response (GSR), magneto-encephalogram (MEG), eye-tracking device or other optical detection device including processing units programmed to determine degree of pupillary dilation, functional near-infrared spectroscopy (fNIRS), and/or a positron emission tomography (PET) scanner. An EEG-fMRI or MEG-fMRI measurement allows for simultaneous acquisition of electrophysiology (EEG/MEG) data and hemodynamic (fMRI) data.

The example apparatus of FIG. 1 can be configured as a computing device for performing any of the example methods described herein. The computing device can include an App for performing some of the functionality of the example methods described herein.

Figure 2:
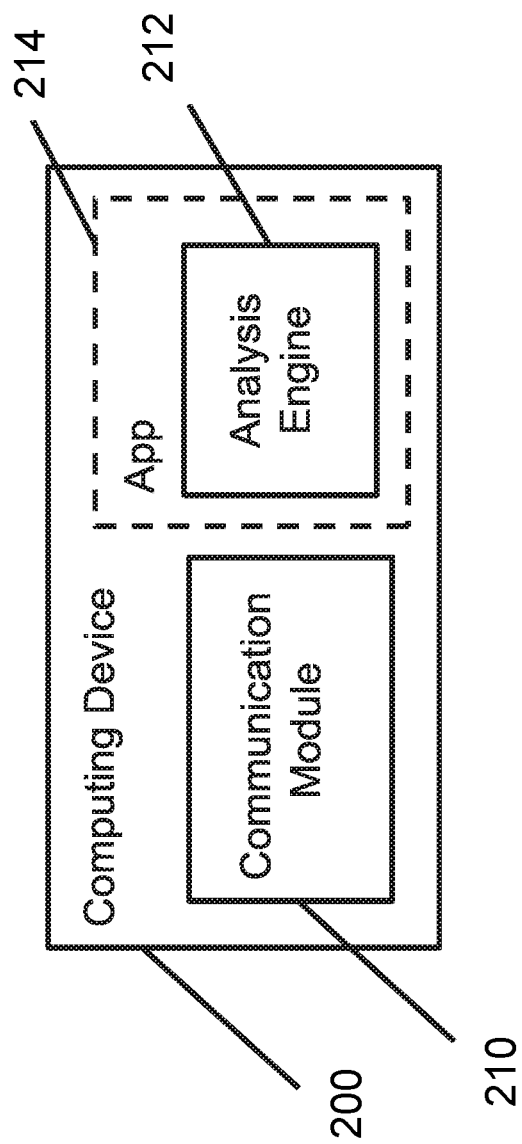
FIG. 2 shows a block diagram of an example computing device, according to the principles herein.

FIG. 2 shows another example apparatus according to the principles herein, configured as a computing device 200 that can be used to implement the cognitive platform according to the principles herein. The example computing device 200 can include a communication module 210 and an analysis engine 212. The communication module 210 can be implemented to receive data indicative of a response of an individual to the task and/or a response of the individual to the interference. The analysis engine 212 can be implemented to analyze the data to generate a response profile, decision boundary metric (such as but not limited to response criteria), a response classifier, and/or other metrics and analyses described herein. As shown in the example of FIG. 2, the computing device 200 can include processor-executable instructions such that a processor unit can execute an application (an App) 214 that a user can implement to initiate the analysis engine 212. In an example, the processor-executable instructions can include software, firmware, or other instructions.

The example communication module 210 can be configured to implement any wired and/or wireless communication interface by which information may be exchanged between the computing device 200 and another computing device or computing system. Non-limiting examples of wired communication interfaces include, but are not limited to, USB ports, RS232 connectors, RJ45 connectors, and Ethernet connectors, and any appropriate circuitry associated therewith. Non-limiting examples of wireless communication interfaces may include, but are not limited to, interfaces implementing Bluetooth® technology, Wi-Fi, Wi-Max, IEEE 802.11 technology, radio frequency (RF) communications, Infrared Data Association (IrDA) compatible protocols, Local Area Networks (LAN), Wide Area Networks (WAN), and Shared Wireless Access Protocol (SWAP).

In an example implementation, the example computing device 200 includes at least one other component that is configured to transmit a signal from the apparatus to a second computing device. For example, the at least one component can include a transmitter or a transceiver configured to transmit a signal including data indicative of a measurement by at least one sensor component to the second computing device.

In any example herein, the App 214 on the computing device 200 can include processor-executable instructions such that a processor unit of the computing device implements an analysis engine to analyze data indicative of the individual's response to the rendered tasks and/or interference to provide a response profile, decision boundary metric (such as but not limited to response criteria), a response classifier, and other metrics and analyses described herein. In some example, the App 214 can include processor-executable instructions to provide one or more of: (i) a classifier output indicative of the cognitive response capabilities of the individual, (ii) a likelihood of the individual experiencing an adverse event in response to administration of the pharmaceutical agent, drug, or biologic, (iii) a change in one or more of the amount, concentration, or dose titration of the pharmaceutical agent, drug, or biologic, and (iv) a change in the individual's cognitive response capabilities, a recommended treatment regimen, or recommending or determining a degree of effectiveness of at least one of a behavioral therapy, counseling, or physical exercise.

In any example herein, the App 214 can be configured to receive measurement data including physiological measurement data of an individual received from a physiological component, and/or data indicative of the response of an individual to a task and/or an interference rendered at a user interface of the apparatus 100 (as described in greater detail below), and/or data indicative of one or more of an amount, concentration, or dose titration, or other treatment regimen of a drug, pharmaceutical agent, biologic, or other medication being or to be administered to an individual.

Non-limiting examples of the computing device include a smartphone, a tablet, a slate, an e-reader, a digital assistant, or any other equivalent device, including any of the mobile communication devices described hereinabove. As an example, the computing device can include a processor unit that is configured to execute an application that includes an analysis module for analyzing the data indicative of the individual's response to the rendered tasks and/or interference.

The example systems, methods, and apparatus can be implemented as a component in a product comprising a computing device that uses computer-implemented adaptive psychophysical procedures to assess human performance or delivers psychological/perceptual therapy.

A non-limiting example characteristic of a type of decision boundary metric that can be computed based on the response profile is the response criterion (a time-point measure), calculated using the standard procedure to calculate response criterion for a signal detection psychophysics assessment. See, e.g., Macmillan and Creelman (2004), "Signal Detection: A Users Guide" $2^{nd}$ edition, Lawrence Erlbaum USA.

In other non-limiting examples, the decision boundary metric may be more than a single quantitative measure but rather a curve defined by quantitative parameters based on which decision boundary metrics can be computed, such as but not limited to an area to one side or the other of the response profile curve. Other non-limiting example types of decision boundary metrics that can be computed to characterize the decision boundary curves for evaluating the time-varying characteristics of the decision process include a distance between the initial bias point (the starting point of the belief accumulation trajectory) and the criterion, a distance to the decision boundary, a "waiting cost" (e.g., the distance from the initial decision boundary and the maximum decision boundary, or the total area of the curve to that point), or the area between the decision boundary and the criterion line (including the area normalized to the response deadline to yield a measure of an "average decision boundary" or an "average criterion").

While examples herein may be described based on computation of a response criterion, other types of decision boundary metrics are applicable.

Figure 3:
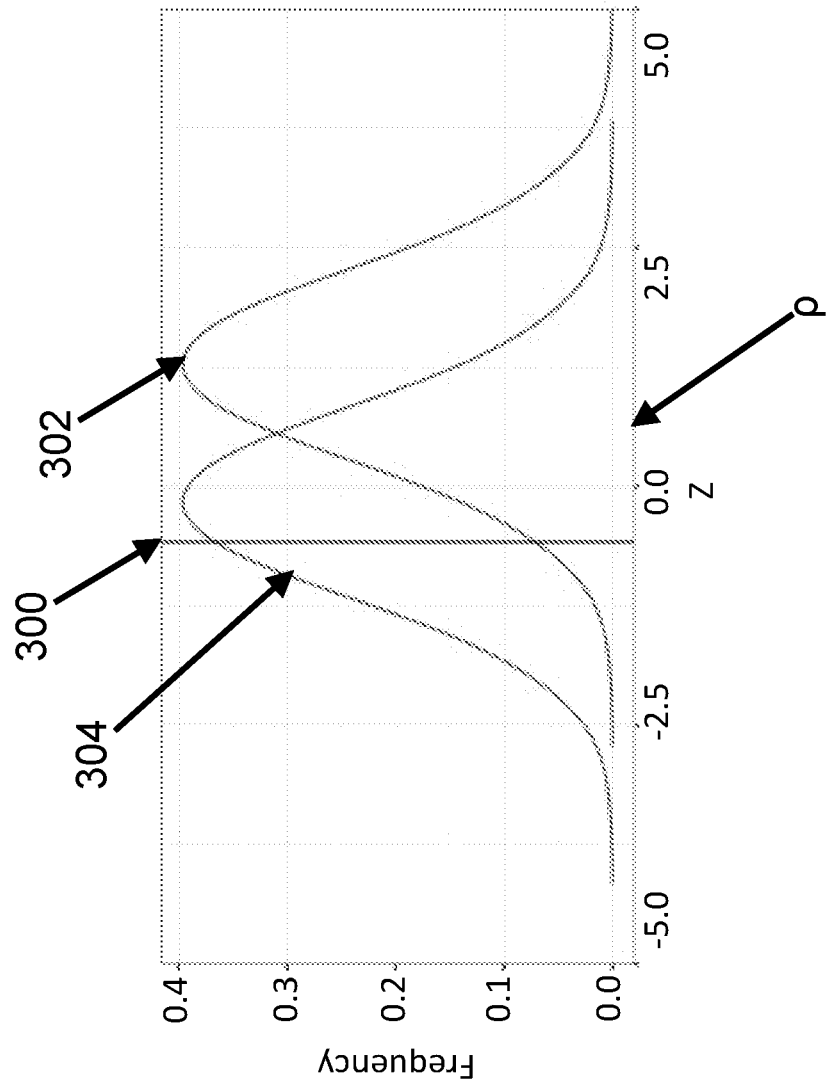
FIG. 3 shows an example plot of the signal and noise distribution curves computed based on an example cognitive test, according to the principles herein.

FIG. 3 shows an example plot of the signal (right curve 302) and noise (left curve 304) distributions of an individual or group psychophysical data, and the computed response criterion, based on data collected from individuals that performed a Test of Variables of Attention (TOVA®) test (The TOVA Company, Los Alamitos, CA). The TOVA® test is an example of a computerized test that can be used by a healthcare professional as an aid in an assessment of an individual's attention deficits and impulsivity, including attention-deficit/hyperactivity disorder (ADHD).

In FIG. 3, the vertical line represents the response criterion 300. The intercept of the criterion line on the X axis (in Z units) can be used to provide an indication of the tendency of an individual to respond 'yes' (further right) or 'no' (further left) from a point of zero bias (ρ). As indicated in FIG. 3, ρ is located on the x-axis where the signal distribution (right curve 302) and the noise distribution (left curve 304) intersect. Response criterion intercepts left of p may indicate an individual's overall tendency to a more impulsive strategy and intercepts right of ρ may indicate an individual's overall tendency to a more conservative strategy. Response criterion intercepts at p indicate a balanced strategy.

The example systems, methods, and apparatus can be configured to implement a further extension of signal detection theory to a time-limited task (as described in greater detail below). The example systems, methods, and apparatus can be configured to extend accumulation of belief information, modeled using a computational model of human decision-making (such as but not limited to a drift-diffusion model (DDM) and/or a Bayesian model), and decision boundaries that reflect different strategies.

Following is a description of a non-limiting example use of a computational model of human decision-making (based on a drift diffusion model). While the drift diffusion model is used as the example, other types of models apply, including a Bayesian model. The drift-diffusion model (DDM) can be applied for systems with two-choice decision making. See, e.g., Ratcliff, R. (1978), "A theory of memory retrieval." *Psychological Review,* 85, 59-108; Ratcliff, R., & Tuerlinckx, F. (2002), "Estimating parameters of the diffusion model: Approaches to dealing with contaminant reaction times and parameter variability," *Psychonomic Bulletin & Review,* 9, 438-481. The diffusion model is based on an assumption that binary decision processes are driven by systematic and random influences.

Figure 4A:
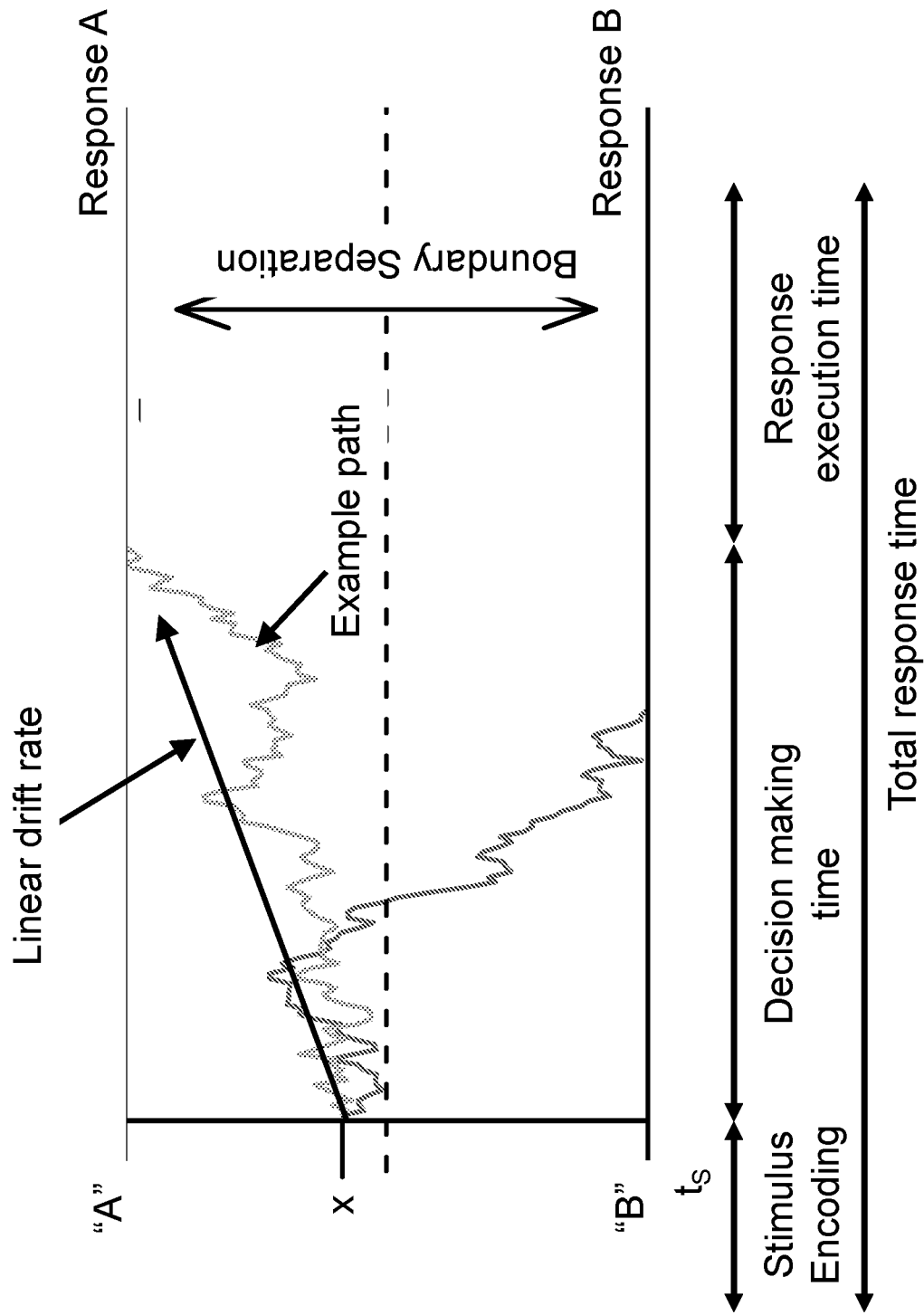
FIG. 4A shows an example graphical depiction of a drift-diffusion model for linear belief accumulation, according to the principles herein.

FIG. 4A shows an example plot of the diffusion model with a stimulus that results in a linear drift rate, showing example paths of the accumulation of belief from a stimulus. It shows the distributions of drift rates across trials for targets (signal) and non-targets (noise). The vertical line is the response criterion. The drift rate on each trial is determined by the distance between the drift criterion and a sample from the drift distribution. The process starts at point x, and moves over time until it reaches the lower threshold at "A" or the upper threshold at "B". The DDM assumes that an individual is accumulating evidence for one or other of the alternative thresholds at each time step, and integrating that evidence to develop a belief, until a decision threshold is reached. Depending on which threshold is reached, different responses (i.e., Response A or Response B) are initiated by the individual. In a psychological application, this means that the decision process is finished and the response system is being activated, in which the individual initiates the corresponding response. As described in non-limiting examples below, this can require a physical action of the individual to actuate a component of the system or apparatus to provide the response (such as but not limited to tapping on the user interface in response to a target). The systematic influences are called the drift rate, and they drive the process in a given direction. The random influences add an erratic fluctuation to the constant path. With a given set of parameters, the model predicts distributions of process durations (i.e., response times) for the two possible outcomes of the process.

FIG. 4A also shows an example drift-diffusion path of the process, illustrating that the path is not straight but rather oscillates between the two boundaries, due to random influences. In a situation in which individuals are required to categorize stimuli, the process describes the ratio of information gathered over time that causes an individual to foster each of the two possible stimulus interpretations. Once belief points with sufficient clarity is reached, the individual initiates a response. In the example of FIG. 4A, processes reaching the upper threshold are indicative of a positive drift rate. In some trials, the random influences can outweigh the drift, and the process terminates at the lower threshold.

Example parameters of the drift diffusion model include quantifiers of the thresholds ("A" or "B"), the starting point (x), the drift rate, and a response time constant (to). The DDM can provide a measure of conservatism, an indication that the process takes more time to reach one threshold and that it will reach the other threshold (opposite to the drift) less frequently. The starting point (x) provides an indicator of bias (reflecting differences in the amount of information that is required before the alternative responses are initiated). If x is closer to "A", an individual requires a smaller (relative) amount of information to develop a belief to execute Response A, as compared with a larger (relative) amount of information that the individual would need to execute Response B. The smaller the distance between the starting point (x) and a threshold, the shorter the process durations would be for the individual to execute the corresponding response. A positive value of drift rate (v) serves as a measure of the mean rate of approach to the upper threshold ("A"). The drift rate indicates the relative amount of information per time unit that the individual absorbs information on a stimulus to develop a belief in order to initiate and execute a response. In an example, comparison of the drift rates computed from data of one individual to data from another can provide a measure of relative perceptual sensitivity of the individuals. In another example, comparison of the drift rates can provide a relative measure of task difficulty. For computation of the response time, the DDM allows for estimating their total duration, and the response time constant (to) indicates the duration of extra-decisional processes. The DDM has been shown to describe accuracy and reaction times in human data for tasks. In the non-limiting example of FIG. 4A, the total response time is computed as a sum of the magnitude of time for stimulus encoding ($t_S$), the time the individual takes for the decision, and the time for response execution.

As compared to the traditional drift diffusion model that is based on stimuli that result in linear drift rates, the example systems, methods, and apparatus according to the principles herein are configured to render stimuli that result in non-linear drift rates, which stimuli are based on tasks and/or interferences that are time-varying and have specified response deadlines. As a result, the example systems, methods, and apparatus according to the principles herein are configured to apply a modified diffusion model (modified DDM) based on these stimuli that result in non-linear drift rates.

Figure 4B:
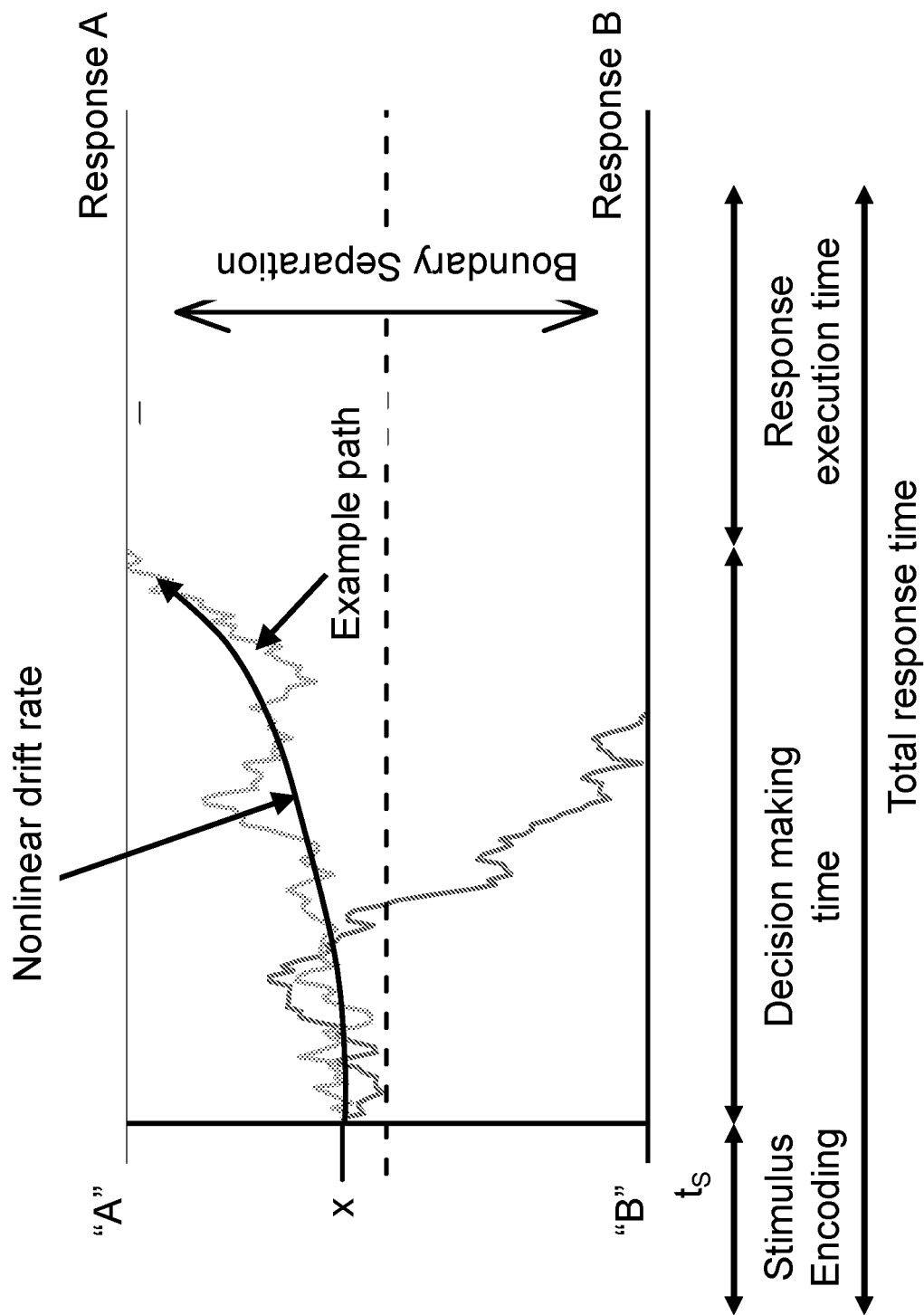
FIG. 4B shows an example graphical depiction of a drift-diffusion model for non-linear belief accumulation, according to the principles herein.

FIG. 4B shows an example plot of a non-linear drift rate in a drift diffusion computation. Example parameters of the modified DDM also include quantifiers of the thresholds ("A" or "B"), the starting point (x), the drift rate, and a response time constant ($t_0$). Based on data collected from user interaction with the example systems, methods, and apparatus herein, the systems, methods, and apparatus are configured to apply the modified DDM with the non-linear drift rates to provide a measure of the conservatism or impulsivity of the strategy employed in the user interaction with the example platforms herein. The example systems, methods, and apparatus are configured to compute a measure of the conservatism or impulsivity of the strategy used by an individual based on the modified DDM model, to provide an indication of the time the process takes for a given individual to reach one threshold and as compared to reaching the other threshold (opposite to the drift). The starting point (x) in FIG. 4B also provides an indicator of bias (reflecting differences in the amount of information that is required before the alternative responses are initiated). For computation of the response time, the DDM allows for estimating their total duration, and the response time constant (to) indicates the duration of extra-decisional processes.

In the example systems, methods, and apparatus according to the principles herein, the non-linear drift rate results from the time-varying nature of the stimuli, including (i) the time-varying feature of portions of the task and/or interference rendered to the user interface for user response (as a result of which the amount of information available for an individual to develop a belief is presented in a temporally non-linear manner), and (ii) the time limit of the response deadlines of the task and/or interference, which can influence an individual's sense of timing to develop a belief in order to initiate a response. In this example as well, a positive value of drift rate (v) serves as a measure of the mean rate of approach to the upper threshold ("A"). The non-linear drift rate indicates the relative amount of information per time unit that the individual absorbs to develop a belief in order to initiate and execute a response. In an example, comparison of the drift rate computed from response data collected from one individual to the drift rate computed from response data collected from another individual can be used to provide a measure of relative perceptual sensitivity of the individuals. In another example, comparison of the drift rate computed from response data collected from a given individual from two or more different interaction sessions can be used to provide a relative measure of task difficulty. For computation of the response time of the individual's responses, the modified DDM also allows for estimating the total duration of the response time, and the response time constant (to) indicates the duration of extra-decisional processes. In the non-limiting example of FIG. 4A, the total response time is computed as a sum of the magnitude of time for stimulus encoding ($t_S$), the time the individual takes for the decision, and the time for response execution.

For the modified DDM, the distance between the thresholds (i.e., between "A" and "B") provides a measure of conservatism—that is, the larger the separation, the more information is collected prior to an individual executing a response. The starting point (x) also provides an estimate of relative conservatism: if the process starts above or below the midpoint between the two thresholds, different amounts of information are required for both responses; that is, a more conservative decision criterion is applied for one response, and a more liberal criterion (i.e., impulsive) for the opposite response. The drift rate (v) indicates the (relative) amount of information gathered per time, denoting either perceptual sensitivity or task difficulty.

Figure 5:
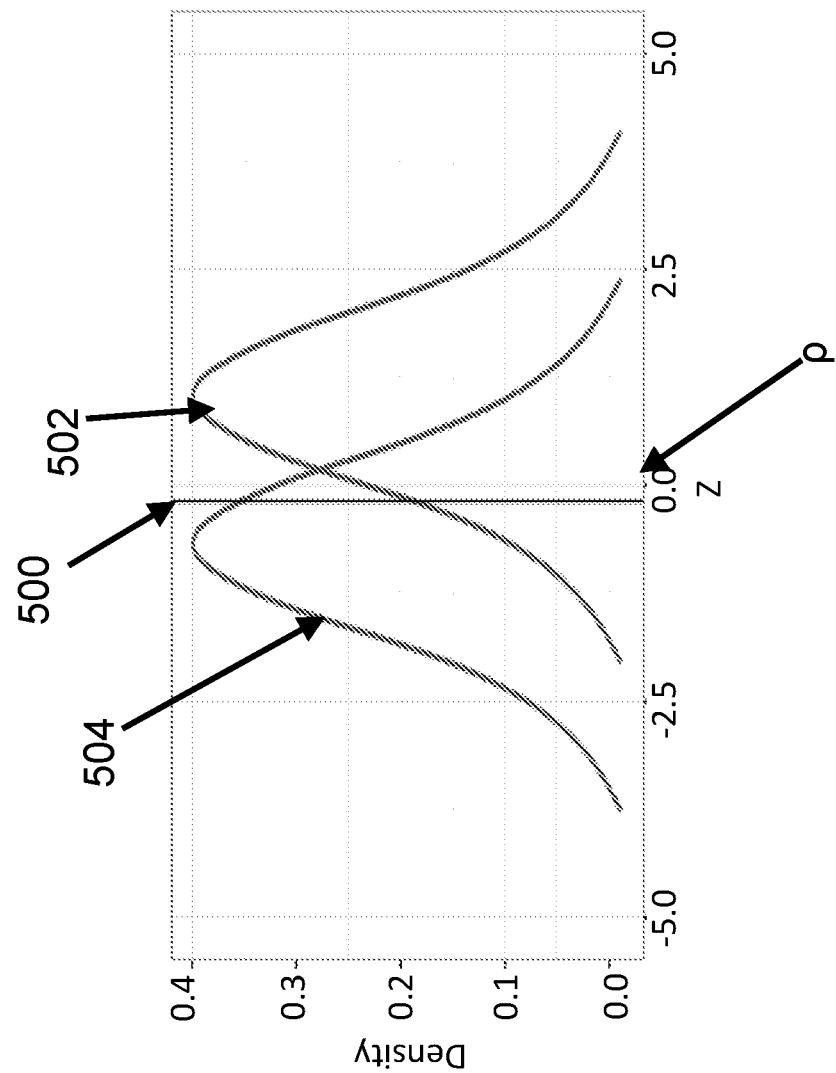
FIG. 5 shows an example plot of the signal (right curve) and noise based on an example cognitive platform, according to the principles herein.

FIG. 5 shows an example plot of the signal (right curve 502) and noise (left curve 504) distributions of an individual or group psychophysical data, and the computed response criterion 500, based on data collected from an individual's responses with the tasks and/or interference rendered at a user interface of a computing device according to the principles herein (as described in greater detail hereinbelow). The intercept of the criterion line on the X axis (in Z units) can be used to provide an indication of the tendency of an individual to respond 'yes' (further right) or 'no' (further left). The response criterion 500 is left of the zero-bias decision point (ρ) and where the signal and noise distributions intersect. In the non-limiting example of FIG. 5, ρ is the location of the zero-bias decision on the decision axis in Z-units, and response criterion values to the left of p indicate an impulsive strategy and response criterion values to the right of p indicate a conservative strategy, with intercepts on the zero-bias point indicating a balanced strategy.

The example systems, methods, and apparatus according to the principles herein can be configured to compute a response criterion based on the detection or classification task(s) described herein that are composed of signal and non-signal response targets (as stimuli), in which a user indicates a response that indicates a feature, or multiple features, are present in a series of sequential presentations of stimuli or simultaneous presentation of stimuli.

The data indicative of the results of the classification of an individual according to the principles herein (including a classifier output) can be transmitted (with the pertinent consent) as a signal to one or more of a medical device, healthcare computing system, or other device, and/or to a medical practitioner, a health practitioner, a physical therapist, a behavioral therapist, a sports medicine practitioner, a pharmacist, or other practitioner, to allow formulation of a course of treatment for the individual or to modify an existing course of treatment, including to determine a change in one or more of an amount, concentration, or dose titration of a drug, biologic or other pharmaceutical agent being or to be administered to the individual and/or to determine an optimal type or combination of drug, biologic or other pharmaceutical agent to be administered to the individual.

The example systems, methods, and apparatus herein provide computerized classifiers, treatment tools, and other tools that can be used by a medical, behavioral, healthcare, or other professional as an aid in an assessment and/or enhancement of an individual's attention, working memory, and goal management. In an example implementation, the example systems, methods, and apparatus herein apply the modified DDM to the collected data to provide measures of conservatism or impulsivity. The example analysis performed using the example systems, methods, and apparatus according to the principles herein can be used to provide measures of attention deficits and impulsivity (including ADHD). The example systems, methods, and apparatus herein provide computerized classifiers, treatment tools, and other tools that can be used as aids in assessment and/or enhancement in other cognitive domains, such as but not limited to attention, memory, motor, reaction, executive function, decision-making, problem-solving, language processing, and comprehension. In some examples, the systems, methods, and apparatus can be used to compute measures for use for cognitive monitoring and/or disease monitoring. In some examples, the systems, methods, and apparatus can be used to compute measures for use for cognitive monitoring and/or disease monitoring during treatment of one or more cognitive conditions and/or diseases and/or executive function disorders.

Figure 6:
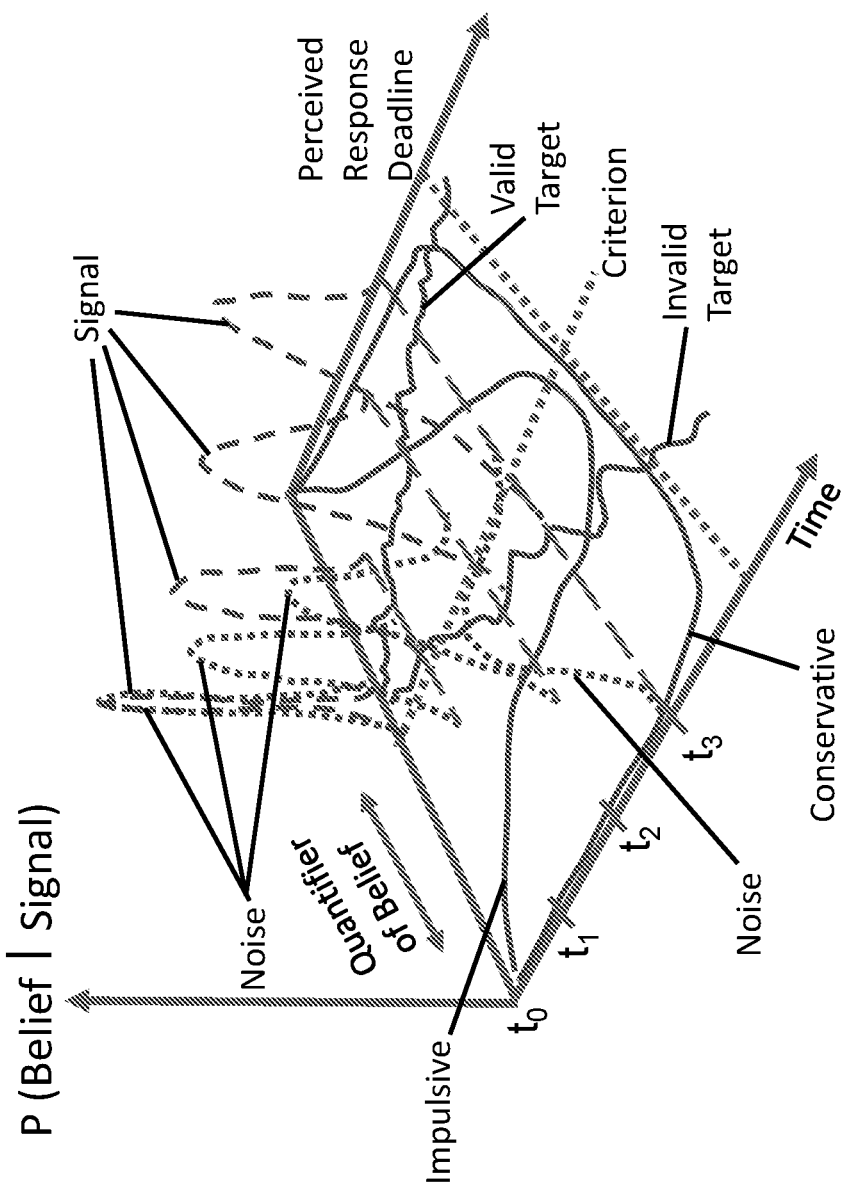
FIG. 6 shows an example plot of the conditional probability of a quantifier of belief given a signal, according to the principles herein.

FIG. 6 shows an example plot of the conditional probability of a quantifier of belief given a signal (P (Belief|Signal)) along the z-axis, Time as the x-axis, and the quantifier of belief is the y-axis. The curve labeled Valid Target and the curve labeled Invalid Target (each lying in the x-y plane) indicate data values quantifying belief trajectories of accumulated (noisy) information over time for a user to develop a strong belief one way or another as to the appropriate response. The four curves labeled Signal and four curves labeled Noise each has a magnitude in the z-direction and are data values of the "signal" distribution and "noise" distribution at different points in time. Each signal curve is paired with a noise, and the pair is time-displaced along the x-axis (at times $t=t_0, t_1, t_2, t_3$). As shown in FIG. 6, each signal-noise curve pair spreads out (i.e., becomes a wider curve as time increases from $t_0$ to $t_3$), to represent the probability of a given degree of belief at a given point in time given a type of signal. In this time-evolving model, the decision is made when the belief trajectory crosses a decision boundary. FIG. 6 also shows example curves that serve as projected decision boundaries for response data values indicative of an impulsive strategy (narrower curve in the x-y plane) and response data values indicative of a conservative strategy (wider curve in the x-y plane). As described herein, the impulsive strategy requires much less extreme belief (i.e., less extreme values of the quantifier of belief) in order to arrive at a decision. As also described herein, the conservative strategy requires much more extreme belief (i.e., more extreme values of the quantifier of belief) in order to arrive at a decision. As the perceived response deadline approaches, these decision boundaries converge on the criterion value described in signal detection theory.

An example system, method or apparatus according to the principles herein can be applied to data values as indicated in accordance with FIG. 6 to compute a classifier to apply to data indicative of a user's responses to the tasks and/or interference rendered at a user interface to determine a measure of whether an individual is employing a more conservative strategy or a more impulsive strategy.

Such an example model, e.g., as described in connection with FIG. 6, enables Bayesian inference of the shape of an individual's decision boundary based on the response times and correctness of a sequence of decisions. In a non-limiting example, a metric can be derived characterizing a degree of impulsiveness of the individual's response strategy based on the area of this decision boundary compared with the area of the "ideal" decision boundary (the response deadline times the full width of the belief axis).

FIGS. 7A-7B show example plots of the curves for values of conservative and impulsive measures from the trial start (t=0) to the perceived response deadline (R-DP). FIG. 7A shows example curves for a two-alternative forced choice (2AFC) task, where an individual is instructed/required to discriminate between two types of stimulus (such as but not limited to targets with differing degrees of a facial expression or other characteristic/feature difference), hence both are ultimately targets as they require an action/response from the individual. FIG. 7B shows example curves for a GO/NO-GO task, where the individual is instructed/required to decide whether a stimulus is a target requiring response/action (based on the instructions) or a non-target requiring inaction/no response (based on the instructions). In some examples herein, the stimuli are designated as GO/NO-GO task (i.e., with instructions to act/give response for a target or not act/give no response). In FIG. 7A, the plot shows the curves versus development of belief (for two types of target stimuli at various time points (t=0, a, b, c, d) as well as the decision boundaries relative to the value of the response criterion for the time-varying stimuli described herein. FIG. 7B shows the differing types of values and shapes of conservative and impulsive measures from the trial start to a response deadline for the traditional GO/NO GO task (target vs. non-target), a pass/fail or yes/no type of test that has two boundary conditions or a binary classification. As shown in FIG. 7B, the curves for the values of the conservative and impulsive measures for the GO/NO GO task does not have a right-side decision boundary because waiting to act/response is not a momentary decision that an individual arrive at, rather it is a process that continues until the end of the trial (or at least until the attention of the individual is allocated elsewhere).

FIGS. 7C-7D show example plots of the formation of belief for linear belief accumulation and non-linear belief accumulation, respectively. In a system with linear belief accumulation, FIG. 7C shows the values of the mean belief for targets ($M_B$(targets)) and mean belief for non-targets ($M_B$(non-targets)) versus the development of belief (for target versus non-target) at various time points (t=0, a, b, c, d) relative to the value of the response criterion. FIG. 7C also shows the target confidence interval and non-target confidence interval for the linear belief accumulation. In a system with non-linear belief accumulation, FIG. 7D shows the values of the mean belief for targets ($M_B$(targets)) and mean belief for non-targets ($M_B$(non-targets)) versus development of belief (for target versus non-target) at various time points (t=0, a, b, c, d) relative to the value of the response criterion for the nonlinear belief accumulation. FIG. 7C also shows the target confidence interval and non-target confidence interval. A traditional GO/NO GO task involves presentation to an individual for a specific period of time of a stimulus without a time-varying aspect, and supports linear accumulation of belief from the information available to the individual for developing belief. By contrast, the example tasks and/or interferences according to the principles herein have at least one time-varying feature (based on their feature dynamics), resulting in nonlinear belief accumulation.

Figure 8A:
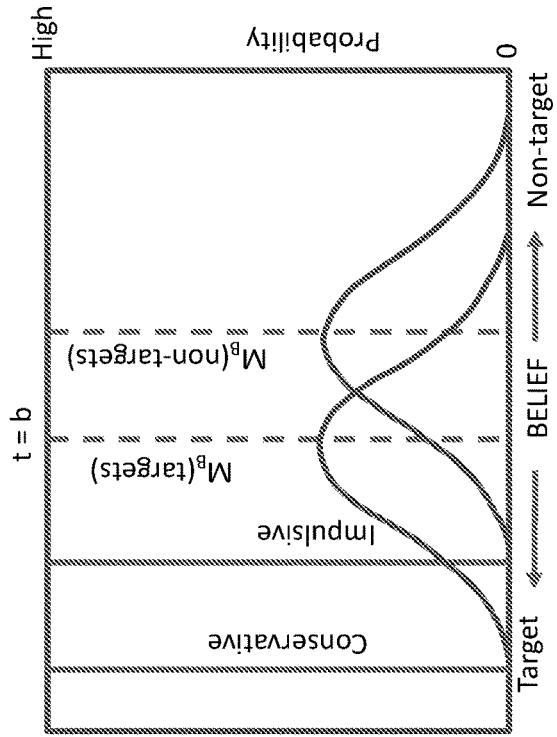
FIGS. 8A-8D show example plots of the probability curves for signal distribution and noise distribution at the time points shown in FIGS. 7A-7D, according to the principles herein.
Figure 8B:
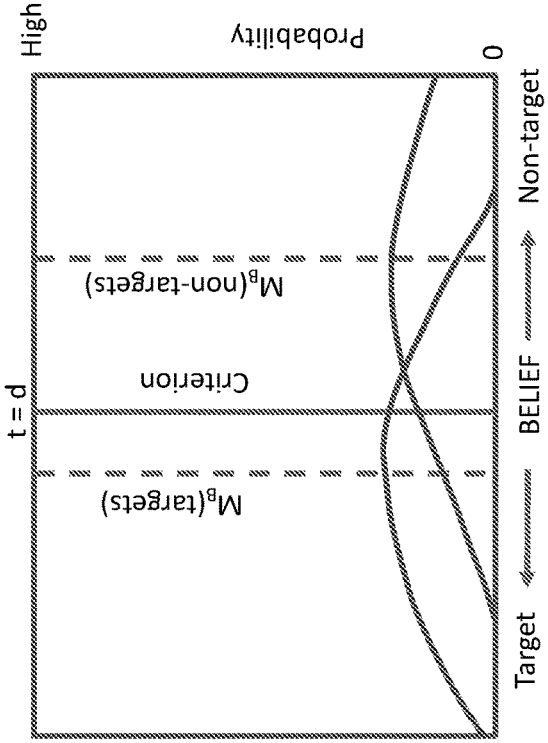
Figure 8C:
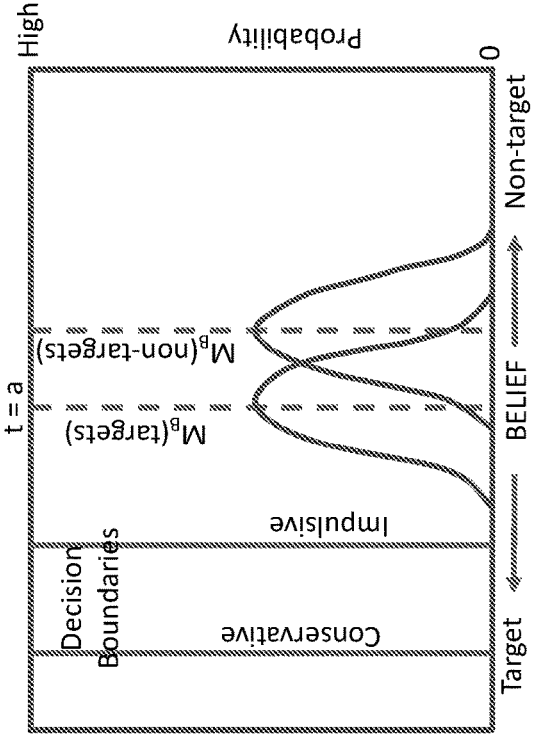
Figure 8D:
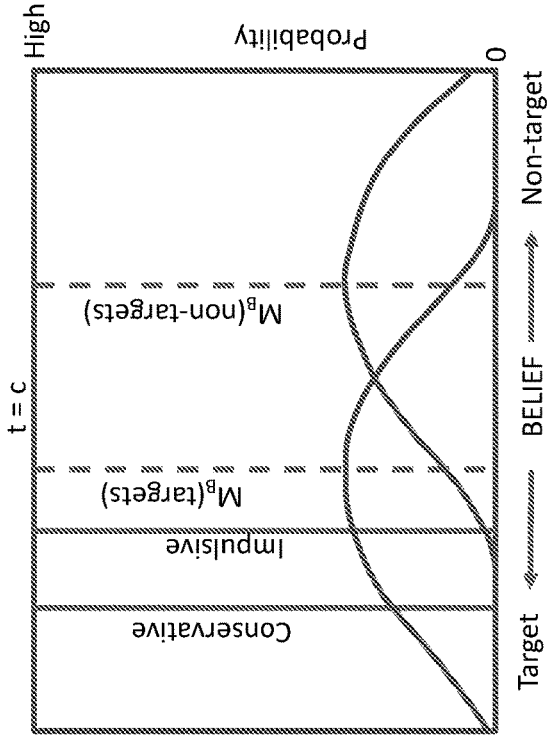

FIGS. 8A-8D show plots of the probability curves for the "signal" distribution and the "noise" distribution at the different points in time (t=a, b, c, d) shown in FIGS. 7A-7D. Each of FIGS. 8A-8D shows a signal curve and a noise curve at differing time-points displaced along the x-axis (similar to the signal and noise curves shown at time-points t=$t_0$, $t_1$, $t_2$, $t_3$ in FIG. 6). As shown in FIGS. 8A-8D, the signal-noise curve pair spreads out (i.e., becomes a wider curve) as time increases from t=a to t=d, representing the probability of a given degree of belief at a given point in time for a given type of signal. In this time-evolving model, the decision is made when the belief trajectory crosses a decision boundary. FIGS. 8A-8D also show the values of the mean belief for targets ($M_B$(targets)) and mean belief for non-targets ($M_B$ (non-targets)) versus the development of belief. In FIG. 8D, the decision boundaries (conservative and impulsive) are converged at the criterion.

An example system, method, and apparatus according to the principles herein can be configured to execute an example response classifier to generate a quantifier of the cognitive skills in an individual. The example response classifier can be built using a machine learning tool, such as but not limited to linear/logistic regression, principal component analysis, generalized linear mixed models, random decision forests, support vector machines, and/or artificial neural networks. In a non-limiting example, classification techniques that may be used to train a classifier using the performance measures of a labeled population of individuals (e.g., individuals with known cognitive disorders, executive function disorder, disease or other cognitive condition). The trained classifier can be applied to measures of the responses of the individual to the tasks and/or interference to classify the individual as to a population label (e.g., cognitive disorder, executive function disorder, disease or other cognitive condition). In an example, machine learning may be implemented using cluster analysis. Each measurement of the cognitive response capabilities of participating individuals can be used as the parameter that groups the individuals to subsets or clusters. For example, the subset or cluster labels may be a diagnosis of a cognitive disorder, cognitive disorder, executive function disorder, disease or other cognitive condition. Using a cluster analysis, similarity metric of each subset and the separation between different subsets can be computed, and these similarity metrics may be applied to data indicative of an individual's responses to a task and/or interference to classify that individual to a subset. In another example, the classifier may be a supervised machine learning tool based on artificial neural networks. In such a case, the performance measures of individuals with known cognitive abilities may be used to train the neural network algorithm to model the complex relationships among the different performance measures. A trained classifier can be applied to the performance/response measures of a given individual to generate a classifier output indicative of the cognitive response capabilities of the individual. Other applicable techniques for generating a classifier include a regression or Monte Carlo technique for projecting cognitive abilities based on his/her cognitive performance. The classifier may be built using other data, including a physiological measure (e.g., EEG) and demographic measures.

In an example implementation, a programmed processing unit is configured to execute processor-executable instructions to render a task with an interference at a user interface. As described in greater detail herein, one or more of the task and the interference can be time-varying and have a response deadline, such that the user interface imposes a limited time period for receiving at least one type of response from the individual interacting with the apparatus or system. The processing unit is configured to control the user interface to measure data indicative of two or more differing types of responses to the task or to the interference. The programmed processing unit is further configured to execute processor-executable instructions to cause the example system or apparatus to receive data indicative of a first response of the individual to the task and a second response of the individual to the interference, analyze at least some portion of the data to compute at least one response profile representative of the performance of the individual, and determine a decision boundary metric (such as but not limited to the response criterion) from the response profile. As described herein, including in connection with FIGS. 4A and 4B, the decision boundary metric (such as but not limited to the response criterion) gives a quantitative measure of a tendency of the individual to provide at least one type of response of the two or more differing types of responses (Response A vs. Response B) to the task or the interference. The programmed processing unit is further configured to execute processor-executable instructions to execute a response classifier based on the computed values of the decision boundary metric (such as but not limited to the response criterion), to generate a classifier output indicative of the cognitive response capabilities of the individual.

In an example, the processing unit further uses the classifier output for one or more of changing one or more of the amount, concentration, or dose titration of the pharmaceutical agent, drug, biologic or other medication, identifying a likelihood of the individual experiencing an adverse event in response to administration of the pharmaceutical agent, drug, biologic or other medication, identifying a change in the individual's cognitive response capabilities, recommending a treatment regimen, or recommending or determining a degree of effectiveness of at least one of a behavioral therapy, counseling, or physical exercise.

In any example herein, the example response classifier can be used as an intelligent proxy for quantifiable assessments of an individual's cognitive abilities. That is, once a response classifier is trained, the classifier output can be used to provide the indication of the cognitive response capabilities of multiple individuals without use of other cognitive or behavioral assessment tests.

Monitoring cognitive deficits allows individuals, and/or medical, healthcare, behavioral, or other professional (with consent) to monitor the status or progression of a cognitive condition, a disease, or an executive function disorder. For example, individuals with Alzheimer's disease may shows mild symptoms initially, but others have more debilitating symptoms. If the status or progression of the cognitive symptoms can be regularly or periodically quantified, it can provide an indication of when a form of pharmaceutical agent or other drug may be administered or to indicate when quality of life might be compromised (such as the need for assisted living). Monitoring cognitive deficits also allows individuals, and/or medical, healthcare, behavioral, or other professional (with consent) to monitor the response of the individual to any treatment or intervention, particularly in cases where the intervention is known to be selectively effective for certain individuals. In an example, a cognitive assessment tool based on the classifiers herein can be an individual patient with attention deficit hyperactivity disorder (ADHD). In another example, the classifiers and other tools herein can be used as a monitor of the presence and/or severity of any cognitive side effects from therapies with known cognitive impact, such as but not limited to chemotherapy, or that involve uncharacterized or poorly characterized pharmacodynamics. In any example herein, the cognitive performance measurements and/or classifier analysis of the data may be performed every 30 minutes, each few hours, daily, two or more times per week, weekly, bi-weekly, each month, or once per year.

In an example, response classifier can be used as an intelligent proxy for quantifiable measures of the degree of conservativeness or impulsivity of the individual.

In an example, the analysis of the data indicative of the first response and/or the second response generates a first response profile that is an impulsive response profile or a conservative response profile.

In a non-limiting example, the task and the interference can be rendered at the user interface such that the individual is required to provide the first response and the second response within a limited period of time. In an example, the individual is required to provide the first response and the second response substantially simultaneously.

In the example herein, "substantially simultaneously" means tasks are rendered, or response measurements are performed, within less than about 5 milliseconds of each other, or within about 10 milliseconds, about 20 milliseconds, about 50 milliseconds, about 75 milliseconds, about 100 milliseconds, or about 150 milliseconds or less, about 200 milliseconds or less, about 250 milliseconds or less, of each other. In any example herein, "substantially simultaneously" is a period of time less than the average human reaction time. In another example, two tasks may be substantially simultaneous if the individual switches between the two tasks within a pre-set amount of time. The set amount of time for switching considered "substantially simultaneously" can be about 1 tenth of a second, 1 second, about 5 seconds, about 10 seconds, about 30 seconds, or greater.

In a non-limiting example, the classifier output can be indicative of the degree of impulsiveness or conservativeness of the individual's cognitive response capabilities.

In an example, the processing unit executes further instructions including applying at least one adaptive procedure to modify the task and/or the interference, such that analysis of the data indicative of the first response and/or the second response indicates a modification of the first response profile.

In an example, the at least one response profile changes from an impulsive response profile to a conservative response profile based on received data collected from measurement of the first response and/or the second response to the modified task and/or the modified.

In an example, the task or the interference includes a response-deadline procedure having the response-deadline; and wherein the at least one adaptive procedure modifies the response-deadline to modify a performance characteristics of the individual to an impulsive response profile or a conservative response profile.

In an example, the processing unit controls the user interface to modify a temporal length of the response window associated with the response-deadline procedure.

In an example, the processing unit controls the user interface to modify a time-varying characteristics of an aspect of the task or the interference rendered to the user interface.

As described in connection with FIGS. 4A and 4B, the time-varying characteristics of the task and/or interference results in the time-varying availability of information about the target, such that that a linear drift-rate is no longer sufficient to capture development of belief over time (rather, requiring a nonlinear drift rate). A time-varying characteristic can be a feature such as, but not limited to, color, shape, type of creature, facial expression, or other feature that an individual requires in order to discriminate between a target and a non-target, resulting in differing time-characteristics of availability. The trial-by-trial adjustment of the response window length also can be a time-varying characteristic that alters the individual's perception of where the decision criteria needs to be in order to respond successfully to a task and/or an interference. Another time-varying characteristic that can be modified is the degree that an interference interferes with a parallel task which can introduce interruptions in belief accumulation and/or response selection and execution.

In an example, modifying the time-varying characteristics of an aspect of the task or the interference includes adjusting a temporal length of the rendering of the task or interference at the user interface between two or more sessions of interactions of the individual.

In an example, the time-varying characteristics is one or more of a speed of an object, a rate of change of a facial expression, a direction of trajectory of an object, a change of orientation of an object, at least one color of an object, a type of an object, or a size of an object.

In an example, the change in type of object is effected using morphing from a first type of object to a second type of object or rendering a blendshape as a proportionate combination of the first type of object and the second type of object.

In a non-limiting example, the processing unit can be configured to render a user interface or cause another component to execute least one element for indicating a reward to the individual for a degree of success in interacting with a task and/or interference, or another feature or other element of a system or apparatus. A reward computer element can be a computer generated feature that is delivered to a user to promote user satisfaction with the example system, method or apparatus, and as a result, increase positive user interaction and hence enjoyment of the experience of the individual.

In an example, the processing unit further computes as the classifier output parameters indicative of one or more of a bias sensitivity derived from the data indicative of the first response and the second response, a non-decision time sensitivity to parallel tasks, a belief accumulation sensitivity to parallel task demands, a reward rate sensitivity, or a response window estimation efficiency. Bias sensitivity can be a measure of how sensitive an individual is to certain of the tasks based on their bias (tendency to one type of response versus another (e.g., Response A vs. Response B)). Non-decision time sensitivity to parallel tasks can be a measure of how much the interference interferes with the individual's performance of the primary task. Belief accumulation sensitivity to parallel task demands can be a measure of the rate of the individual to develop/accumulate belief for responding to the interference during the individual's performance of the primary task. Reward rate sensitivity can be used to measure how an individual's response changes based on the temporal length of the response deadline window. When near the end of a response deadline window (e.g., as individual sees interference about to move off the field of view), the individual realizes that he is running out of time to make a decision. This measures how the individual's responses change accordingly. Response window estimation efficiency is explained as follows. When the individual is making a decision to act/respond or not act/no response, the decision needs to be based on when the individual thinks his time to respond is running out. For a varying window, the individual will not be able to measure that window perfectly, but with enough trials/session, based the response data, it may be possible to infer how good the individual is at making that estimation based on the time-varying aspect (e.g., trajectory) of the objects in the task or interference.

An example system, method, and apparatus according to the principles herein can be configured to train a classifier model of a measure of the cognitive capabilities of individuals based on feedback data from the output of the computational model of human decision-making for individuals that are previously classified as to the measure of cognitive abilities of interest. For example, the response classifier can be trained using a plurality of training datasets, where each training dataset is associated with a previously classified individual from a group of individuals. Each of the training dataset includes data indicative of the first response of the classified individual to the task and data indicative of the second response of the classified individual to the interference, based on the classified individual's interaction with an example apparatus, system, or computing device described herein. The example response classifier also can take as input data indicative of the performance of the classified individual at a cognitive test, and/or a behavioral test, and/or data indicative of a diagnosis of a status or progression of a cognitive condition, a disease, or a disorder (including an executive function disorder) of the classified individual.

In any example herein, the at least one processing unit can be programmed to cause an actuating component of the apparatus (including the cognitive platform) to effect auditory, tactile, or vibrational computerized elements to effect the stimulus or other interaction with the individual. In a non-limiting example, the at least one processing unit can be programmed to cause a component of the cognitive platform to receive data indicative of at least one response from the individual based on the user interaction with the task and/or interference, including responses provided using an input device. In an example where at least one graphical user interface is rendered to present the computerized stimulus to the individual, the at least one processing unit can be programmed to cause the graphical user interface to receive the data indicative of at least one response from the individual.

In any example herein, the data indicative of the response of the individual to a task and/or an interference can be measured using at least one sensor device contained in and/or coupled to an example system or apparatus herein, such as but not limited to a gyroscope, an accelerometer, a motion sensor, a position sensor, a pressure sensor, an optical sensor, an auditory sensor, a vibrational sensor, a video camera, a pressure-sensitive surface, a touch-sensitive surface, or other type of sensor. In other examples, the data indicative of the response of the individual to the task and/or an interference can be measured using other types of sensor devices, including a video camera, a microphone, joystick, keyboard, a mouse, a treadmill, elliptical, bicycle, steppers, or a gaming system (including a Wii®, a Playstation®, or an Xbox® or other gaming system). The data can be generated based on physical actions of the individual that are detected and/or measured using the at least one sensor device, as the individual executed a response to the stimuli presented with the task and/or interference.

The user may respond to tasks by interacting with the computer device. In an example, the user may execute a response using a keyboard for alpha-numeric or directional inputs; a mouse for go/no go clicking, screen location inputs, and movement inputs; a joystick for movement inputs, screen location inputs, and clicking inputs; a microphone for audio inputs; a camera for still or motion optical inputs; sensors such as accelerometer and gyroscopes for device movement inputs; among others. Non-limiting example inputs for a game system include but are not limited to a game controller for navigation and clicking inputs, a game controller with accelerometer and gyroscope inputs, and a camera for motion optical inputs. Example inputs for a mobile device or tablet include a touch screen for screen location information inputs, virtual keyboard alpha-numeric inputs, go/no go tapping inputs, and touch screen movement inputs; accelerometer and gyroscope motion inputs; a microphone for audio inputs; and a camera for still or motion optical inputs, among others. In other examples, data indicative of the individual's response can include physiological sensors/measures to incorporate inputs from the user's physical state, such as but not limited to electroencephalogram (EEG), magnetoencephalography (MEG), heart rate, heart rate variability, blood pressure, weight, eye movements, pupil dilation, electrodermal responses such as the galvanic skin response, blood glucose level, respiratory rate, and blood oxygenation.

In any example herein, the individual may be instructed to provide a response via a physical action of clicking a button and/or moving a cursor to a correct location on a screen, head movement, finger or hand movement, vocal response, eye movement, or other action of the individual.

As a non-limiting example, an individual's response to a task or interference rendered at the user interface that requires a user to navigate a course or environment or perform other visuo-motor activity may require the individual to make movements (such as but not limited to steering) that are detected and/or measured using at least one type of the sensor device. The data from the detection or measurement provides the response to the data indicative of the response.

As a non-limiting example, an individual's response to a task or interference rendered at the user interface that requires a user to discriminate between a target and a non-target may require the individual to make movements (such as but not limited to tapping or other spatially or temporally discriminating indication) that are detected and/or measured using at least one type of the sensor device. The data that is collected by a component of the system or apparatus based on the detection or other measurement of the individual's movements (such as but not limited to at least one sensor or other device or component described herein) provides the data indicative of the individual's responses.

The example system, method, and apparatus can be configured to apply the classifier model, using computational techniques and machine learning tools, such as but not limited to linear/logistic regression, principal component analysis, generalized linear mixed models, random decision forests, support vector machines, or artificial neural networks, to the data indicative of the individual's response to the tasks and/or interference, and/or data from one or more physiological measures, to create composite variables or profiles that are more sensitive than each measurement alone for generating a classifier output indicative of the cognitive response capabilities of the individual. In an example, the classifier output can be configured for other indications such as but not limited to detecting an indication of a disease, disorder or cognitive condition, or assessing cognitive health.

The example response classifiers herein can be trained to be applied to data collected from interaction sessions of individuals with the cognitive platform to provide the output. In a non-limiting example, the classifier model can be used to generate a standards table, which can be applied to the data collected from the individual's response to task and/or interference to classify the individual's cognitive response capabilities.

Non-limiting examples of assessment of cognitive abilities include assessment scales or surveys such as the Mini Mental State Exam, CANTAB cognitive battery, Test of Variables of Attention (TOVA), Repeatable Battery for the Assessment of Neuropsychological Status, Clinical Global Impression scales relevant to specific conditions, Clinician's Interview-Based Impression of Change, Severe Impairment Battery, Alzheimer's Disease Assessment Scale, Positive and Negative Syndrome Scale, Schizophrenia Cognition Rating Scale, Conners Adult ADHD Rating Scales, Hamilton Rating Scale for Depression, Hamilton Anxiety Scale, Montgomery-Asberg Depressing Rating scale, Young Mania Rating Scale, Children's Depression Rating Scale, Penn State Worry Questionnaire, Hospital Anxiety and Depression Scale, Aberrant Behavior Checklist, Activities for Daily Living scales, ADHD self-report scale, Positive and Negative Affect Schedule, Depression Anxiety Stress Scales, Quick Inventory of Depressive Symptomatology, and PTSD Checklist.

In other examples, the assessment may test specific functions of a range of cognitions in cognitive or behavioral studies, including tests for perceptive abilities, reaction and other motor functions, visual acuity, long-term memory, working memory, short-term memory, logic, and decision-making, and other specific example measurements, including but are not limited to TOVA, MOT (motion-object tracking), SART, CDT (Change detection task), UFOV (useful Field of view), Filter task, WAIS digit symbol, Troop, Simon task, Attentional Blink, N-back task, PRP task, task-switching test, and Flanker task.

In non-limiting examples, the example systems, methods, and apparatus according to the principles described herein can be applicable to many different types of neuropsychological conditions, such as but not limited to dementia, Parkinson's disease, cerebral amyloid angiopathy, familial amyloid neuropathy, Huntington's disease, or other neurodegenerative condition, autism spectrum disorder (ASD), presence of the 16p11.2 duplication, and/or an executive function disorder, such as but not limited to attention deficit hyperactivity disorder (ADHD), sensory-processing disorder (SPD), mild cognitive impairment (MCI), Alzheimer's disease, multiple-sclerosis, schizophrenia, major depressive disorder (MDD), or anxiety.

The instant disclosure is directed to computer-implemented devices formed as example cognitive platforms configured to implement software and/or other processor-executable instructions for the purpose of measuring data indicative of a user's performance at one or more tasks, to provide a user performance metric. The example performance metric can be used to derive an assessment of a user's cognitive abilities and/or to measure a user's response to a cognitive treatment, and/or to provide data or other quantitative indicia of a user's condition (including physiological condition and/or cognitive condition). Non-limiting example cognitive platforms according to the principles herein can be configured to classify an individual as to a neuropsychological condition, autism spectrum disorder (ASD), presence of the 16p11.2 duplication, and/or an executive function disorder, and/or potential efficacy of use of the cognitive platform when the individual is being administered (or about to be administered) a drug, biologic or other pharmaceutical agent, based on the data collected from the individual's interaction with the cognitive platform and/or metrics computed based on the analysis (and associated computations) of that data. Yet other non-limiting example cognitive platforms according to the principles herein can be configured to classify an individual as to likelihood of onset and/or stage of progression of a neuropsychological condition, including as to a neurodegenerative condition, based on the data collected from the individual's interaction with the cognitive platform and/or metrics computed based on the analysis (and associated computations) of that data. The neurodegenerative condition can be, but is not limited to, Alzheimer's disease, dementia, Parkinson's disease, cerebral amyloid angiopathy, familial amyloid neuropathy, or Huntington's disease.

Any classification of an individual as to likelihood of onset and/or stage of progression of a neurodegenerative condition according to the principles herein can be transmitted as a signal to a medical device, healthcare computing system, or other device, and/or to a medical practitioner, a health practitioner, a physical therapist, a behavioral therapist, a sports medicine practitioner, a pharmacist, or other practitioner, to allow formulation of a course of treatment for the individual or to modify an existing course of treatment, including to determine a change in dosage of a drug, biologic or other pharmaceutical agent to the individual or to determine an optimal type or combination of drug, biologic or other pharmaceutical agent to the individual.

In any example herein, the cognitive platform can be configured as any combination of a medical device platform, a monitoring device platform, a screening device platform, or other device platform.

The instant disclosure is also directed to example systems that include cognitive platforms that are configured for coupling with one or more physiological or monitoring component and/or cognitive testing component. In some examples, the systems include cognitive platforms that are integrated with the one or more other physiological or monitoring component and/or cognitive testing component. In other examples, the systems include cognitive platforms that are separately housed from and configured for communicating with the one or more physiological or monitoring component and/or cognitive testing component, to receive data indicative of measurements made using such one or more components.

In an example system, method, and apparatus herein, the task or the interference can include a response-deadline procedure having the response-deadline; where the at least one adaptive procedure modifies the response-deadline to modify a performance characteristics of the individual to an impulsive response profile or a conservative response profile.

In an example system, method, and apparatus herein, the processing unit can be programmed to control the user interface to modify a temporal length of the response window associated with the response-deadline procedure.

In an example system, method, and apparatus herein, the processing unit can be configured to control the user interface to modify a time-varying characteristics of an aspect of the task or the interference rendered to the user interface. For example, modifying the time-varying characteristics of an aspect of the task or the interference can include adjusting a temporal length of the rendering of the task or interference at the user interface between two or more sessions of interactions of the individual. As another example, the time-varying characteristics is one or more of a speed of an object, a rate of change of a facial expression, a direction of trajectory of an object, a change of orientation of an object, at least one color of an object, a type of an object, or a size of an object.

In an example system, method, and apparatus herein, the change in type of object is effected using morphing from a first type of object to a second type of object or rendering a blendshape as a proportionate combination of the first type of object and the second type of object.

In an example system, method, and apparatus herein, the processing unit can be further programmed to compute as the classifier output parameters indicative of one or more of a bias sensitivity derived from the data indicative of the first response and the second response, a non-decision time sensitivity to parallel tasks, a belief accumulation sensitivity to parallel task demands, a reward rate sensitivity, or a response window estimation efficiency.

In an example system, method, and apparatus herein, the processing unit can be further programmed to control the user interface to render the task as a continuous visuo-motor tracking task.

In an example system, method, and apparatus herein, the processing unit controls the user interface to render the interference as a target discrimination task.

As used herein, a target discrimination task may also be referred to as a perceptual reaction task, in which the individual is instructed to perform a two-feature reaction task including target stimuli and non-target stimuli through a specified form of response. As a non-limiting example, that specified type of response can be for the individual to make a specified physical action in response to a target stimulus (e.g., move or change the orientation of a device, tap on a sensor-coupled surface such as a screen, move relative to an optical sensor, make a sound, or other physical action that activates a sensor device) and refrain from making such specified physical action in response to a non-target stimulus.

In a non-limiting example, the individual is required to perform a visuomotor task (as a primary task) with a target discrimination task as an interference (secondary task). To effect the visuomotor task, a programmed processing unit renders visual stimuli that require fine motor movement as reaction of the individual to the stimuli. In some examples, the visuomotor task is a continuous visuomotor task. The processing unit is programmed to alter the visual stimuli and recording data indicative of the motor movements of the individual over time (e.g., at regular intervals including 1, 5, 10, or 30 times per second). Example stimuli rendered using the programmed processing unit for a visuomotor task requiring fine motor movement may be a visual presentation of a path that an avatar is required to remain within. The programmed processing unit may render the path with certain types of obstacles that the individual is either required to avoid or to navigate towards. In an example, the fine motor movements effect by the individual, such as but not limited to tilting or rotating a device, are measured using an accelerometer and/or a gyroscope (e.g., to steer or otherwise guide the avatar on the path while avoiding or crossing the obstacles as specified). The target discrimination task (serving as the interference), can be based on targets and non-targets that differ in shape and/or color.

In some examples, the task and/or interference can be a visuomotor task, a target discrimination task, and/or a memory task.

Within the context of a computer-implemented adaptive response-deadline procedure, the response-deadline can be adjusted between trials or blocks of trials to manipulate the individual's performance characteristics towards certain goals. A common goal is driving the individual's average response accuracy towards a certain value by controlling the response deadline.

Measurements at different response deadlines can provide different data as to the shape and/or area of their decision boundary, so the computer-implemented adaptive procedure can inform the calculation of the impulsiveness strategy metric.

In a non-limiting example, the metric from signal detection theory representing cognitive function may be the hit rate from a target discrimination task. In that context, hit rate may be defined as the number of correct responses to a target stimuli divided by the total number of target stimuli presented, or the false alarm rate (e.g., the number of responses to a distractor stimuli divided by the number of distractor stimuli presented), the miss rate (e.g., the number of non-responses to a target stimuli divided by the number of incorrect responses, including the nonresponses to a target stimuli added to the number of responses to a distractor stimuli), the correct response rate (the proportion of correct responses not containing signal). In an example, the correct response rate may be calculated as the number of non-responses to the distractor stimuli divided by the number of non-responses to the distractor stimuli plus the number of responses to the target stimuli.

An example system, method, and apparatus according to the principles herein can be configured to apply adaptive performance procedures to modify measures of performance to a specific stimulus intensity. The procedure can be adapted based on a percent correct (PC) or a D-Prime (d') signal detection metric of sensitivity to a target. In an example system, the value of percent correct (i.e., percent of correct responses of the individual to a task) or D-prime may be used in the adaptive algorithms as the basis for adapting the stimulus level of tasks and/or interferences rendered at the user interface for user interaction from one trial to another. However, the inventors have unexpectedly found that an adaptive procedure based on a computational model of human decision-making (such as but not limited to the modified DDM), classifiers built from outputs of such models, and the analysis described herein based on the output of the computational model, can be more quantitatively informative on individual differences or on changes in sensitivity to a specific stimulus level. The decision boundary metric (such as but not limited to the response criterion) provides a flexible tool for determining a tendency of an individual to provide a particular type of response. Accordingly, an adaptation procedure based on decision boundary metric (such as but not limited to the response criterion) measurements at the individual or group level become a desirable source of information about impulsive or conservative response strategies at the time of measurement and also as a quantifier of the changes in performance at the individual or group level over time with repeated measurements.

Executive function training, such as that delivered by the example systems, methods, and apparatus described herein can be configured to apply an adaptive algorithm to modify the stimulus levels between trials, to move a user's response strategy as indicated by their measured criterion to a more conservative or impulsive strategy, depending on the needs or preference of the individual or based on the clinical population receiving the treatment.

The example systems, methods, and apparatus described herein can be configured to apply an adaptive algorithm that is adapted based on the computed decision boundary metric (such as but not limited to the response criterion) as described herein to modify the difficulty levels of the tasks and/or interference rendered at the user interface for user interaction from one trial to another.

FIG. 9 shows an example plot representing a stimulus that is adapted on a single property that has a range of possible intensities. FIG. 9 shows a projected two-dimensional (2D) representation of a three-dimensional (3D) joint distribution composed of a stimuli in which the observer attends to multiple features at a time. FIG. 9 shows one of several techniques to measure the criterion of multi-dimensional stimulus. In this example, a combined PC of 80% or d' of 1.81 for multi-dimensional stimuli is located on the point labeled 900. The band 902 represents the possible d' resulting from the range of possible hit and false-alarm rates in a system or apparatus that adapts the tasks and/or interference based on an adaptive performance procedure where performance is directed to PC=80% correct. In FIG. 9, the center noise distribution is centered at (0,0), which is a simplification to constrain the band 902 of possible d' locations, but in practice the noise distribution center can be located anywhere on the axes, as long as the distance between the noise and signal distributions are connected by a vector the length of the d' value. Multi-dimensional criterions can be estimated for individuals or groups of individuals, and produce an estimate of conservative or impulsive response strategies at the time of measurement or as a response to training using the computing device. Adapting the tasks and/or interference based on the output from the response classifiers herein can provide for greater flexibility than adaptation based on the percent correct.

In an example, the task and/or interference can be modified based on an iterative estimation of metrics by tracking current estimates and selecting the features, trajectory, and response window of the targeting task, and level/type of parallel task interference for the next trial in order to maximize information the trial can provide.

In some examples, the task and/or interference are adaptive tasks. The task and/or interference can be adapted or modified in difficulty level based on the decision boundary metric (such as but not limited to the response criterion), as described hereinabove. Such difficulty adaption may be used to determine the ability of the participant.

In an example, the difficulty of the task adapts with every stimuli that is presented, which could occur more often than once at regular time intervals (e.g., every 5 seconds, every 10 seconds, every 20 seconds or other regular schedule).

In another example, the difficulty of a continuous task can be adapted on a set schedule, such as but not limited to every 30 seconds, 10 seconds, 1 second, 2 times per second, or 30 times per second.

In an example, the length of time of a trial depends on the number of iterations of rendering (of the tasks/interference) and receiving (of the individual's responses) and can vary in time. In an example, a trial can be on the order of about 500 milliseconds, about 1 second (s), about 10 s, about 20 s, about 25 s, about 30 s, about 45 s, about 60 s, about 2 minutes, about 3 minutes, about 4 minutes, about 5 minutes, or greater. Each trial may have a pre-set length or may be dynamically set by the processing unit (e.g., dependent on an individual's performance level or a requirement of the adapting from one level to another).

In an example, the task and/or interference can be modified based on targeting changes in one or more specific metrics by selecting features, trajectory, and response window of the targeting task, and level/type of parallel task interference to progressively require improvements in those metrics in order for the apparatus to indicate to an individual that they have successfully performed the task. This could include specific reinforcement, including explicit messaging, to guide the individual to modify performance according to the desired goals.

In an example, the task and/or interference can be modified based on a comparison of an individual's performance with normative data or a computer model or taking user input (the individual performing the task/interference or another individual such as a clinician) to select a set of metrics to target for changing in a specific order, and iteratively modifying this procedure based on the subject's response to treatment. This could include feedback to the individual performing the task/interference or another individual to serve as notification of changes to the procedure, potentially enabling them to approve or modify these changes before they take effect.

In various examples, the difficulty level may be kept constant or may be varied over at least a portion of a session in an adaptive implementation, where the adaptive task (primary task or secondary task) increases or decreases in difficulty based on the decision boundary metric (such as but not limited to the response criterion).

An example system, method, and apparatus according to the principles herein can be configured to enhance the cognitive skills in an individual. In an example implementation, a programmed processing unit is configured to execute processor-executable instructions to render a task with an interference at a user interface. As described in greater detail herein, one or more of the task and the interference can be time-varying and have a response deadline, such that the user interface imposes a limited time period for receiving at least one type of response from the individual interacting with the apparatus or system. The processing unit is configured to control the user interface to measure data indicative of two or more differing types of responses to the task or to the interference. The programmed processing unit is further configured to execute processor-executable instructions to cause the example system or apparatus to receive data indicative of a first response of the individual to the task and a second response of the individual to the interference, analyze at least some portion of the data to compute at least one response profile representative of the performance of the individual, and determine a decision boundary metric (such as but not limited to the response criterion) from the response profile. As described herein, including in connection with FIGS. 4A and 4B, the decision boundary metric (such as but not limited to the response criterion) gives a quantitative measure of a tendency of the individual to provide at least one type of response of the two or more differing types of responses (Response A vs. Response B) to the task or the interference. The programmed processing unit is further configured to execute processor-executable instructions to adapt the task and/or the interference to derive a modification in the computed decision boundary metric (such as but not limited to the response criterion) such that the first response and/or the second response is modified, thereby indicating a modification of the cognitive response capabilities of the individual.

In an example, the indication of the modification of the cognitive response capabilities can be based on observation of a change in a measure of a degree of impulsiveness or conservativeness of the individual's cognitive response capabilities.

In an example, the indication of the modification of the cognitive response capabilities can include a change in a measure of one or more of sustained attention, selective attention, attention deficit, impulsivity, inhibition, perceptive abilities, reaction and other motor functions, visual acuity, long-term memory, working memory, short-term memory, logic, and decision-making.

In an example, adapting the task and/or interference based on the first decision boundary metric (such as but not limited to the response criterion) includes one or more of modifying the temporal length of the response window, modifying a type of reward or rate of presentation of rewards to the individual, and modifying a time-varying characteristic of the task and/or interference.

In an example, modifying the time-varying characteristics of an aspect of the task or the interference can include adjusting a temporal length of the rendering of the task or interference at the user interface between two or more sessions of interactions of the individual.

In an example, the time-varying characteristics can include one or more of a speed of an object, a rate of change of a facial expression, a direction of trajectory of an object, a change of orientation of an object, at least one color of an object, a type of an object, or a size of an object, or modifying a sequence or balance of rendering of targets versus non-targets at the user interface.

In an example, the change in type of object is effected using morphing from a first type of object to a second type of object or rendering a blendshape as a proportionate combination of the first type of object and the second type of object.

Designing the computer-implemented adaptive procedure using a goal of explicitly measuring the shape and/or area of the decision boundary, the response deadlines can be adjusted to points where measurements produce maximal information of use for defining this boundary. These optimal deadlines may be determined using an information theoretic approach to minimize the expected information entropy.

Example systems, methods and apparatus according to the principles herein can be implemented using a programmed computing device including at least one processing unit, to determine a potential biomarker for clinical populations.

Example systems, methods and apparatus according to the principles herein can be implemented using a programmed computing device including at least one processing unit as a metric for individuals and groups to assess tendency for impulsive and/or conservative response strategies.

Example systems, methods and apparatus according to the principles herein can be implemented using a programmed computing device including at least one processing unit to improve computer-implemented adaptive procedures to compensate for impulsive or conservative response profiles.

Example systems, methods and apparatus according to the principles herein can be implemented using a programmed computing device including at least one processing unit to measure change in response profile in individuals or groups after use of an intervention.

Example systems, methods and apparatus according to the principles herein can be implemented using a programmed computing device including at least one processing unit to apply the example metrics herein, to add another measurable characteristic of individual or group data that can be implemented for greater measurement of psychophysical-threshold accuracy and assessment of response profile to computer-implemented adaptive psychophysical procedures.

Example systems, methods and apparatus according to the principles herein can be implemented using a programmed computing device including at least one processing unit to apply the example metrics herein to add a new dimension to available data that can be used to increase the amount of information harvested from psychophysical testing.

An example system, method, and apparatus according to the principles herein can be configured to enhance the cognitive skills in an individual. In an example implementation, a programmed processing unit is configured to execute processor-executable instructions to render a task with an interference at a user interface. As described in greater detail herein, one or more of the task and the interference can be time-varying and have a response deadline, such that the user interface imposes a limited time period for receiving at least one type of response from the individual interacting with the apparatus or system. The processing unit is configured to control the user interface to measure data indicative of two or more differing types of responses to the task or to the interference. The programmed processing unit is further configured to execute processor-executable instructions to cause the example system or apparatus to receive data indicative of a first response of the individual to the task and a second response of the individual to the interference (from a first session), analyze at least some portion of the data to compute a first response profile representative of the first performance of the individual, and determine a first decision boundary metric (such as but not limited to the response criterion) from the response profile. As described herein, including in connection with FIGS. 4A and 4B, the decision boundary metric (such as but not limited to the response criterion) gives a quantitative measure of a tendency of the individual to provide at least one type of response of the two or more differing types of responses (Response A vs. Response B) to the task or the interference. The programmed processing unit is further configured to execute processor-executable instructions to adapt the task and/or the interference based on the computed first decision boundary metric (such as but not limited to the response criterion) (to generate a second session), receive data indicative of the first response of the individual to the task and the second response of the individual to the interference, analyze at least some portion of the data to compute a second response profile and a second decision boundary metric (such as but not limited to the response criterion) representative of the second performance of the individual. The programmed processing unit is further configured to execute processor-executable instructions, based on the first decision boundary metric (such as but not limited to the response criterion) and second decision boundary metric (such as but not limited to the response criterion), to generate an output to the user interface indicative of one or more of: (i) a likelihood of the individual experiencing an adverse event in response to administration of the pharmaceutical agent, drug, or biologic, (ii) a change in one or more of the amount, concentration, or dose titration of a pharmaceutical agent, drug, biologic or other medication being or to be administered to an individual, and (iii) a change in the individual's cognitive response capabilities, a recommended treatment regimen, or recommending or determining a degree of effectiveness of at least one of a behavioral therapy, counseling, or physical exercise.

In a non-limiting example, based on the results of the analysis of the first decision boundary metric (such as but not limited to the response criterion) and the second decision boundary metric (such as but not limited to the response criterion), a medical, healthcare, or other professional (with consent of the individual) can gain a better understanding of an individual's cognitive response capabilities, and potentially more specifically identify the type of cognitive condition, executive function disorder, or disease that could be affecting an individual's cognitive abilities (including by reviewing the results of the analysis in conjunction with other physiological, behavioral, and/or diagnostic measures). For example, the results may be used to identify individuals of a group who may better benefit from a first type of pharmaceutical agent, drug, biologic, or other medication, while other individuals in the group could benefit from a second type.

In a non-limiting example, based on the results of the analysis of the first decision boundary metric (such as but not limited to the response criterion) and the second decision boundary metric (such as but not limited to the response criterion), a medical, healthcare, or other professional (with consent of the individual) can gain a better understanding of potential adverse events which may occur (or potentially are occurring) if the individual is administered a particular type of, amount, concentration, or dose titration of a pharmaceutical agent, drug, biologic, or other medication, including potentially affecting cognition.

In a non-limiting example, a searchable database is provided herein that includes data indicative of the results of the analysis of the first decision boundary metric (such as but not limited to the response criterion) and the second decision boundary metric (such as but not limited to the response criterion) for particular individuals, along with known levels of efficacy of at least one types of pharmaceutical agent, drug, biologic, or other medication experiences by the individuals, and/or quantifiable information on one or more adverse events experienced by the individual with administration of the at least one types of pharmaceutical agent, drug, biologic, or other medication. The searchable database can be configured to provide metrics for use to determine whether a given individual is a candidate for benefiting from a particular type of pharmaceutical agent, drug, biologic, or other medication based on the response measures, response profiles, and/or decision boundary metric (such as but not limited to response criteria) obtained for the individual in interacting with the task and/or interference rendered at the computing device.

As a non-limiting example, based on data indicative of a user interaction with the tasks and/or interference rendered at a user interface of a computing device, the decision boundary metric (such as but not limited to the response criterion) could provide information on the tendency of an individual to a particular type of response, such as but not limited to the degree of impulsiveness or conservativeness of the individual's cognitive response strategy. This data can assist with identifying a treatment regimen, or a degree of effectiveness of a behavioral therapy, counseling, and/or physical exercise.

In a non-limiting example, based on data indicative of a user interaction with the tasks and/or interference rendered at a user interface of a computing device, the decision boundary metric (such as but not limited to the response criterion) could provide information on the individual, based on the degree of impulsiveness or conservativeness of the individual's cognitive response strategy. This data can assist with identifying whether the individual is a candidate for a particular type of drug (such as but not limited to a stimulant, e.g., methylphenidate or amphetamine) or whether it might be beneficial for the individual to have the drug administered in conjunction with a regiment of specified repeated interactions with the tasks and/or interference rendered to the computing device. Other non-limiting examples of a biologic, drug or other pharmaceutical agent applicable to any example described herein include methylphenidate (MPH), scopolamine, donepezil hydrochloride, rivastigmine tartrate, memantine HCl, solanezumab, aducanumab, and crenezumab.

Another example system, method, and apparatus according to the principles herein can be configured to enhance the cognitive skills in an individual. In an example implementation, a programmed processing unit is configured to execute processor-executable instructions to render a task with an interference at a user interface. As described in greater detail herein, one or more of the task and the interference can be time-varying and have a response deadline, such that the user interface imposes a limited time period for receiving at least one type of response from the individual interacting with the apparatus or system. The processing unit is configured to control the user interface to receive data indicative of one or more of an amount, concentration, or dose titration of a pharmaceutical agent, drug, or biologic being or to be administered to an individual, and to measure data indicative of two or more differing types of responses to the task or to the interference. The programmed processing unit is further configured to execute processor-executable instructions to cause the example system or apparatus to receive data indicative of a first response of the individual to the task and a second response of the individual to the interference (from a first session), analyze at least some portion of the data to compute a first response profile representative of the first performance of the individual, and determine a first decision boundary metric (such as but not limited to the response criterion) from the response profile. As described herein, including in connection with FIGS. 4A and 4B, the decision boundary metric (such as but not limited to the response criterion) gives a quantitative measure of a tendency of the individual to provide at least one type of response of the two or more differing types of responses (Response A vs. Response B) to the task or the interference. The programmed processing unit is further configured to execute processor-executable instructions to adapt the task and/or the interference based on the first decision boundary metric (such as but not limited to the response criterion) and the amount or concentration of a pharmaceutical agent, drug, or biologic (to generate a second session), receive data indicative of the first response of the individual to the task and the second response of the individual to the interference, analyze at least some portion of the data to compute a second response profile and a second decision boundary metric (such as but not limited to the response criterion) representative of the second performance of the individual. The programmed processing unit is further configured to execute processor-executable instructions, based on the first decision boundary metric (such as but not limited to the response criterion) and second decision boundary metric (such as but not limited to the response criterion), to generate an output to the user interface indicative of one or more of: (i) a likelihood of the individual experiencing an adverse event in response to administration of the pharmaceutical agent, drug, or biologic, (ii) a recommended change in one or more of the amount, concentration, or dose titration of the pharmaceutical agent, drug, biologic or other medication, and (iii) a change in the individual's cognitive response capabilities, a recommended treatment regimen, or recommending or determining a degree of effectiveness of at least one of a behavioral therapy, counseling, or physical exercise.

In a non-limiting example, based on the results of the analysis of the first decision boundary metric (such as but not limited to the response criterion) and the second decision boundary metric (such as but not limited to the response criterion), a medical, healthcare, or other professional (with consent of the individual) can gain a better understanding of potential adverse events which may occur (or potentially are occurring) if the individual is administered a different amount, concentration, or dose titration of a pharmaceutical agent, drug, biologic, or other medication, including potentially affecting cognition.

In a non-limiting example, a searchable database is provided herein that includes data indicative of the results of the analysis of the first decision boundary metric (such as but not limited to the response criterion) and the second decision boundary metric (such as but not limited to the response criterion) for particular individuals, along with known levels of efficacy of at least one types of pharmaceutical agent, drug, biologic, or other medication experiences by the individuals, and/or quantifiable information on one or more adverse events experienced by the individual with administration of the at least one types of pharmaceutical agent, drug, biologic, or other medication. The searchable database can be configured to provide metrics for use to determine whether a given individual is a candidate for benefiting from a particular type of pharmaceutical agent, drug, biologic, or other medication based on the response measures, response profiles, and/or decision boundary metric (such as but not limited to response criteria) obtained for the individual in interacting with the task and/or interference rendered at the computing device. As a non-limiting example, based on data indicative of a user interaction with the tasks and/or interference rendered at a user interface of a computing device, the decision boundary metric (such as but not limited to the response criterion) could provide information on the individual, based on the degree of impulsiveness or conservativeness of the individual's cognitive response strategy. This data can assist with identifying whether the individual is a candidate for a particular type of drug (such as but not limited to a stimulant, e.g., methylphenidate or amphetamine) or whether it might be beneficial for the individual to have the drug administered in conjunction with a regiment of specified repeated interactions with the tasks and/or interference rendered to the computing device. Other non-limiting examples of a biologic, drug or other pharmaceutical agent applicable to any example described herein include methylphenidate (MPH), scopolamine, donepezil hydrochloride, rivastigmine tartrate, memantine HCl, solanezumab, aducanumab, and crenezumab.

In an example, the change in the individual's cognitive response capabilities comprises an indication of a change in degree of impulsiveness or conservativeness of the individual's cognitive response strategy.

As a non-limiting example, given that impulsive behavior is attendant with ADHD, an example cognitive platform that is configured for delivering treatment (including of executive function) may promote less impulsive behavior in a regimen. This may target dopamine systems in the brain, increasing normal regulation, which may result in a transfer of benefits of the reduction of impulsive behavior to the everyday life of an individual.

Stimulants such as methylphenidate and amphetamine are also administered to individuals with ADHD, to increase levels of norepinephrine and dopamine in the brain. Their cognitive effects may be attributed to their actions at the prefrontal cortex, however, there may not be remediation of cognitive control deficits or other cognitive abilities. An example cognitive platform herein can be configured for delivering treatment (including of executive function) to remediate an individual's cognitive control deficit.

The use of the example systems, methods, and apparatus according to the principles described herein can be applicable to many different types of neuropsychological conditions, such as but not limited to dementia, Parkinson's disease, cerebral amyloid angiopathy, familial amyloid neuropathy, Huntington's disease, or other neurodegenerative condition, autism spectrum disorder (ASD), presence of the 16p11.2 duplication, and/or an executive function disorder, such as but not limited to attention deficit hyperactivity disorder (ADHD), sensory-processing disorder (SPD), mild cognitive impairment (MCI), Alzheimer's disease, multiple-sclerosis, schizophrenia, major depressive disorder (MDD), or anxiety.

In any example implementation, data and other information from an individual is collected, transmitted, and analyzed with their consent.

As a non-limiting example, the cognitive platform described in connection with any example system, method and apparatus herein, including a cognitive platform based on interference processing, can be based on or include the Project: EVO™ platform by Akili Interactive Labs, Inc., Boston, MA.

Non-Limiting Example Tasks and Interference

The effects of interference processing on the cognitive control abilities of individuals has been reported. See, e.g., A. Anguera, Nature vol. 501, p. 97 (Sep. 5, 2013) (the "Nature article"). See, also, U.S. Publication No. 20140370479A1 (U.S. application Ser. No. 13/879,589), filed on Nov. 10, 2011, which is incorporated herein by reference. Some of those cognitive abilities include cognitive control abilities in the areas of attention (selectivity, sustainability, etc.), working memory (capacity and the quality of information maintenance in working memory) and goal management (ability to effectively parallel process two attention-demanding tasks or to switch tasks). As an example, children diagnosed with ADHD (attention deficit hyperactivity disorder) exhibit difficulties in sustaining attention. Attention selectivity was found to depend on neural processes involved in ignoring goal-irrelevant information and on processes that facilitate the focus on goal-relevant information. The publications report neural data showing that when two objects are simultaneously placed in view, focusing attention on one can pull visual processing resources away from the other. Studies were also reported showing that memory depended more on effectively ignoring distractions, and the ability to maintain information in mind is vulnerable to interference by both distraction and interruption. Interference by distraction can be, e.g., an interference that is a non-target, that distracts the individual's attention from the primary task, but that the instructions indicate the individual is not to respond to. Interference by interruption/interruptor can be, e.g., an interference that is a target or two or more targets, that also distracts the individual's attention from the primary task, but that the instructions indicate the individual is to respond to (e.g., for a single target) or choose between/among (e.g., a forced-choose situation where the individual decides between differing degrees of a feature).

There were also fMRI results reported showing that diminished memory recall in the presence of a distraction can be associated with a disruption of a neural network involving the prefrontal cortex, the visual cortex, and the hippocampus (involved in memory consolidation). Prefrontal cortex networks (which play a role in selective attention) can be vulnerable to disruption by distraction. The publications also report that goal management, which requires cognitive control in the areas of working memory or selective attention, can be impacted by a secondary goal that also demands cognitive control. The publications also reported data indicating beneficial effects of interference processing as an intervention with effects on an individual's cognitive abilities, including to diminish the detrimental effects of distractions and interruptions. The publications described cost measures that can be computed (including an interference cost) to quantify the individual's performance, including to assess single-tasking or multitasking performance.

An example cost measure disclosed in the publications is the percentage change in an individual's performance at a single-tasking task as compared to a multi-tasking task, such that greater cost (that is, a more negative percentage cost) indicates increased interference when an individual is engaged in single-tasking vs multi-tasking.

The tangible benefits of computer-implemented interference processing are also reported. For example, the Nature paper states that multi-tasking performance assessed using computer-implemented interference processing was able to quantify a linear age-related decline in performance in adults from 20 to 79 years of age. The Nature paper also reports that older adults (60 to 85 years old) who interacted with an adaptive form of the computer-implemented interference processing exhibited reduced multitasking costs, with the gains persisting for six (6) months. The Nature paper also reported that age-related deficits in neural signatures of cognitive control, as measured with electroencephalography, were remediated by the multitasking training (using the computer-implemented interference processing), with enhanced midline frontal theta power and frontal-posterior theta coherence. Interacting with the computer-implemented interference processing resulted in performance benefits that extended to untrained cognitive control abilities (enhanced sustained attention and working memory), with an increase in midline frontal theta power predicting a boost in sustained attention and preservation of multitasking improvement six (6) months later.

The example systems, methods, and apparatus according to the principles herein are configured to classify an individual as to cognitive abilities and/or to enhance those cognitive abilities based on implementation of interference processing using a computerized cognitive platform. The example systems, methods, and apparatus are configured to implement a form of multi-tasking using the capabilities of a programmed computing device, where an individual is required to perform a task and an interference substantially simultaneously, and the sensing and measurement capabilities of the computing device are configured to collect data indicative of the physical actions taken by the individual during the response execution time to respond to the task at substantially the same time as the computing device collects the data indicative of the physical actions taken by the individual to respond to the interference. The capabilities of the computing devices and programmed processing units to render the task and/or the interference in real time to a user interface, and to measure the data indicative of the individual's responses to the task and/or the interference in real time and substantially simultaneously can provide quantifiable measures of an individual's cognitive capabilities to rapidly switch to and from different tasks and interferences or to perform multiple, different, tasks or interferences in a row (including for single-tasking, where the individual is required to perform a single type of task for a set period of time).

In any example herein, the task and/or interference includes a response deadline, such that the user interface imposes a limited time period for receiving at least one type of response from the individual interacting with the apparatus or computing device. For example, the period of time that an individual is required to interact with a computing device or other apparatus to perform a task and/or an interference can be a predetermined amount of time, such as but not limited to about 30 seconds, about 1 minute, about 4 minutes, about 7 minutes, about 10 minutes, or greater than 10 minutes.

The example systems, methods, and apparatus can be configured to implement a form of multi-tasking to provide measures of the individual's capabilities in deciding whether to perform one action instead of another and to activate the rules of the current task in the presence of an interference such that the interference diverts the individual's attention from the task, as a measure of an individual's cognitive abilities in executive function control.

The example systems, methods, and apparatus can be configured to implement a form of single-tasking, where measures of the individual's performance at interacting with a single type of task (i.e., with no interference) for a set period of time (such as but not limited to navigation task only or a target discriminating task only) can also be used to provide measure of an individual's cognitive abilities.

The example systems, methods, and apparatus can be configured to implement sessions that involve differing sequences and combinations of single-tasking and multi-tasking trials. In a first example implementation, a session can include a first single-tasking trial (with a first type of task), a second single-tasking trial (with a second type of task), and a multi-tasking trial (a primary task rendered with an interference). In a second example implementation, a session can include two or more multi-tasking trials (a primary task rendered with an interference). In a third example implementation, a session can include two or more single-tasking trials (all based on the same type of tasks or at least one being based on a different type of task).

The performance can be further analyzed to compare the effects of two different types of interference (e.g. distraction or interruptor) on the performances of the various tasks. Some comparisons can include performance without interference, performance with distraction, and performance with interruption. The cost of each type of interference (e.g. distraction cost and interruptor/multi-tasking cost) on the performance level of a task is analyzed and reported to the individual.

In any example herein, the interference can a secondary task that includes a stimulus that is either a non-target (as a distraction) or a target (as an interruptor), or a stimulus that is differing types of targets (e.g., differing degrees of a facial expression or other characteristic/feature difference).

Based on the capability of a programmed processing unit to control the effecting of multiple separate sources (including sensors and other measurement components) and the receiving of data selectively from these multiple different sources at substantially simultaneously (i.e., at roughly the same time or within a short time interval) and in real-time, the example systems, methods, and apparatus herein can be used to collect quantitative measures of the responses form an individual to the task and/or interference which could not be achieved using normal human capabilities. As a result, the example systems, methods, and apparatus herein can be configured to implement a programmed processing unit to render the interference substantially simultaneously with the task over certain time periods.

In some example implementations, the example systems, methods, and apparatus herein also can be configured to receive the data indicative of the measure of the degree and type of the individual's response to the task substantially simultaneously as the data indicative of the measure of the degree and type of the individual's response to the interference is collected (whether the interference includes a target or a non-target). In some examples, the example systems, methods, and apparatus are configured to perform the analysis by applying scoring or weighting factors to the measured data indicative of the individual's response to a non-target that differ from the scoring or weighting factors applied to the measured data indicative of the individual's response to a target, in order to compute an interference cost.

In some example implementations, the example systems, methods, and apparatus herein also can be configured to selectively receive data indicative of the measure of the degree and type of the individual's response to an interference that includes a target stimulus (i.e., an interruptor) substantially simultaneously (i.e., at substantially the same time) as the data indicative of the measure of the degree and type of the individual's response to the task is collected and to selectively not collect the measure of the degree and type of the individual's response to an interference that includes a non-target stimulus (i.e., a distraction) substantially simultaneously (i.e., at substantially the same time) as the data indicative of the measure of the degree and type of the individual's response to the task is collected. That is, the example systems, methods, and apparatus are configured to discriminate between the windows of response of the individual to the target versus non-target by selectively controlling the state of the sensing/measurement components for measuring the response either temporally and/or spatially. This can be achieved by selectively activating or de-activating sensing/measurement components based on the presentation of a target or non-target, or by receiving the data measured for the individual's response to a target and selectively not receiving (e.g., disregarding, denying, or rejecting) the data measured for the individual's response to a non-target.

As described herein, using the example systems, methods, and apparatus herein can be implemented to provide a measure of the cognitive abilities of an individual in the area of attention, including based on capabilities for sustainability of attention over time, selectivity of attention, and reduction of attention deficit. Other areas of an individual's cognitive abilities that can be measured using the example systems, methods, and apparatus herein include impulsivity, inhibition, perceptive abilities, reaction and other motor functions, visual acuity, long-term memory, working memory, short-term memory, logic, and decision-making.

As described herein, using the example systems, methods, and apparatus herein can be implemented to adapt the tasks and/or is the most critical design element for any effective plasticity-harnessing tool. Also, we wanted to control every single game element-timing, positioning, and nature of stimuli—so that we could record neural activity during game play and understand what was changing in the brain in response to training.

FIGS. 10A-15V show non-limiting example user interfaces that can be rendered using example systems, methods, and apparatus herein to render the tasks and/or interferences for user interactions. The non-limiting example user interfaces of FIGS. 10A-15V also can be used for one or more of: to display instructions to the individual for performing the tasks and/or interferences, to collect the data indicative of the individual's responses to the tasks and/or the interferences, to show progress metrics, and to provide the analysis metrics.

FIGS. 10A-10D show non-limiting example user interfaces rendered using example systems, methods, and apparatus herein. As shown in FIGS. 10A-10B, an example programmed processing unit can be used to render to the user interfaces (including graphical user interfaces) display features 1000 for displaying instructions to the individual for performing the tasks and/or interferences, and metric features 1002 to show status indicators from progress metrics and/or results from application of analytics to the data collected from the individual's interactions (including the responses to tasks/interferences) to provide the analysis metrics. In any example systems, methods, and apparatus herein, the response classifier can be used to provide the analysis metrics provided as a response output. In any example systems, methods, and apparatus herein, the data collected from the user interactions can be used as input to train the response classifier. As shown in FIGS. 10A-10B, an example programmed processing unit also may be used to render to the user interfaces (including graphical user interfaces) an avatar or other processor-rendered guide 1004 that an individual is required to control (such as but not limited to navigate a path or other environment in a visuo-motor task, and/or to select an object in a target discrimination task). As shown in FIG. 10B, the display features 1000 can be used to instruct the individual what is expected to perform a navigation task while the user interface depicts (using the dashed line) the type of movement of the avatar or other processor-rendered guide 1004 required for performing the navigation task. As shown in FIG. 10C, the display features 1000 can be used to instruct the individual what is expected to perform a target discrimination task while the user interface depicts the type of object(s) 1006 and 1008 that may be rendered to the user interface, with one type of object 1006 designated as a target while the other type of object 1008 that may be rendered to the user interface is designated as a non-target (e.g., by being crossed out in this example). As shown in FIG. 10D, the display features 1000 can be used to instruct the individual what is expected to perform both a navigation task as a primary task and a target discrimination as a secondary task (i.e., an interference) while the user interface depicts (using the dashed line) the type of movement of the avatar or other processor-rendered guide 1004 required for performing the navigation task, and the user interface renders the object type designated as a target object 1006 and the object type designated as a non-target object 1008.

Figure 11A:
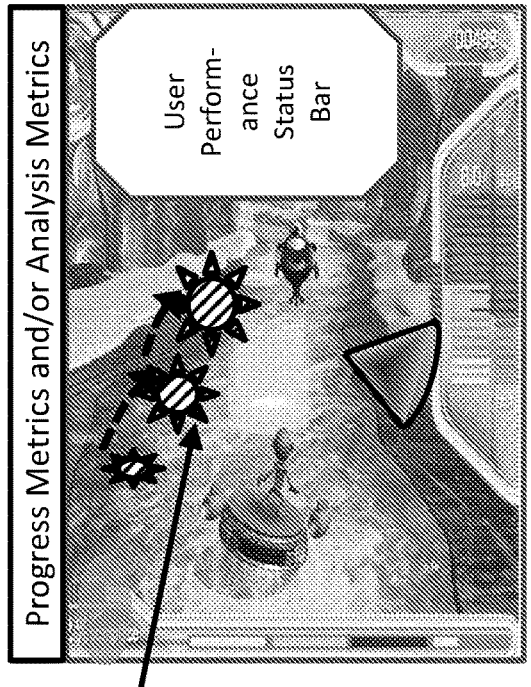
FIGS. 11A-11D show examples of the time-varying features of example objects (targets or non-targets) that can be rendered to an example user interface, according to the principles herein.
Figure 11B:
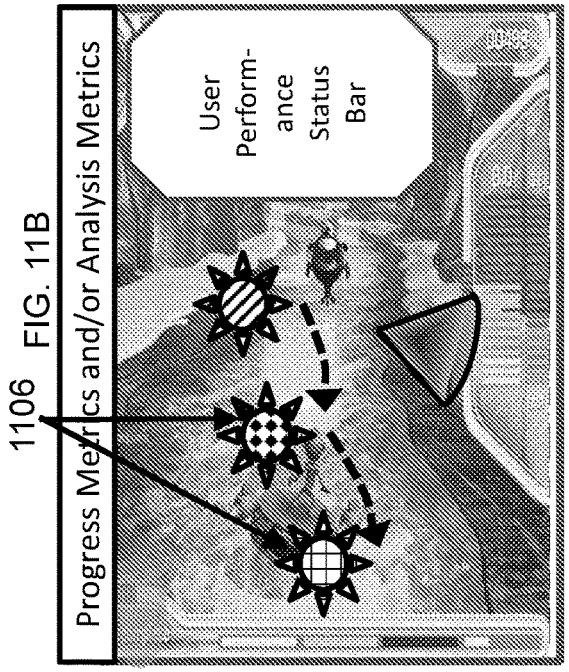
Figure 11C:
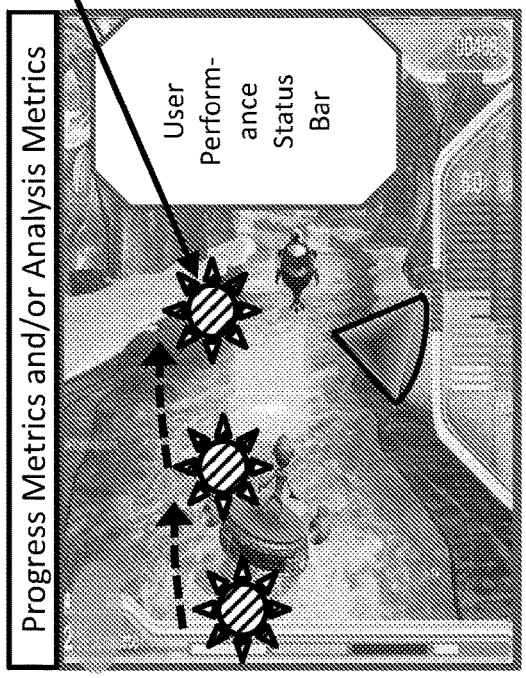
Figure 11D:
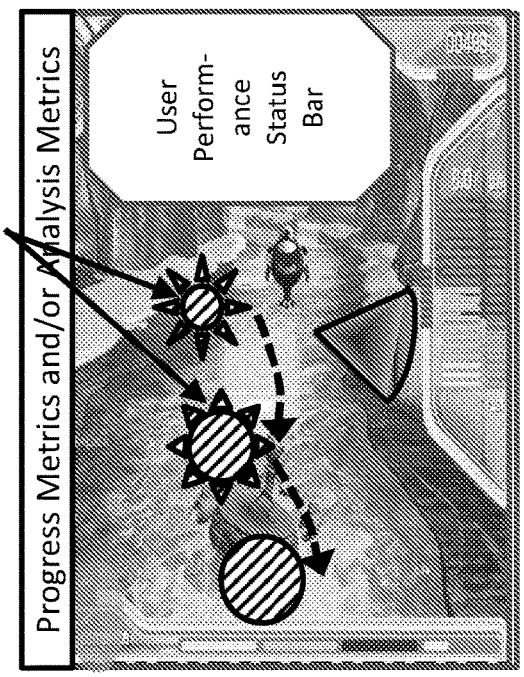

FIGS. 11A-11D show examples of the features of object(s) (targets or non-targets) that can be rendered as time-varying characteristics to an example user interface, according to the principles herein. FIG. 11A shows an example where the modification to the time-varying characteristics of an aspect of the object 1100 rendered to the user interface is a dynamic change in position and/or speed of the object 1100 relative to environment rendered in the graphical user interface. FIG. 11B shows an example where the modification to the time-varying characteristics of an aspect of the object 1102 rendered to the user interface is a dynamic change in size and/or direction of trajectory/motion, and/or orientation of the object 1102 relative to the environment rendered in the graphical user interface. FIG. 11C shows an example where the modification to the time-varying characteristics of an aspect of the object 1104 rendered to the user interface is a dynamic change in shape or other type of the object 1104 relative to the environment rendered in the graphical user interface. In this non-limiting example, the time-varying characteristic of object 1104 is effected using morphing from a first type of object (a star object) to a second type of object (a round object). In another non-limiting example, the time-varying characteristic of object 1104 is effected by rendering a blendshape as a proportionate combination of a first type of object and a second type of object. FIG. 11C shows an example where the modification to the time-varying characteristics of an aspect of the object 1104 rendered to the user interface is a dynamic change in shape or other type of the object 1104 rendered in the graphical user interface (in this non-limiting example, from a star object to a round object). FIG. 11D shows an example where the modification to the time-varying characteristics of an aspect of the object 1106 rendered to the user interface is a dynamic change in pattern, or color, or visual feature of the object 1106 relative to environment rendered in the graphical user interface (in this non-limiting example, from a star object having a first pattern to a round object having a second pattern). In another non-limiting example, the time-varying characteristic of object can be a rate of change of a facial expression depicted on or relative to the object.

Figure 12A:
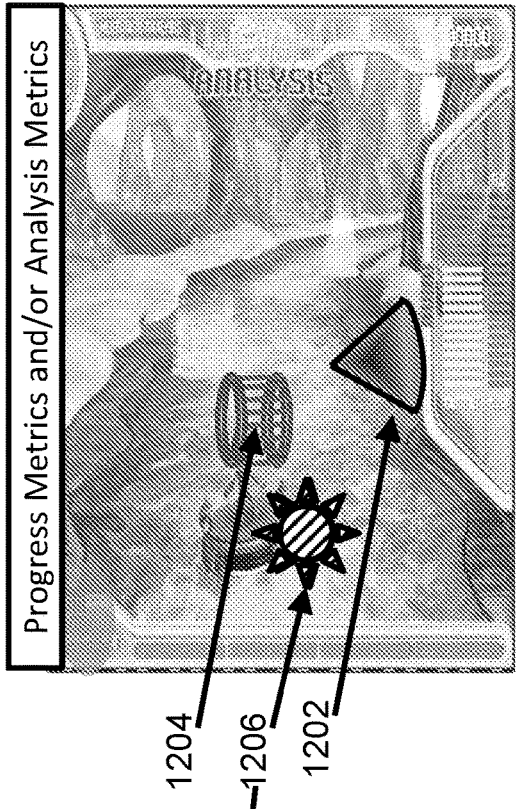
FIGS. 12A-12T show the dynamics of tasks and interferences that can be rendered at user interfaces, according to the principles herein.
Figure 12C:
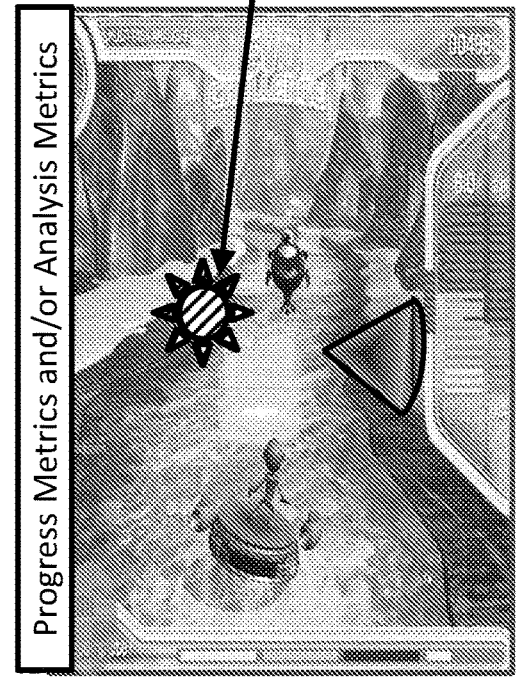
Figure 12B:
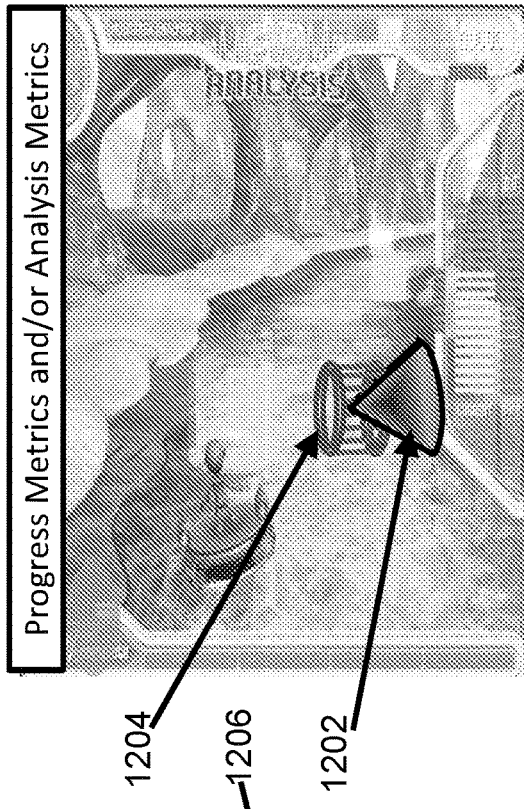
Figure 12D:
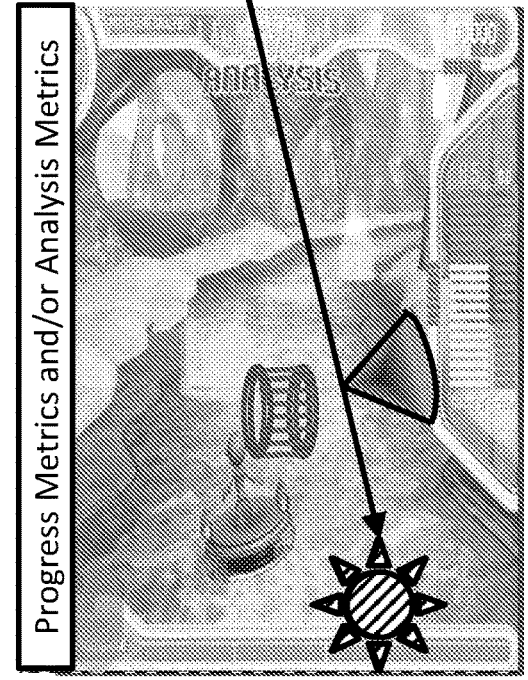
Figure 12E:
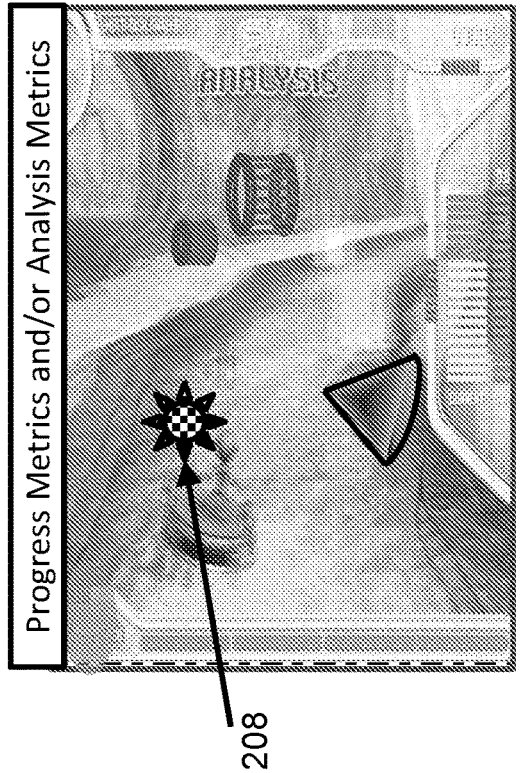
Figure 12F:
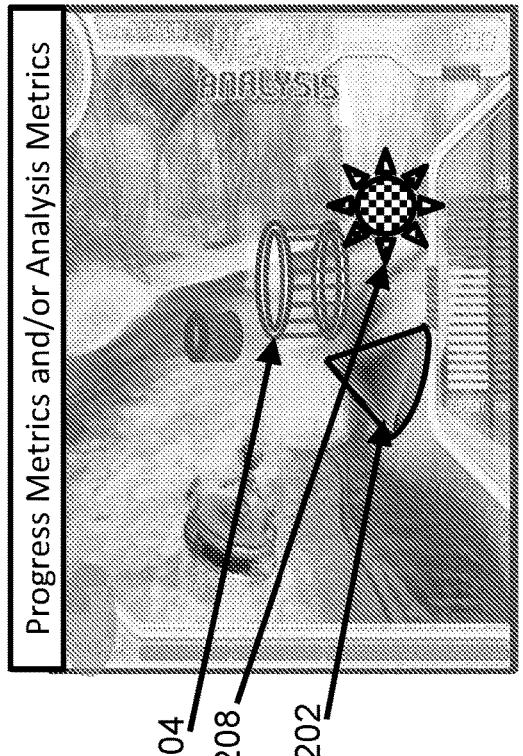
Figure 12G:
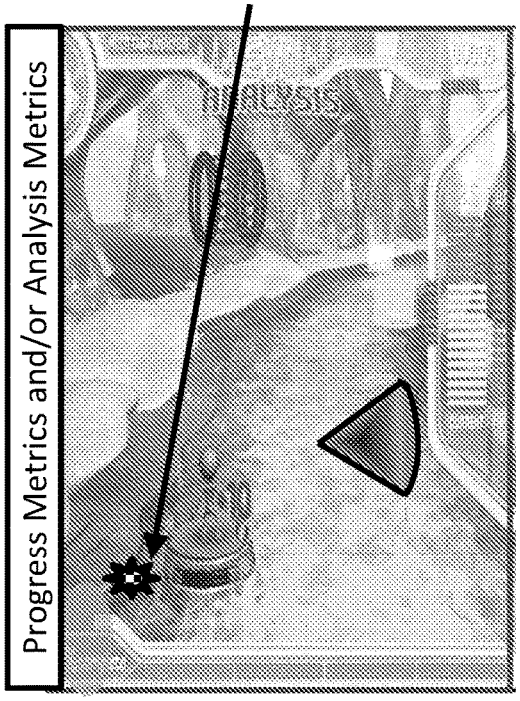
Figure 12H:
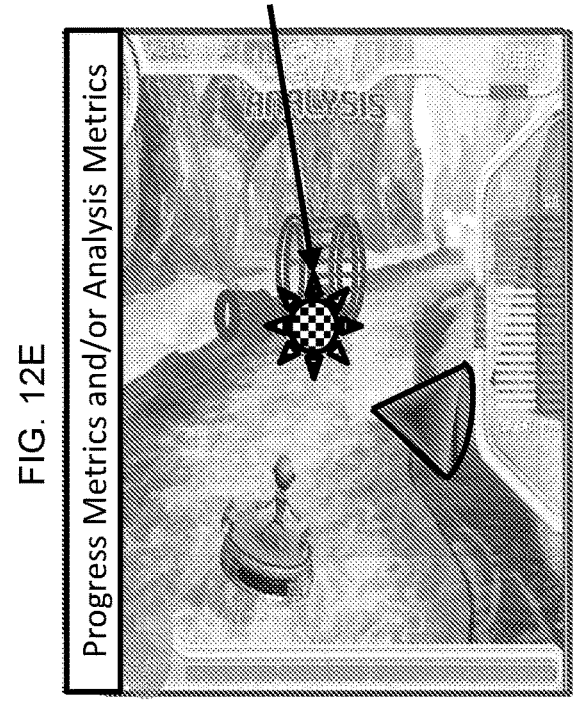
Figure 12I:
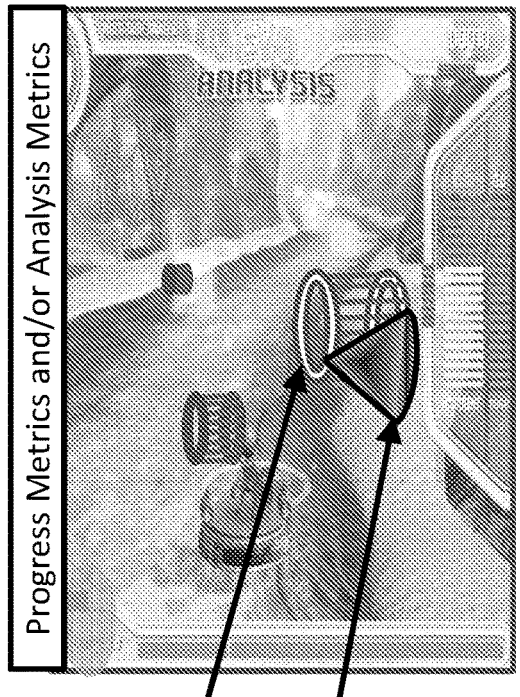
Figure 12J:
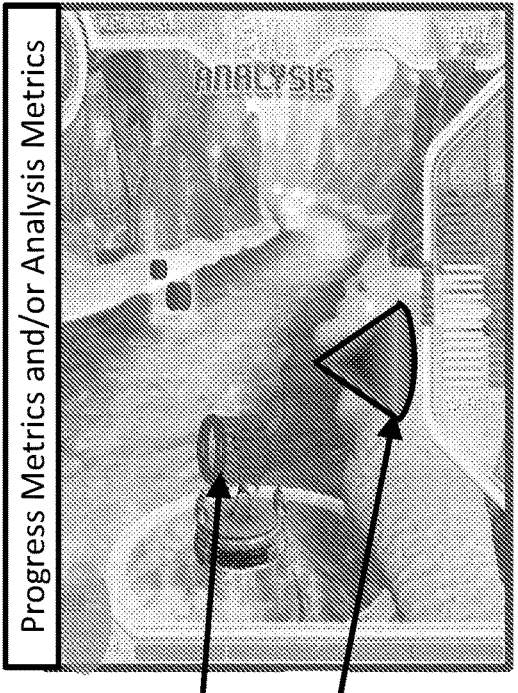
Figure 12K:
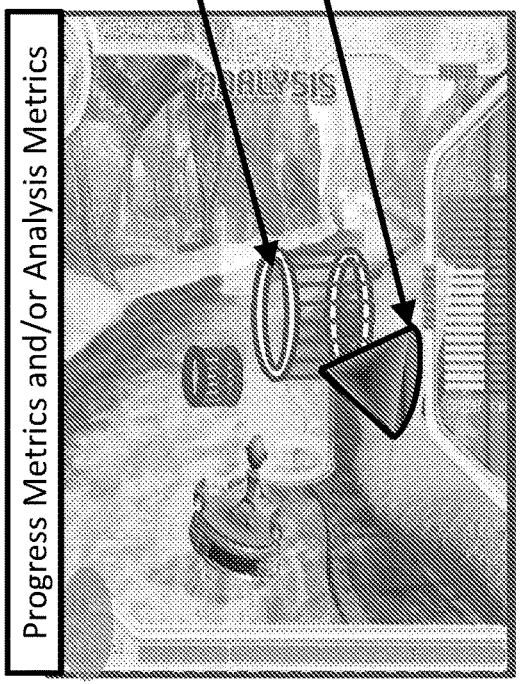
Figure 12L:
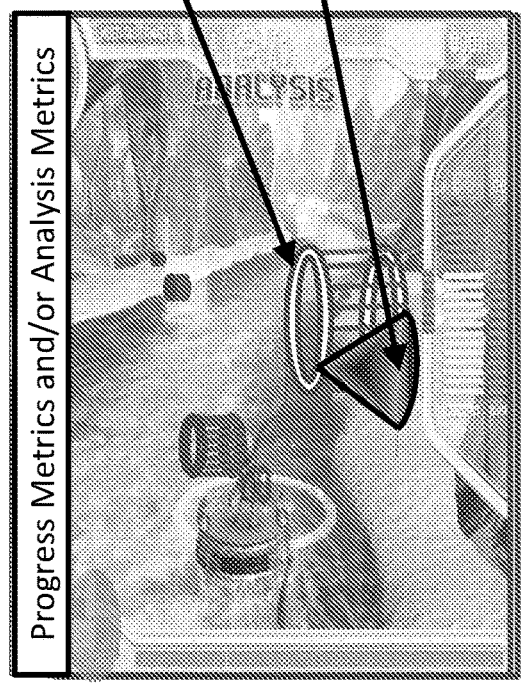
Figure 12M:
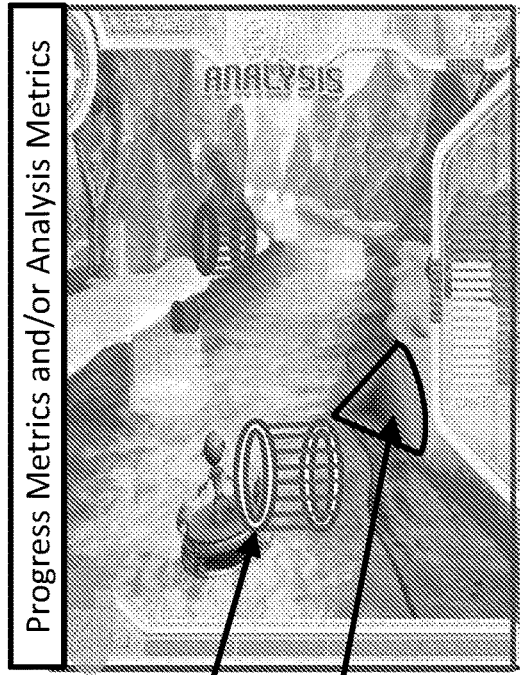
Figure 12N:
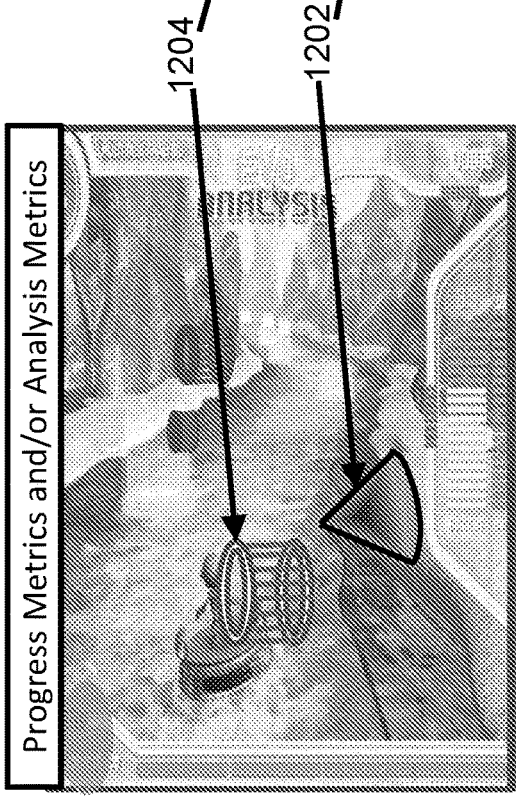
Figure 12O:
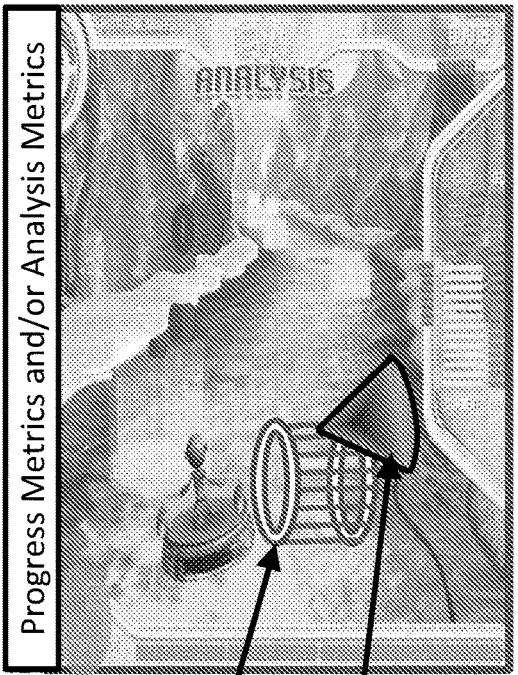
Figure 12P:
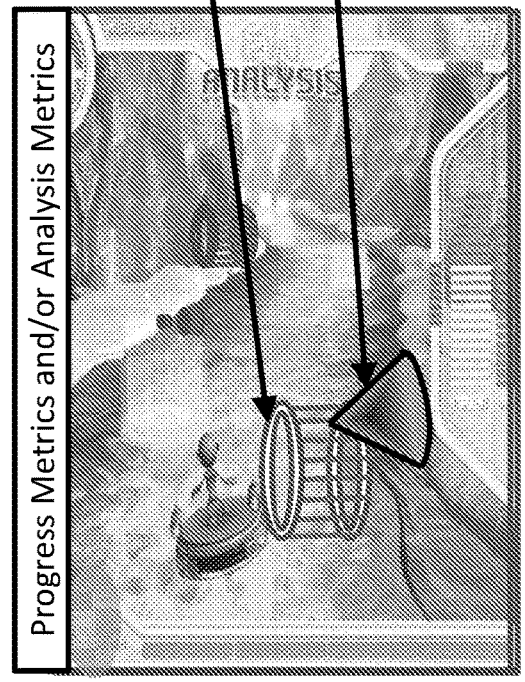
Figure 12Q:
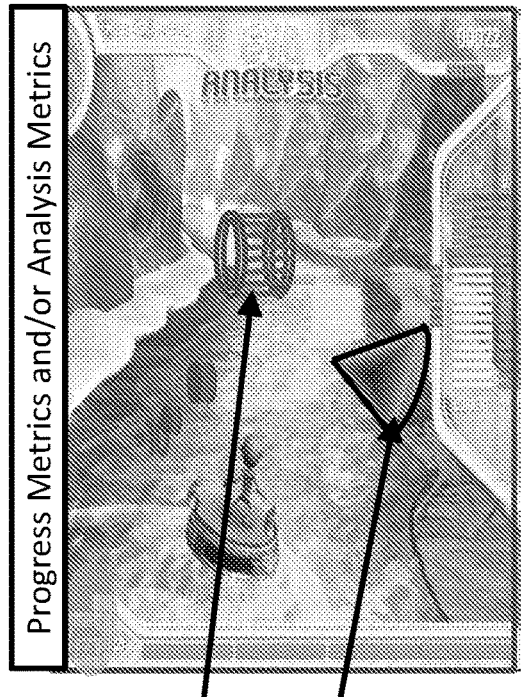
Figure 12S:
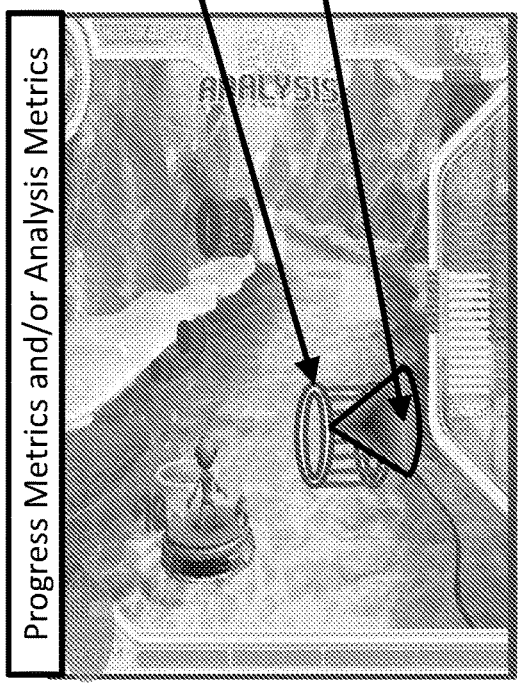
Figure 12R:
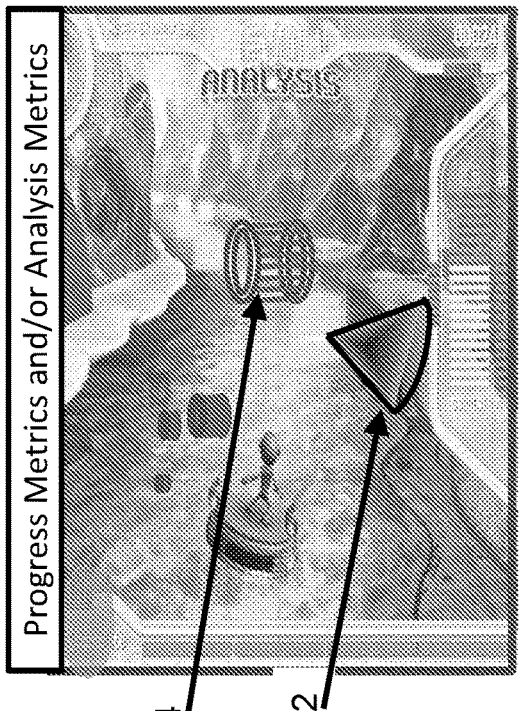
Figure 12T:
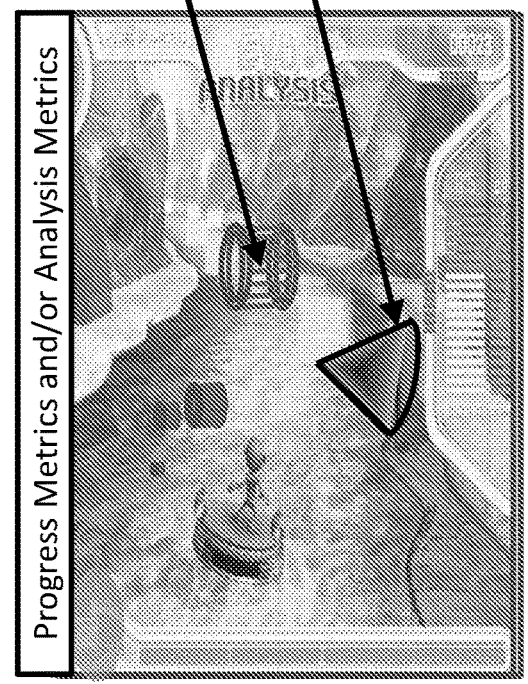
Figure 13A:
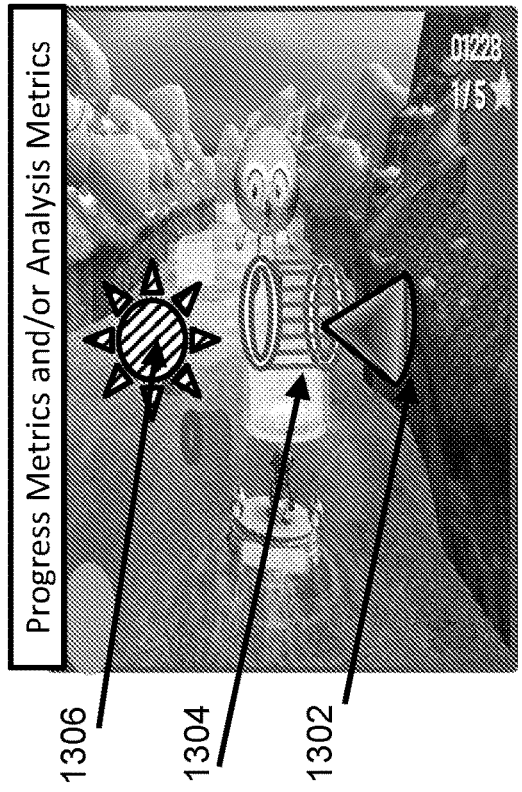
FIGS. 13A-13D show examples of the dynamics of multi-tasking involving user interaction with an implementation of a navigation task and with an interference rendered to a user interface of an example user interface, according to the principles herein.
Figure 13C:
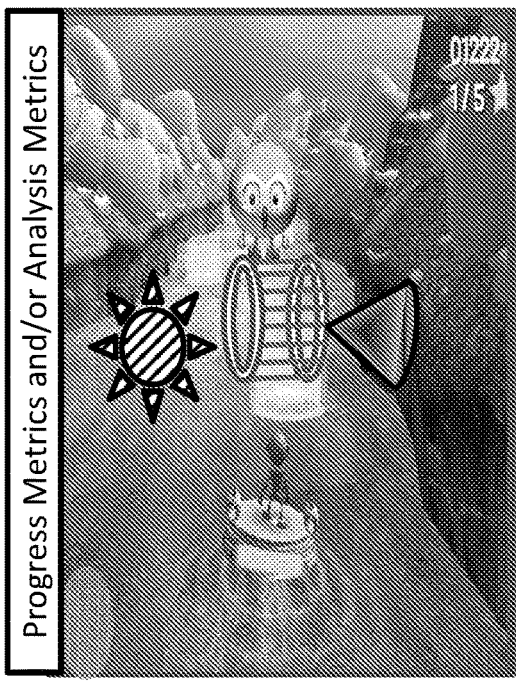
Figure 13B:
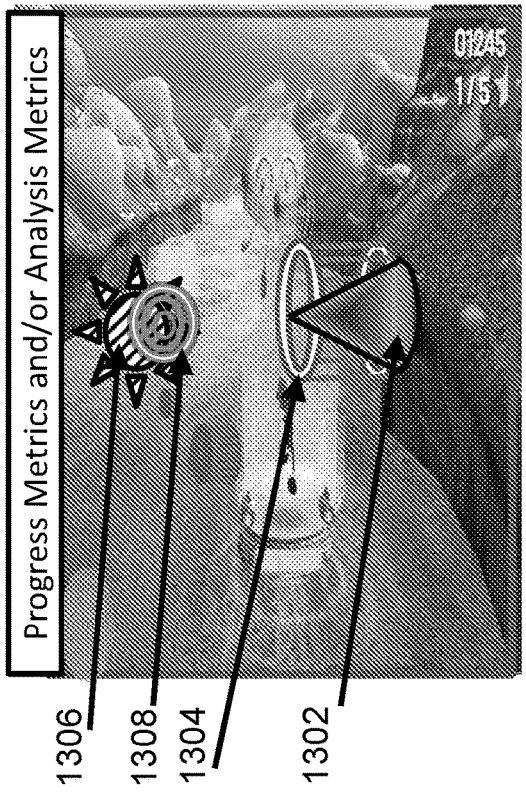
Figure 13D:
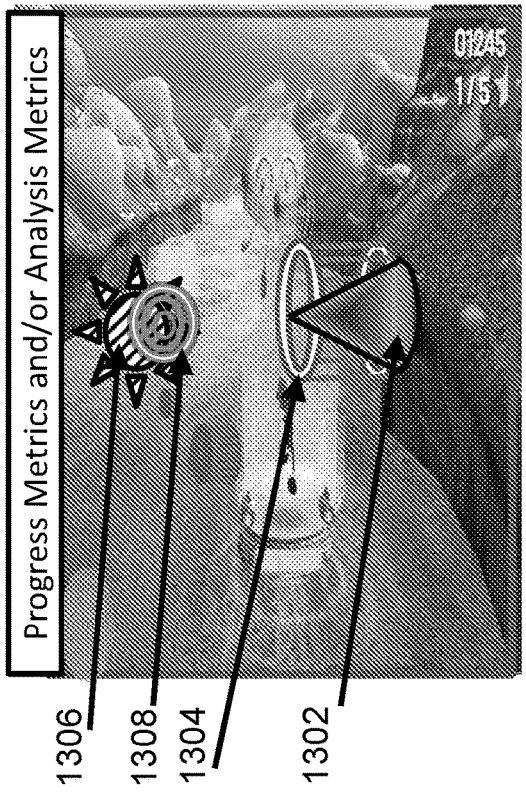

FIGS. 12A-12T show a non-limiting example of the dynamics of tasks and interferences that can be rendered at user interfaces, according to the principles herein. In this example, the task is a visuo-motor navigation task, and the interference is target discrimination (as a secondary task). As shown in FIGS. 12D, 12I-12K, and 12O-12Q, the individual is required to perform the navigation task by controlling the motion of the avatar 1202 along a path that coincides with the milestone objects 1204. FIGS. 12A-12T show a non-limiting example implementation where the individual is expected to actuate an apparatus or computing device (or other sensing device) to cause the avatar 1202 to coincide with the milestone object 1204 as the response in the navigation task, with scoring based on the success of the individual at crossing paths with (e.g., hitting) the milestone objects 1204. In another example, the individual is expected to actuate an apparatus or computing device (or other sensing device) to cause the avatar 1202 to miss the milestone object 1204, with scoring based on the success of the individual at avoiding the milestone objects 1204. FIGS. 12A-12C show the dynamics of a target object 1206 (a star having a first type of pattern), where the time-varying characteristic is the trajectory of motion of the object. FIGS. 12E-12H show the dynamics of a non-target object 1208 (a star having a second type of pattern), where the time-varying characteristic is the trajectory of motion of the object. FIGS. 12I-12T show the dynamics of other portions of the navigation task, where the individual is expected to guide the avatar 1202 to cross paths with the milestone object 1204 in the absence of an interference (a secondary task).

In the example of FIGS. 12A-12T, the processing unit of the example system, method, and apparatus is configured to receive data indicative of the individual's physical actions to cause the avatar 1202 to navigate the path. For example, the individual may be required to perform physical actions to "steer" the avatar, e.g., by changing the rotational orientation or otherwise moving a computing device. Such action can cause a gyroscope or accelerometer or other motion or position sensor device to detect the movement, thereby providing measurement data indicative of the individual's degree of success in performing the navigation task.

In the example of FIGS. 12A-12C and 12E-12H, the processing unit of the example system, method, and apparatus is configured to receive data indicative of the individual's physical actions to perform the target discrimination task. For example, the individual may be instructed prior to a trial or other session to tap, or make other physical indication, in response to display of a target object 1206, and not to tap to make the physical indication in response to display of a non-target object 1208. In FIGS. 12A-12C and 12E-12H, the target discrimination task acts as an interference (i.e., a secondary task) to the primary navigation task, in an interference processing multi-tasking implementation. As described hereinabove, the example systems, methods, and apparatus can cause the processing unit to render a display feature (e.g., display feature 1000) to display the instructions to the individual as to the expected performance. As also described hereinabove, the processing unit of the example system, method, and apparatus can be configured to (i) receive the data indicative of the measure of the degree and type of the individual's response to the primary task substantially simultaneously as the data indicative of the measure of the degree and type of the individual's response to the interference is collected (whether the interference includes a target or a non-target), or (i) to selectively receive data indicative of the measure of the degree and type of the individual's response to an interference that includes a target stimulus (i.e., an interruptor) substantially simultaneously (i.e., at substantially the same time) as the data indicative of the measure of the degree and type of the individual's response to the task is collected and to selectively not collect the measure of the degree and type of the individual's response to an interference that includes a non-target stimulus (i.e., a distraction) substantially simultaneously (i.e., at substantially the same time) as the data indicative of the measure of the degree and type of the individual's response to the task is collected FIGS. 13A-13D show another non-limiting example of the dynamics of tasks and interferences that can be rendered at user interfaces, according to the principles herein. In this example, the task is a visuo-motor navigation task, and the interference is target discrimination (as a secondary task), where an individual is required to perform physical actions to cause an avatar 1302 to navigate to cross paths with the milestone object 1304 as the primary task and interact with an object 1306 as target discrimination (interference as a secondary task). FIGS. 13A-13D show an example of the type of reward 1308 that can be shown on the graphical user interface responsive to the individual's indication of selecting a target object. In this non-limiting example, the reward 1308 is a set of rings that are rendered near the target 1306 at substantially the time the individual makes the second response selecting the target. In a non-limiting example, the second response is made by a tap, or other physical action to a portion of the user interface based on the individual's decision to enter a response.

Figure 14A:
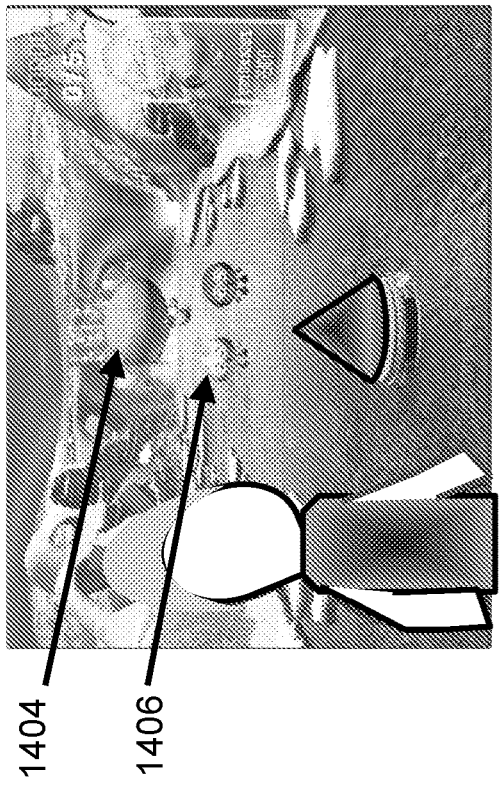
FIGS. 14A-14D show examples of the dynamics of an instructions panel rendered to a user interface of an example user interface, according to the principles herein.
Figure 14C:
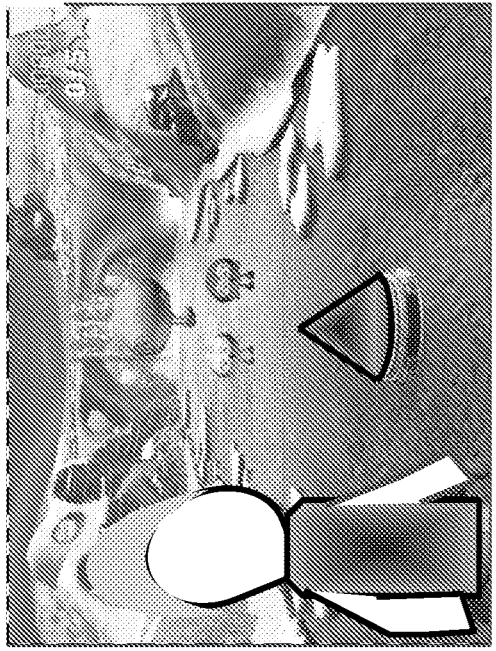
Figure 14B:
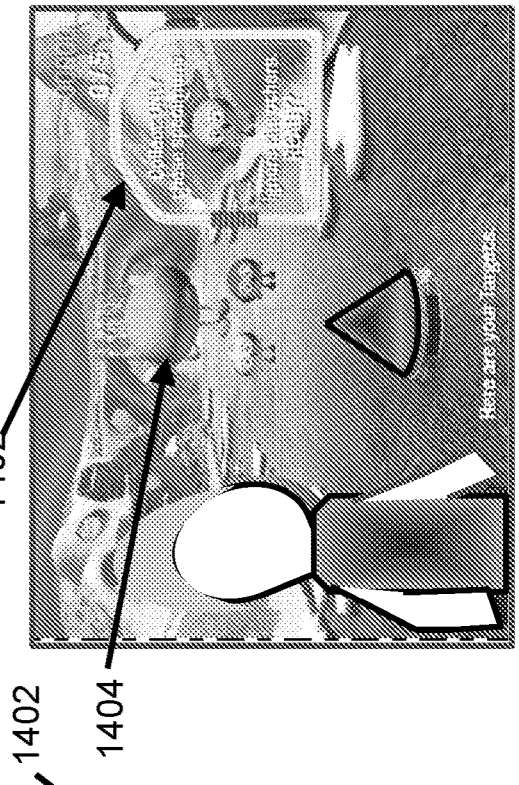
Figure 14D:
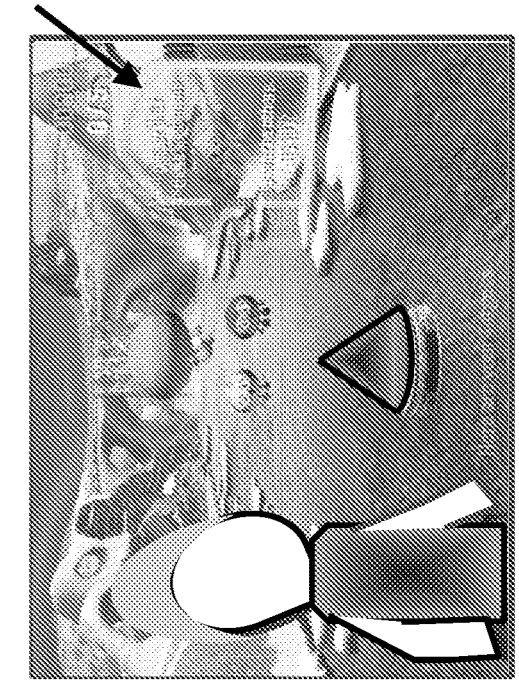

FIGS. 14A-14D show examples of the dynamics of an instructions panel rendered to a user interface of an example user interface. In this example, the processing unit causes the user interface to show the dynamics of movement of the instructions panel 1402 into view from the right side of the user interface. FIGS. 14A-14D also show non-limiting examples of target objects 1404 and non-target objects 1406. In this non-limiting example, the target objects 1404 and non-target objects 1406 differ in color. As shown in FIG. 14D, the instructions panel 1402 can include a visual representation of the target object in addition to the written instructions to the individual.

Figure 15B:
FIGS. 15A-15V show examples of the dynamics of multi-tasking involving user interaction with an implementation of a navigation task and with an interference.
Figure 15A:
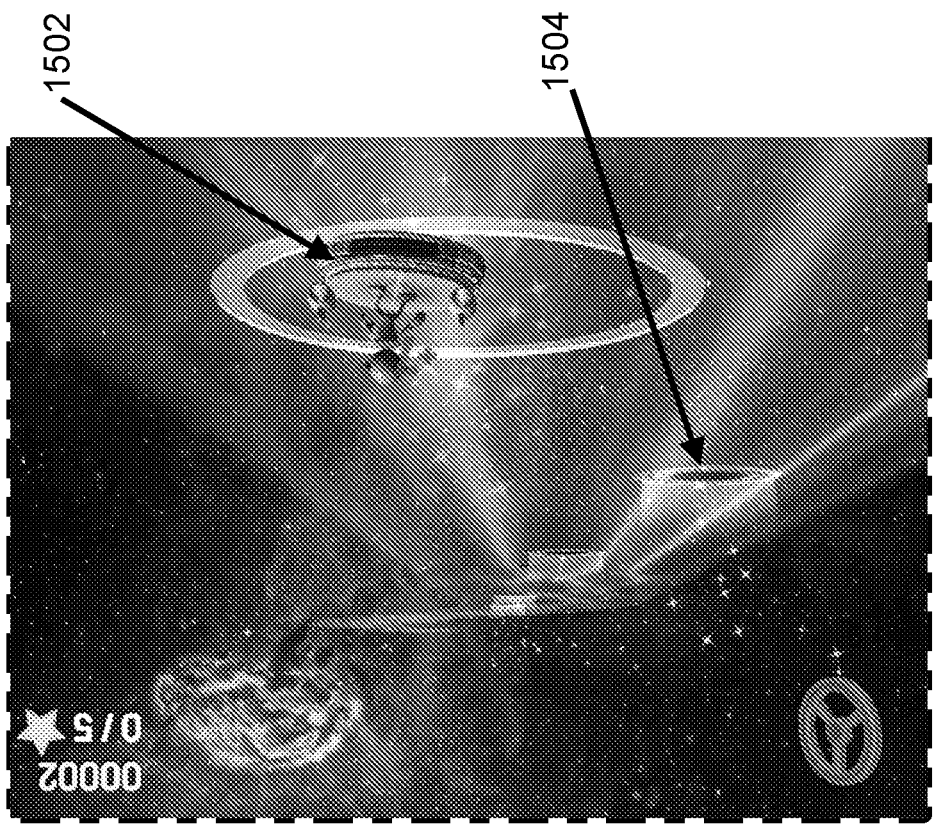
Figure 15D:
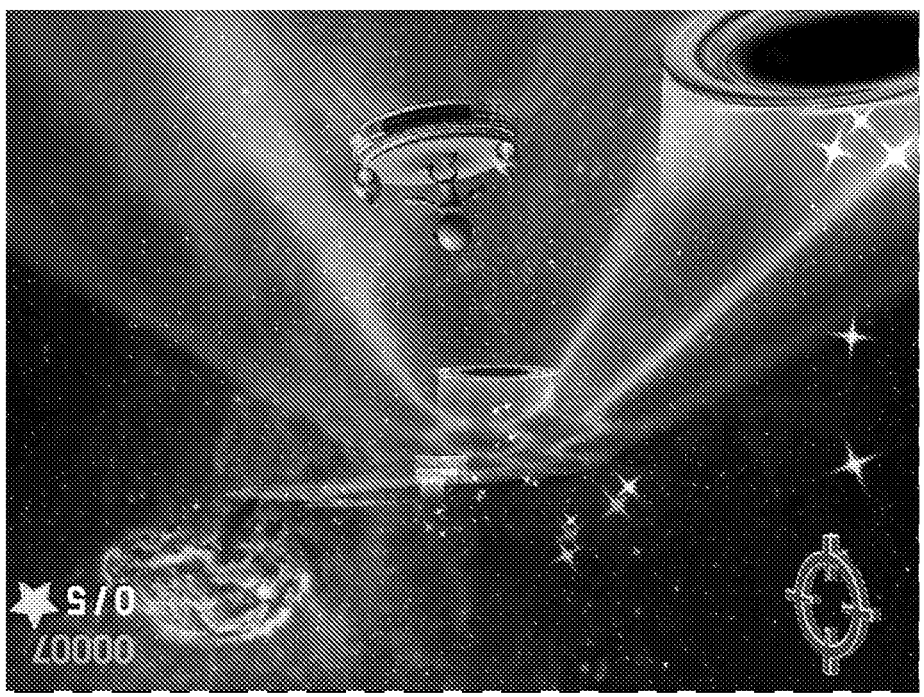
Figure 15C:
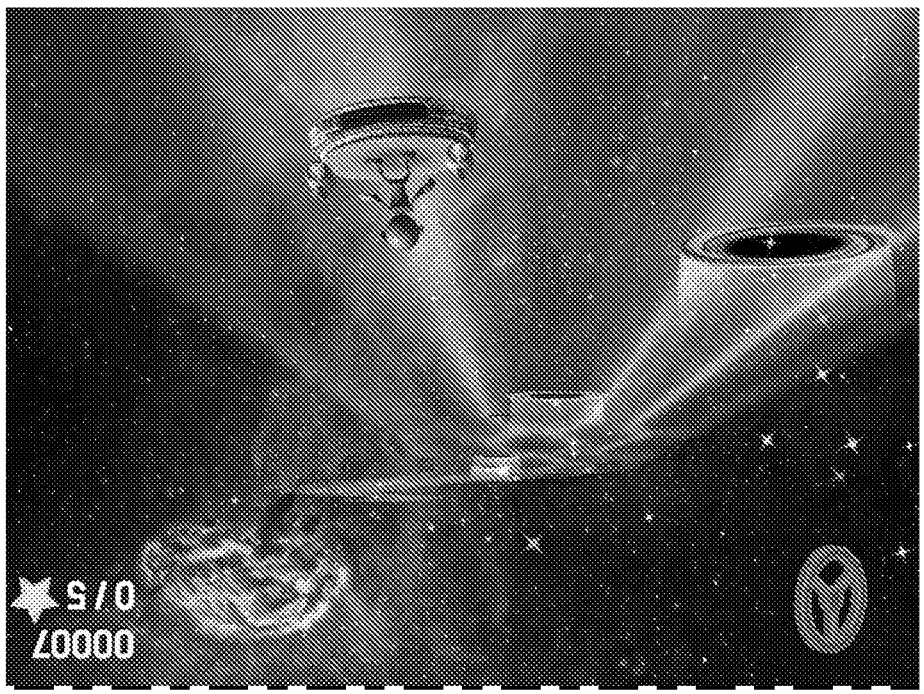
Figure 15F:
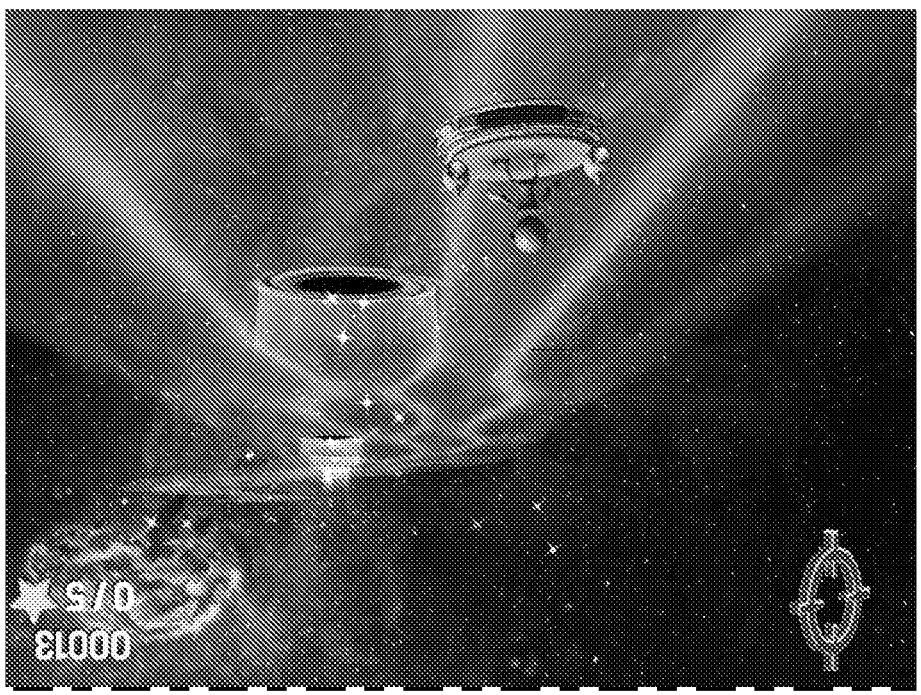
Figure 15E:
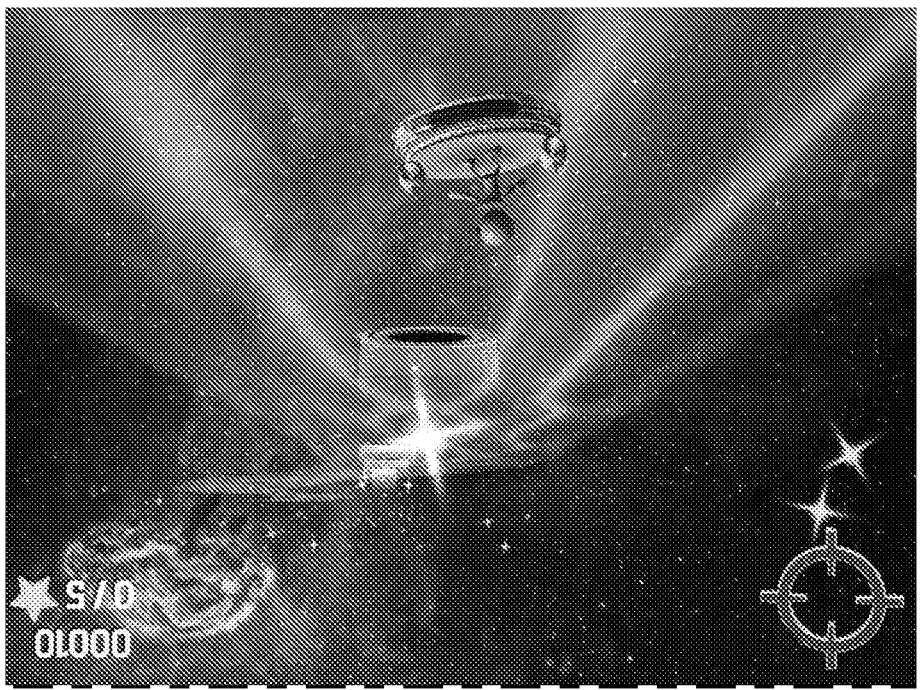
Figure 15H:
Figure 15G:
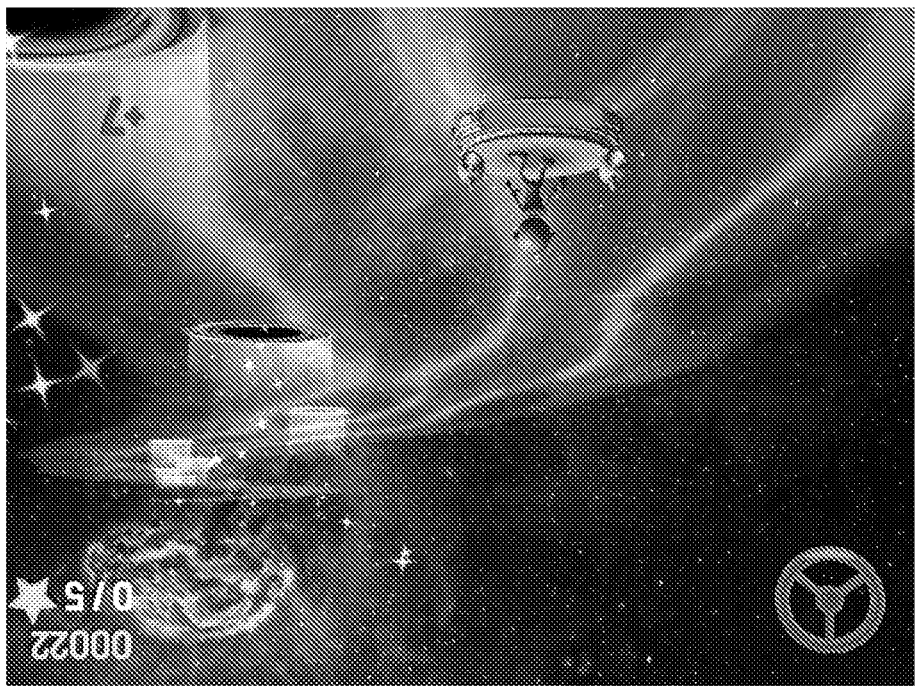
Figure 15J:
Figure 15I:
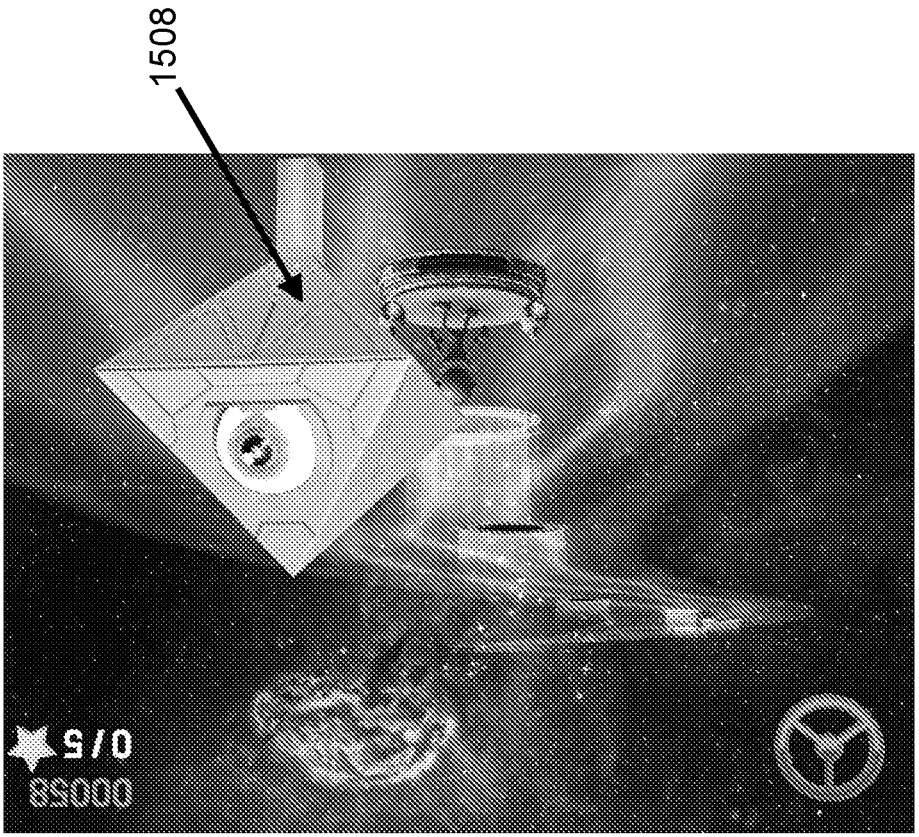
Figure 15L:
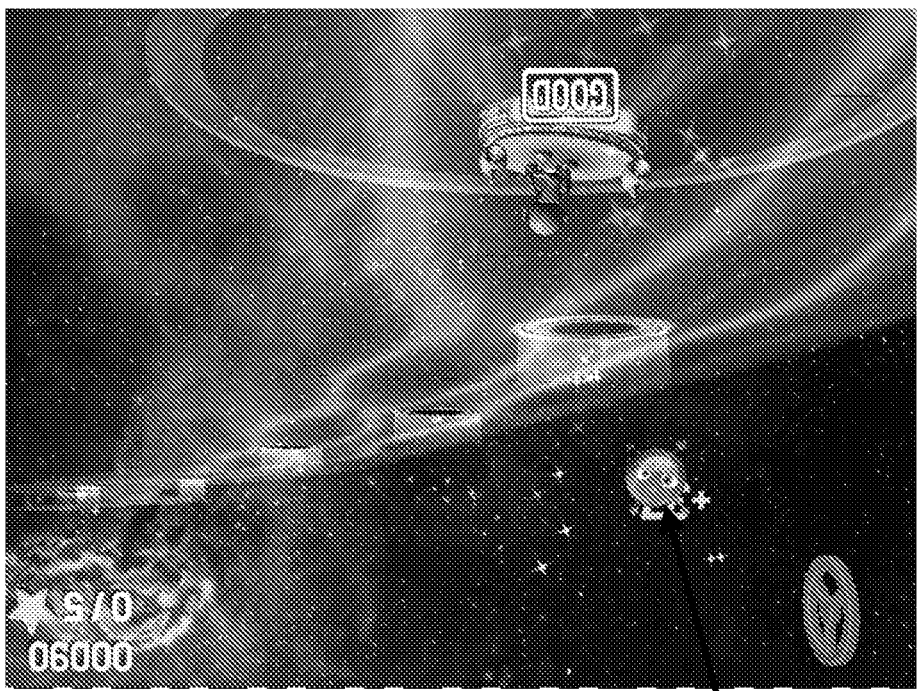
Figure 15K:
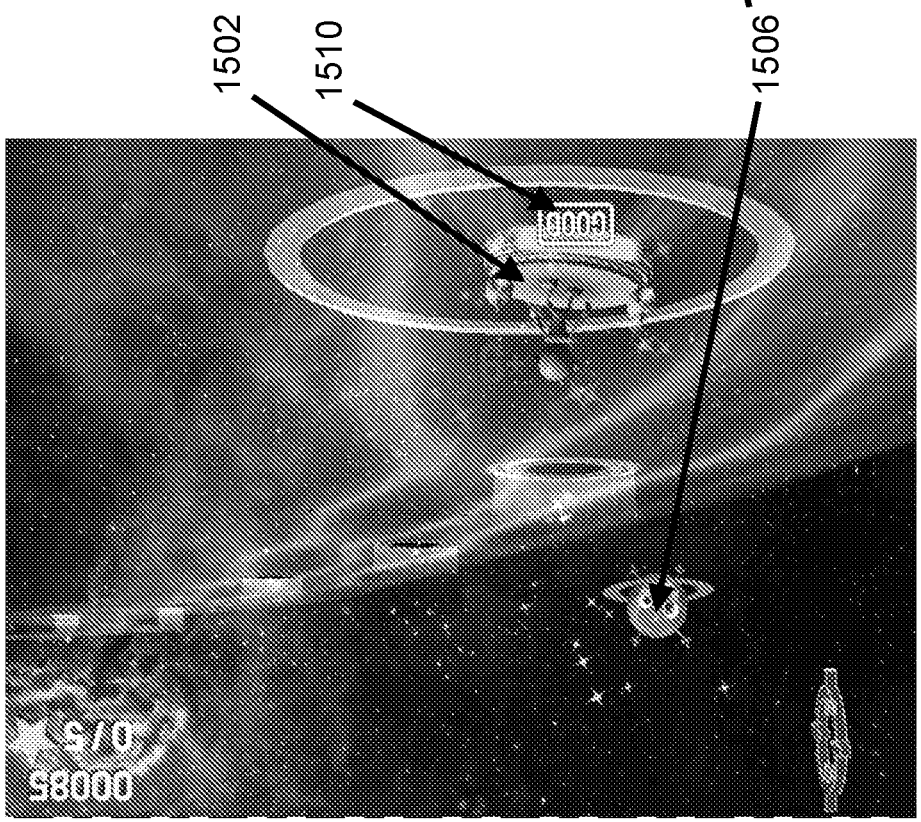
Figure 15N:
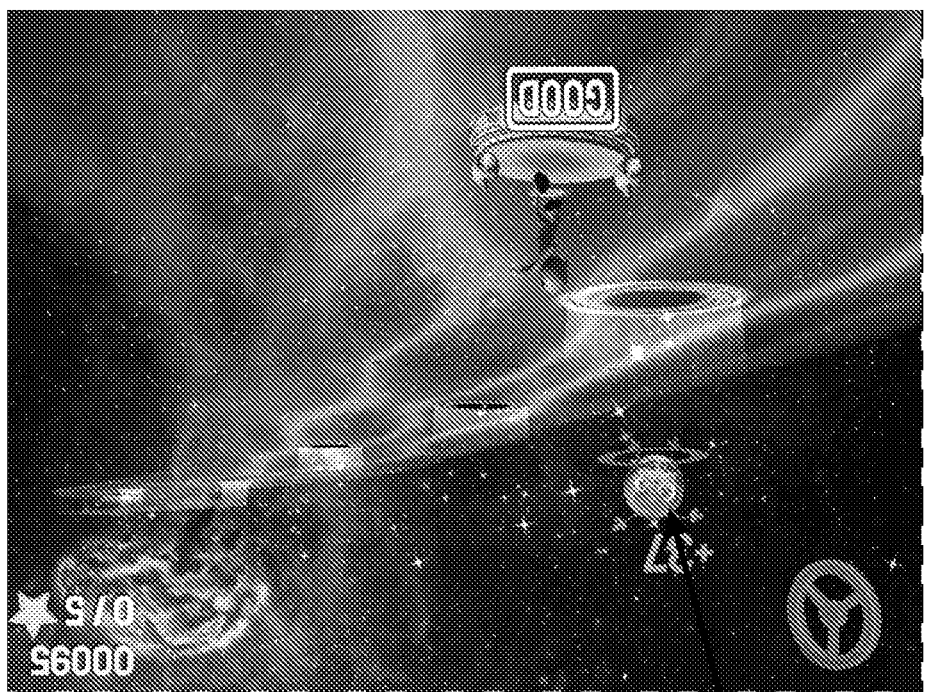
Figure 15M:
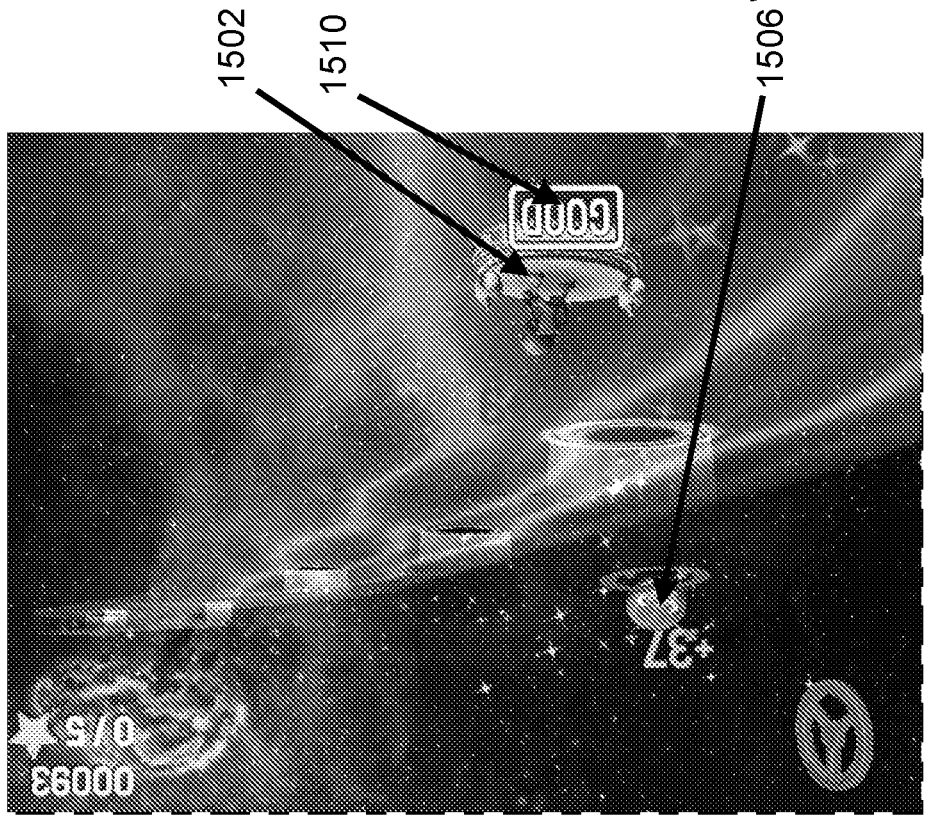
Figure 15P:
Figure 15O:
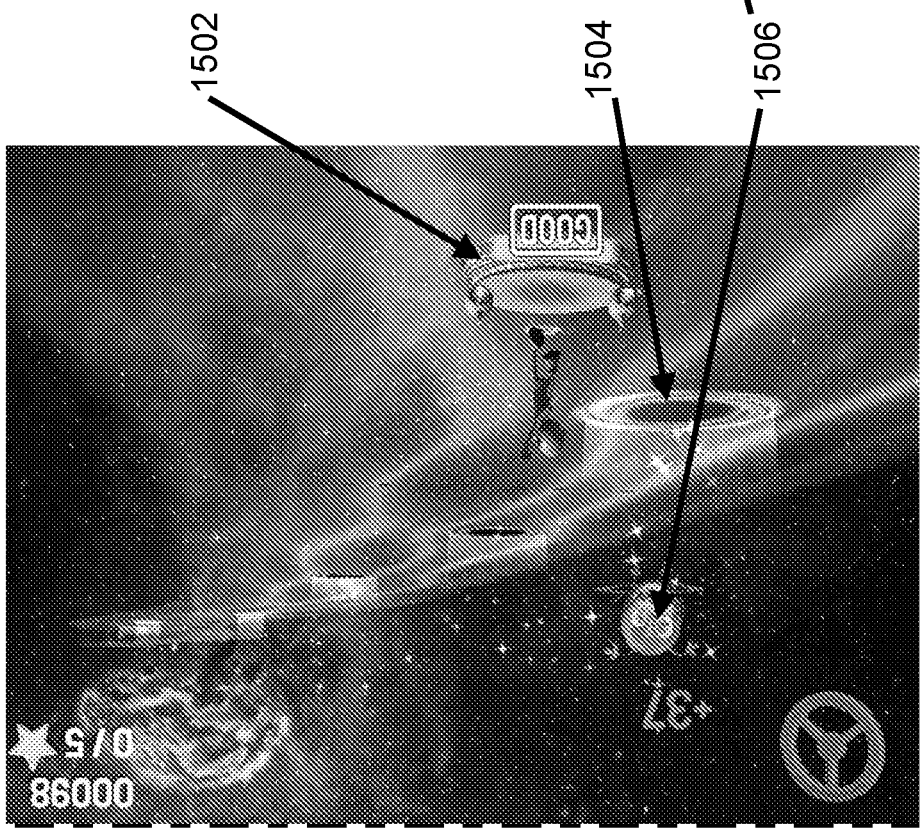
Figure 15R:
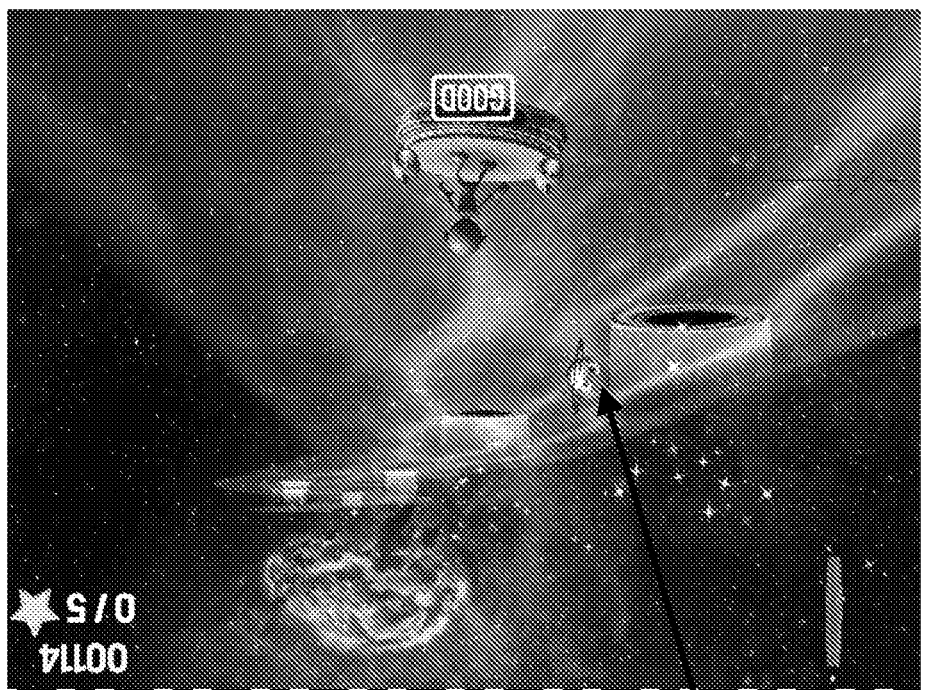
Figure 15Q:
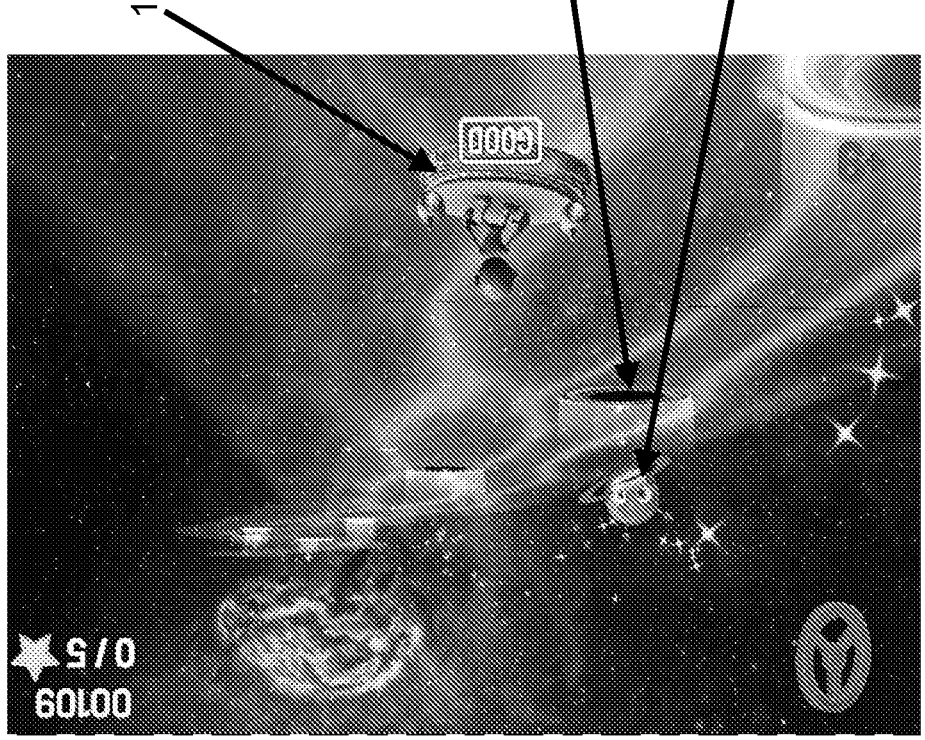
Figure 15T:
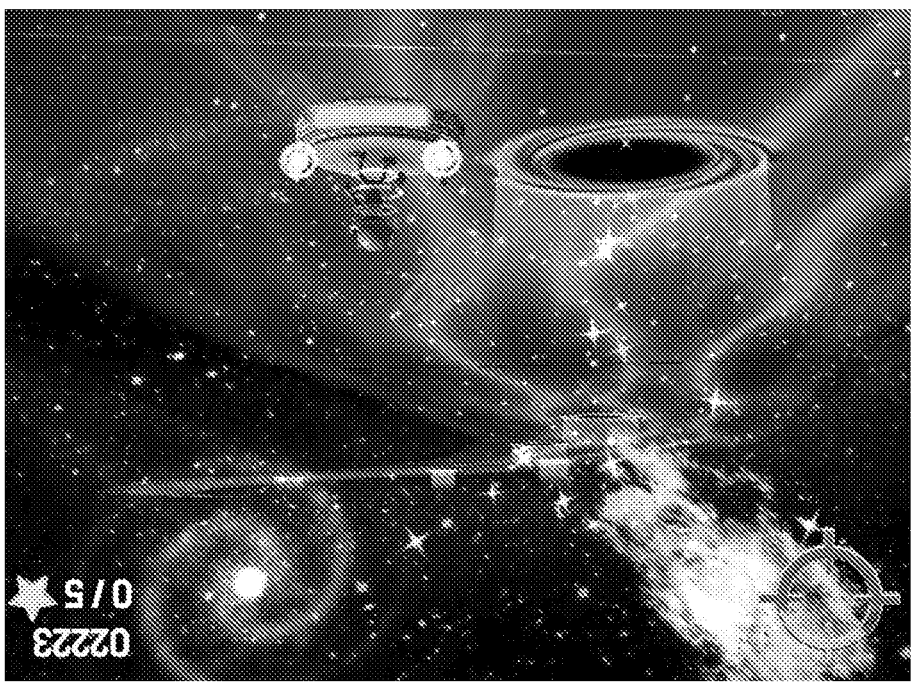
Figure 15S:
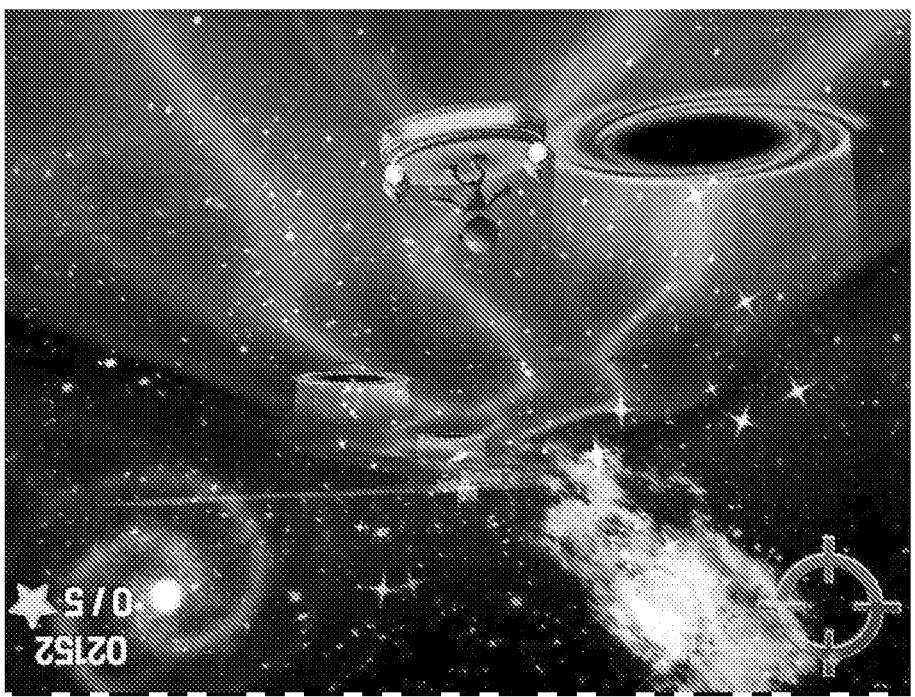
Figure 15V:
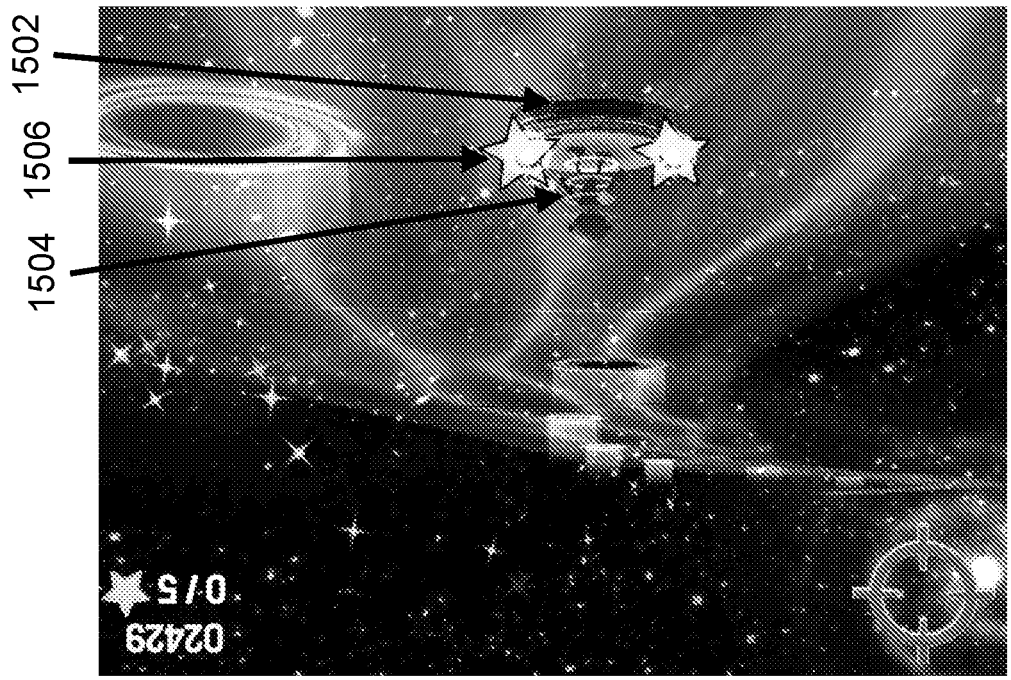
Figure 15U:
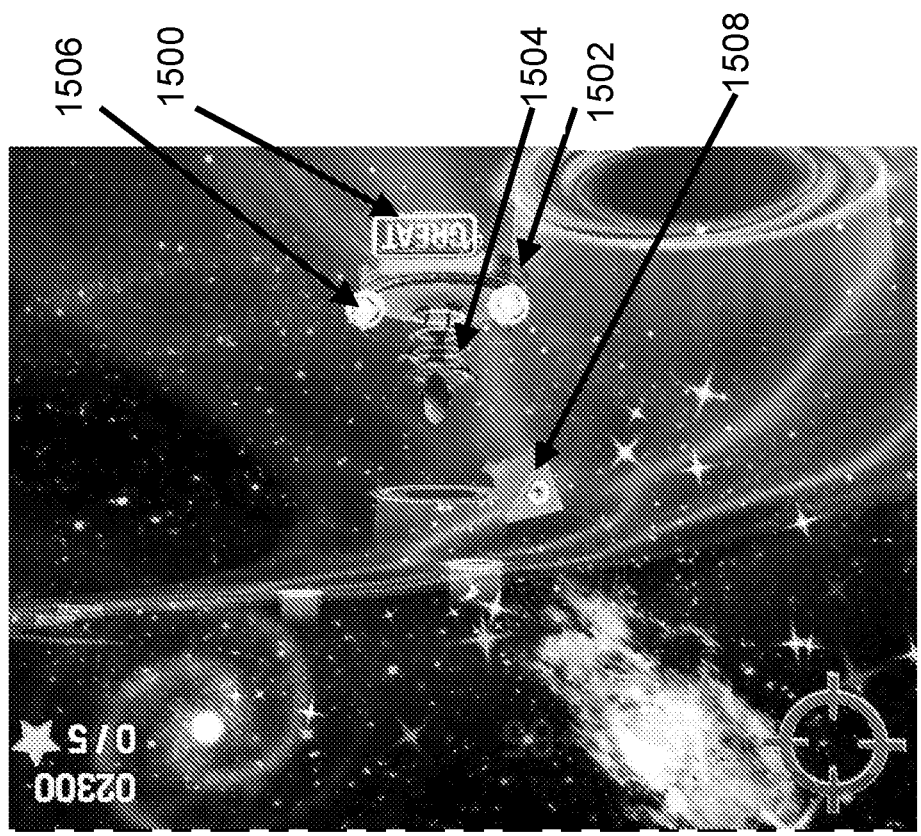

FIGS. 15A-15V show other examples of the dynamics of multi-tasking involving user interaction with an implementation of a navigation task, and with an interference. In this example, the task is a visuo-motor navigation task, and the interference is target discrimination (as a secondary task). The individual is instructed to perform the navigation task by controlling the motion of the avatar 1502 along a path that coincides with the milestone objects 1504. FIGS. 15A-15V show a non-limiting example implementation where the individual is expected to actuate an apparatus or computing device (or other sensing device) to cause the avatar 1502 to coincide with the milestone object 1504 as the response in the navigation task, with scoring based on the success of the individual at hitting or otherwise crossing paths with the milestone objects 1504. In another example, the individual is expected to actuate an apparatus or computing device (or other sensing device) to cause the avatar 1502 to miss (i.e., not cross paths) with the milestone object 1504, with scoring based on the success of the individual at avoiding the milestone objects 1504. FIGS. 15A-15V also show the dynamics of a target object 1506, where the time-varying characteristic is the trajectory of motion of the target object 1506. FIGS. 15A-15V also show the dynamics of a non-target object 1508, where the time-varying characteristic is the trajectory of motion of the non-target object 1508.

FIGS. 15K-15V show non-limiting examples of the types of rewards that may be rendered to an individual to signal a degree of success in interacting with the tasks and/or interference. In FIGS. 15K-15R, a feature 1510 including the word "GOOD" is rendered near the avatar 1502 to signal to the individual that analysis of the data indicative of the individual's responses to the navigation task and target discrimination interference indicate satisfactory performance. FIG. 15V shows an example of a change in the type of rewards presented to the individual as another indication of satisfactory performance, including a change in the rendering of feature 1500 to display the word "GREAT", at least one modification to the avatar 1502 to symbolize excitement, such as but not limited to the rings 1504 or other active element and/or showing jet booster elements 1506 that become star-shaped. Many other types of reward elements can be used, and the rate and type of reward elements displayed can be changed and modulated as a time-varying element.

As described hereinabove, the example systems, methods, and apparatus herein are configured to apply a computational model of human decision-making to the received response data received, based on the time-varying characteristics of the task and/or interference. The time-varying characteristics of the task and/or interference result in non-linear accumulation of belief for an individual's decision making. Accordingly, based on the response data from the individual's interaction with the task and/or interference, the processing unit can be configured to compute at least one response profile representative of the performance of the individual and determines a decision boundary metric (such as but not limited to the response criterion) from the response profile. As also described hereinabove, the response classifier can be executed based on the computed values of decision boundary metric (such as but not limited to the response criterion), to generate a classifier output indicative of the cognitive response capabilities of the individual.

In various examples, the degree of non-linearity of the accumulation of belief for an individual's decision making (i.e., as to whether to execute a response) can be modulated based on adjusting the time-varying characteristics of the task and/or interference. As a non-limiting example, where the time-varying characteristic is a trajectory, speed, orientation, or size of the object (target or non-target), the amount of information available to an individual to develop a belief (in order to make decision as to whether to execute a response) can be made smaller initially, e.g., where the object caused to be more difficult to discriminate by being rendered as farther away or smaller, and can be made to increase at differing rates (nonlinearly) depending on how quickly more information is made available to the individual to develop belief (e.g., as the object is rendered to appear to get larger, change orientation, move slower, or move closer in the environment). Other non-limiting example time-varying characteristics of the task and/or interference that can be adjusted to modulate the degree of non-linearity of the accumulation of belief include one or more of a rate of change of a facial expression, at least one color of an object, the type of the object, a rate of morphing of a first type of object to change to a second type of object, and a proportionate amount of a first type of object and a second type of object that form a blendshape (e.g., where the second type of object is the target and the first type of object is a non-target).

As also described hereinabove, the programmed processing unit can be configured to execute processor-executable instructions to adapt the task and/or the interference to derive a modification in the computed response profile. Given that the response profile is computed based on the individual's response data (e.g., data based on a first response to the task and/or data based on a second response to the interference), a change in the computed response profile can be used as an indication of a change in the responses and performance measures of the individual. This in turn can provide an indication of a modification of the cognitive response capabilities of the individual.

As described hereinabove, adapting the tasks and/or interference based on the output from the response classifiers can provide for greater flexibility than adaptation based on the percent correct or D-Prime (d') signal detection metric of sensitivity to a target. That is, the interaction is adapted by modifying parameters of the tasks and/or interference to be rendered to the user interface in a subsequent trial or session of the individual's interaction based on the computed decision boundary metric (such as but not limited to the response criterion) and/or the output from a trained response classifier using response data from a previous trial or session. For example, if the decision boundary metric (such as but not limited to the response criterion) indicates a tendency of the individual to provide a first type of response of the two or more differing types of responses (Response A vs. Response B) to the task or the interference, the difficulty levels of the tasks and/or interference rendered at the user interface for user interaction for a subsequent level can be modified. The methodology for adapting the difficulty levels of the task and/or interference of a subsequent session based on the decision boundary metric (such as but not limited to the response criterion) computed for the individual's performance from a previous session can be optimized to modify an individual's first decision boundary metric (such as but not limited to the response criterion) (and first performance) indicative of first type of response strategy towards a second decision boundary metric (such as but not limited to the response criterion) (and second performance) indicative of a second type of response strategy.

As a non-limiting example, the difficulty level of a subsequent session of an implementation of an example system, method, and apparatus herein can be adapted to modify an individual's first decision boundary metric (such as but not limited to the response criterion) (and first performance) indicative of a more impulsive response strategy to a second decision boundary metric (such as but not limited to the response criterion) (and second performance) indicative of a more conservative response strategy, thereby seeking to promote less impulsive behavior in the individual.

In a non-limiting example, the adaptation of the difficulty of a task and/or interference may be adapted with each different stimulus that is presented.

In another non-limiting example, the example system, method, and apparatus herein can be configured to adapt a difficulty level of a task and/or interference one or more times in fixed time intervals or in other set schedule, such as but not limited to each second, in 10 second intervals, every 30 seconds, or on frequencies of once per second, 2 times per second, or more (such as but not limited to 30 times per second).

In an example, the difficulty level of a task or interference can be adapted by changing the time-varying characteristics, such as but not limited to a speed of an object, a rate of change of a facial expression, a direction of trajectory of an object, a change of orientation of an object, at least one color of an object, a type of an object, or a size of an object, or changing a sequence or balance of presentation of a target stimulus versus a non-target stimulus.

In a non-limiting example of a visuo-motor task (a type of navigation task), one or more of navigation speed, shape of the course (changing frequency of turns, changing turning radius), and number or size of obstacles can be changed to modify the difficulty of a navigation game level, with the difficulty level increasing with increasing speed and/or increasing numbers and/or sizes of obstacles (milestone objects).

In a non-limiting example, the difficulty level of a task and/or interference of a subsequent level can also be changed in real-time as feedback, e.g., the difficulty of a subsequent level can be increased or decreased in relation to the data indicative of the performance of the task.

Figure 16A:
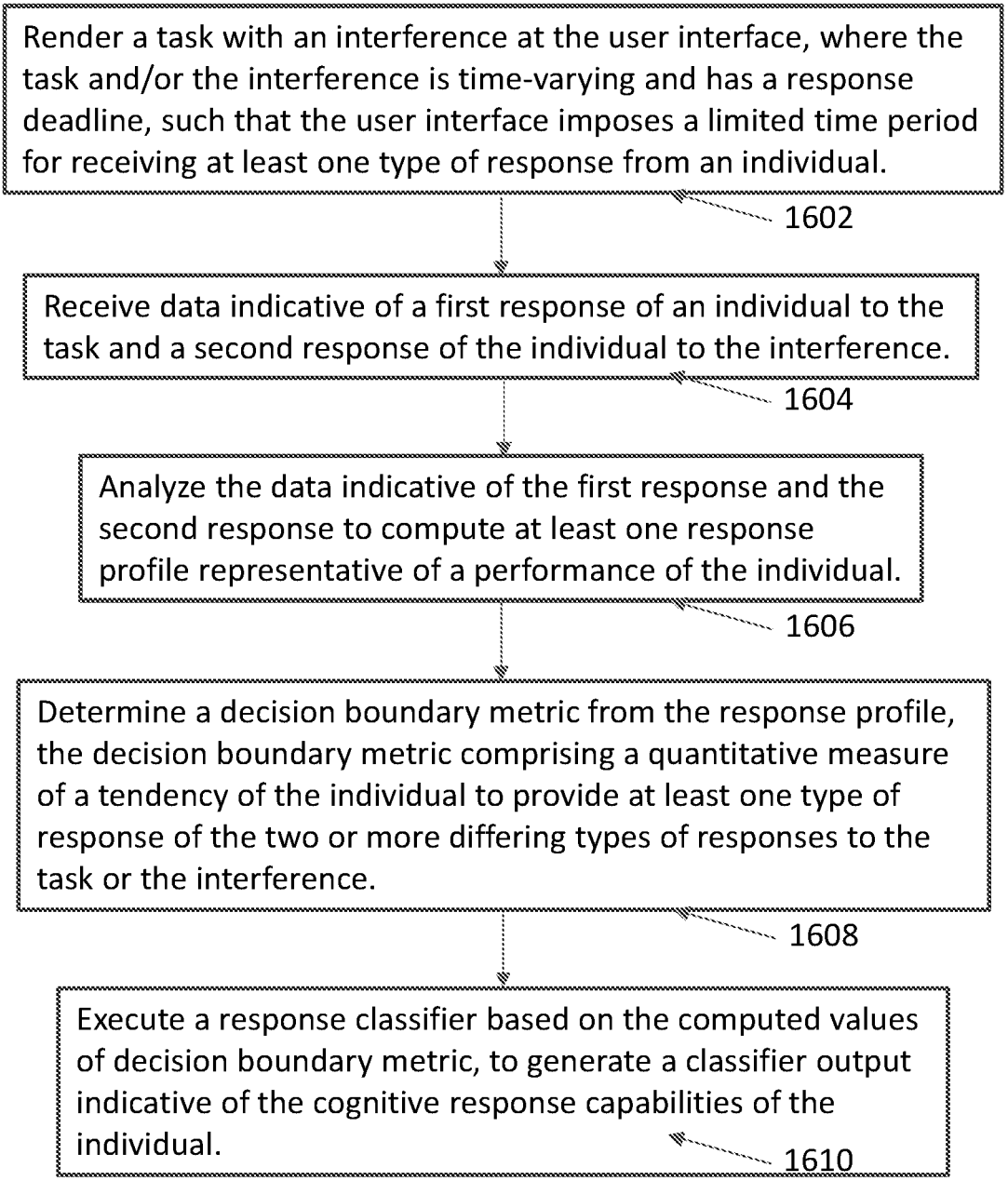
FIGS. 16A-16C show flowcharts of example methods, according to the principles herein.
Figure 16B:
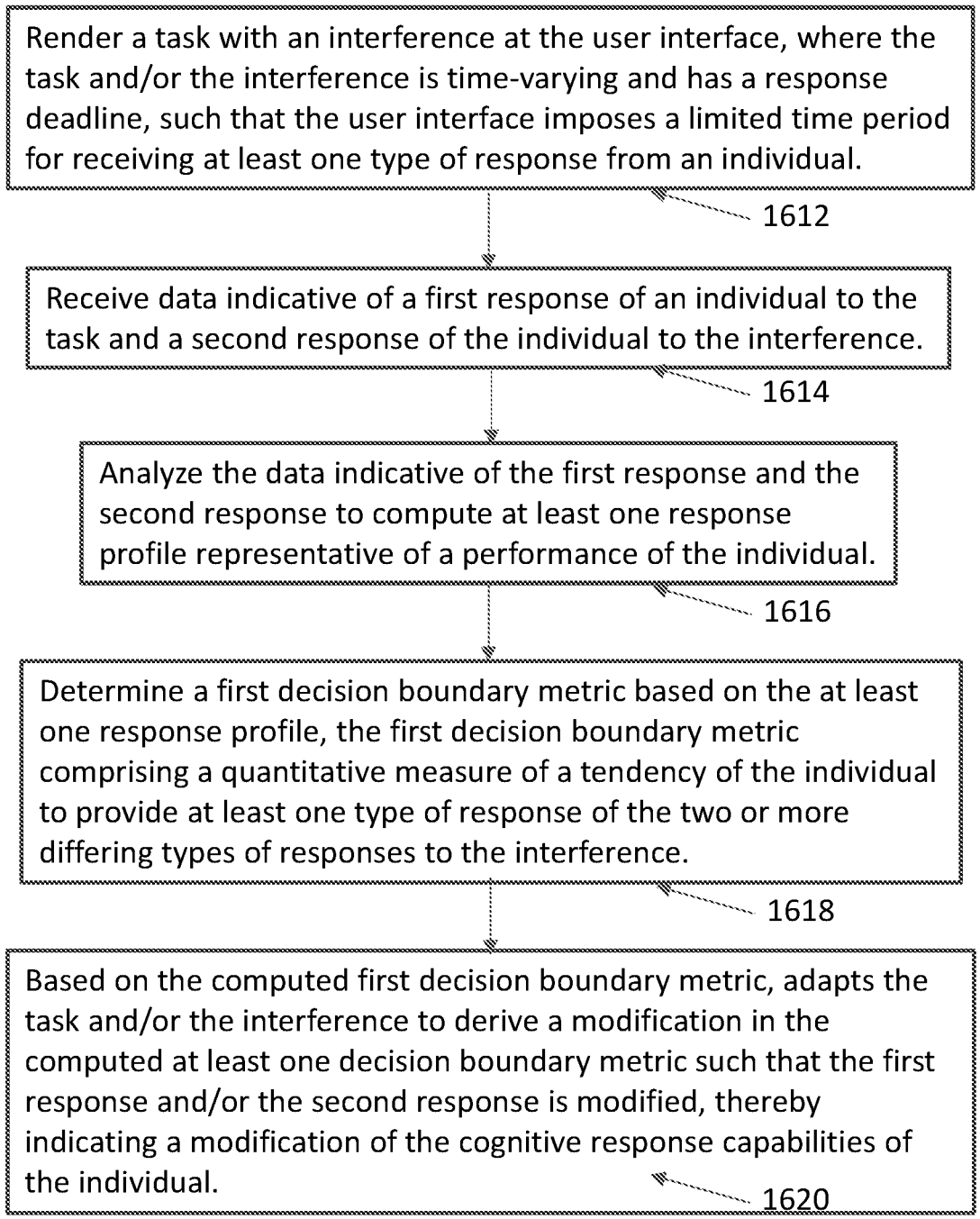
Figure 16C:
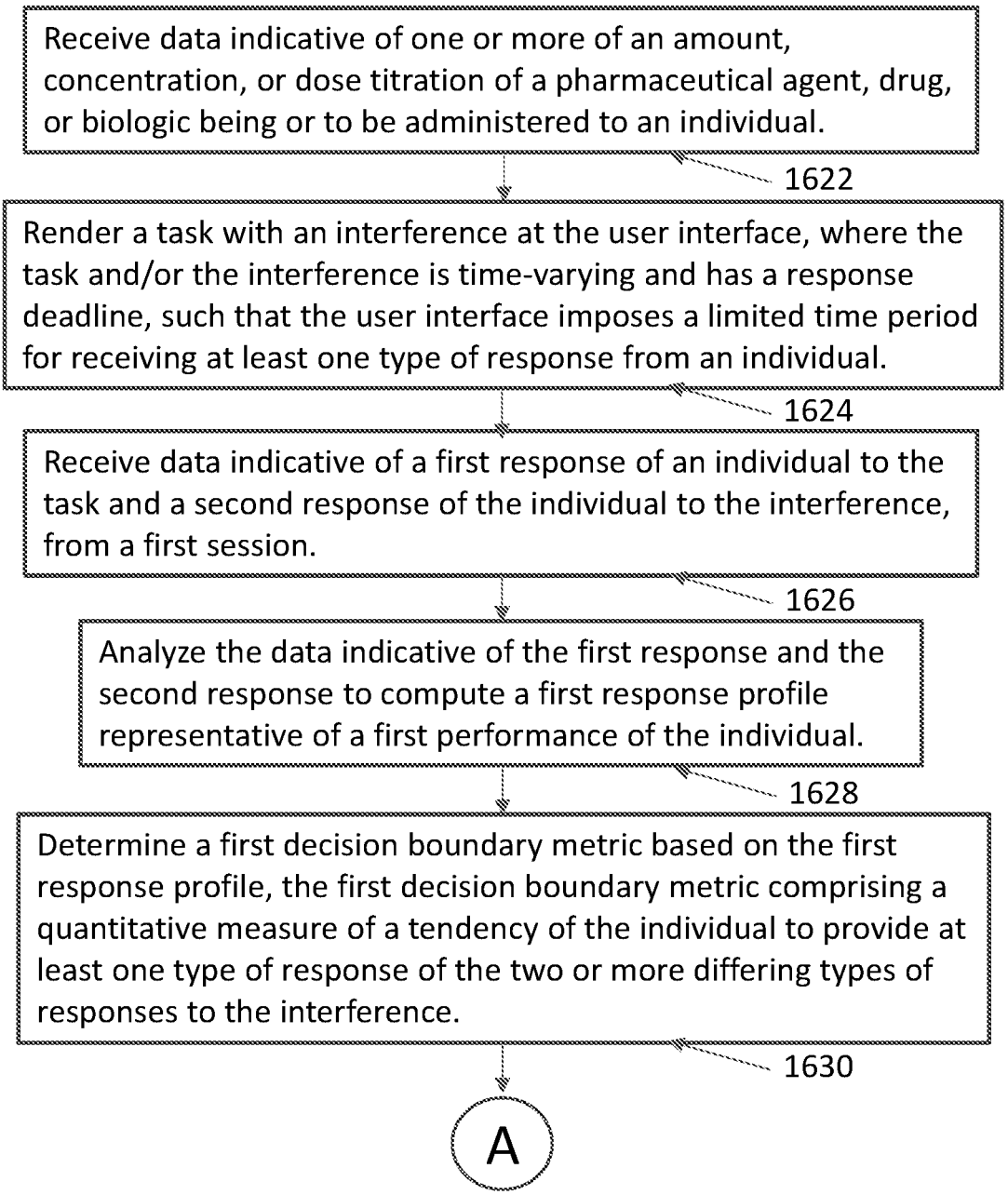
Figure 16C:
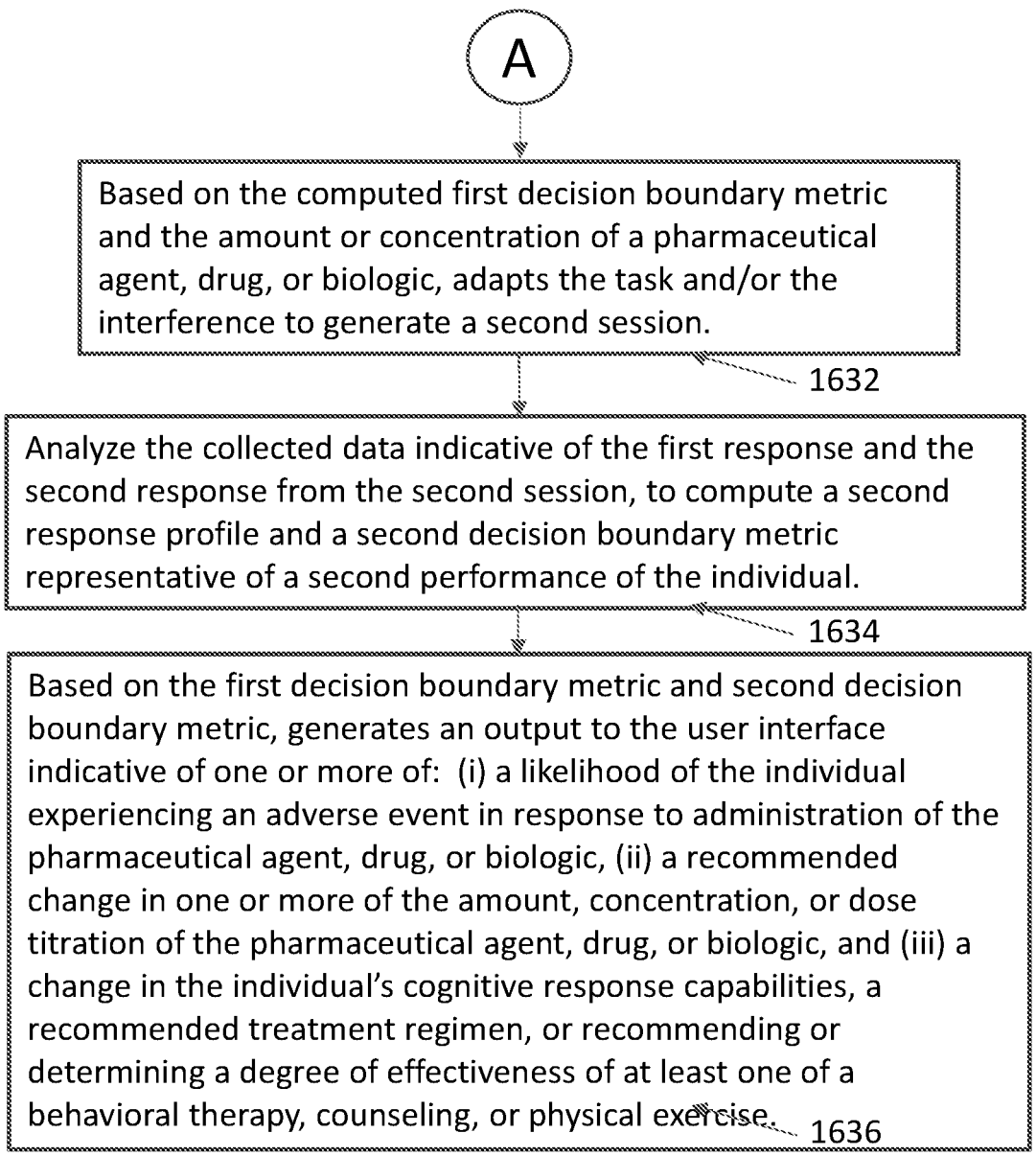

FIG. 16A-16C show flowcharts of example methods, according to the principles herein. In any example, the method is executed based on execution of processor-executable instructions using a programmed processing unit.

FIG. 16A shows a method for generating a quantifier of cognitive skills in an individual using a machine learning response classifier, using a programmed processing unit. In block 1602, a task with an interference is rendered at a user interface, where the task and/or the interference is time-varying and has a response deadline, such that the user interface imposes a limited time period for receiving at least one type of response from an individual. In block 1604, data indicative of a first response of an individual to the task and a second response of the individual to the interference is received. In block 1606, the data indicative of the first response and the second response are analyzed to compute at least one response profile representative of a performance of the individual. In block 1608, a decision boundary metric is determined from the response profile, where the decision boundary metric includes a quantitative measure of a tendency of the individual to provide at least one type of response of the two or more differing types of responses to the task or the interference. In block 1610, a response classifier is executed based on the computed values of decision boundary metric, to generate a classifier output indicative of the cognitive response capabilities of the individual.

FIG. 16B shows a method for enhancing cognitive skills in an individual, using a programmed processing unit. In block 1612, a task with an interference is rendered at a user interface, where the task and/or the interference is time-varying and has a response deadline, such that the user interface imposes a limited time period for receiving at least one type of response from an individual. In block 1614, data indicative of a first response of an individual to the task and a second response of the individual to the interference is received. In block 1616, the data indicative of the first response and the second response are analyzed to compute at least one response profile representative of a performance of the individual. In block 1618, a decision boundary metric is determined from the response profile, where the decision boundary metric includes a quantitative measure of a tendency of the individual to provide at least one type of response of the two or more differing types of responses to the task or the interference. In block 1620, based on the computed first decision boundary metric, the task and/or the interference is adapted to derive a modification in the computed at least one decision boundary metric (such as but not limited to the response criterion) such that the first response and/or the second response is modified, thereby indicating a modification of the cognitive response capabilities of the individual.

Figure 17:
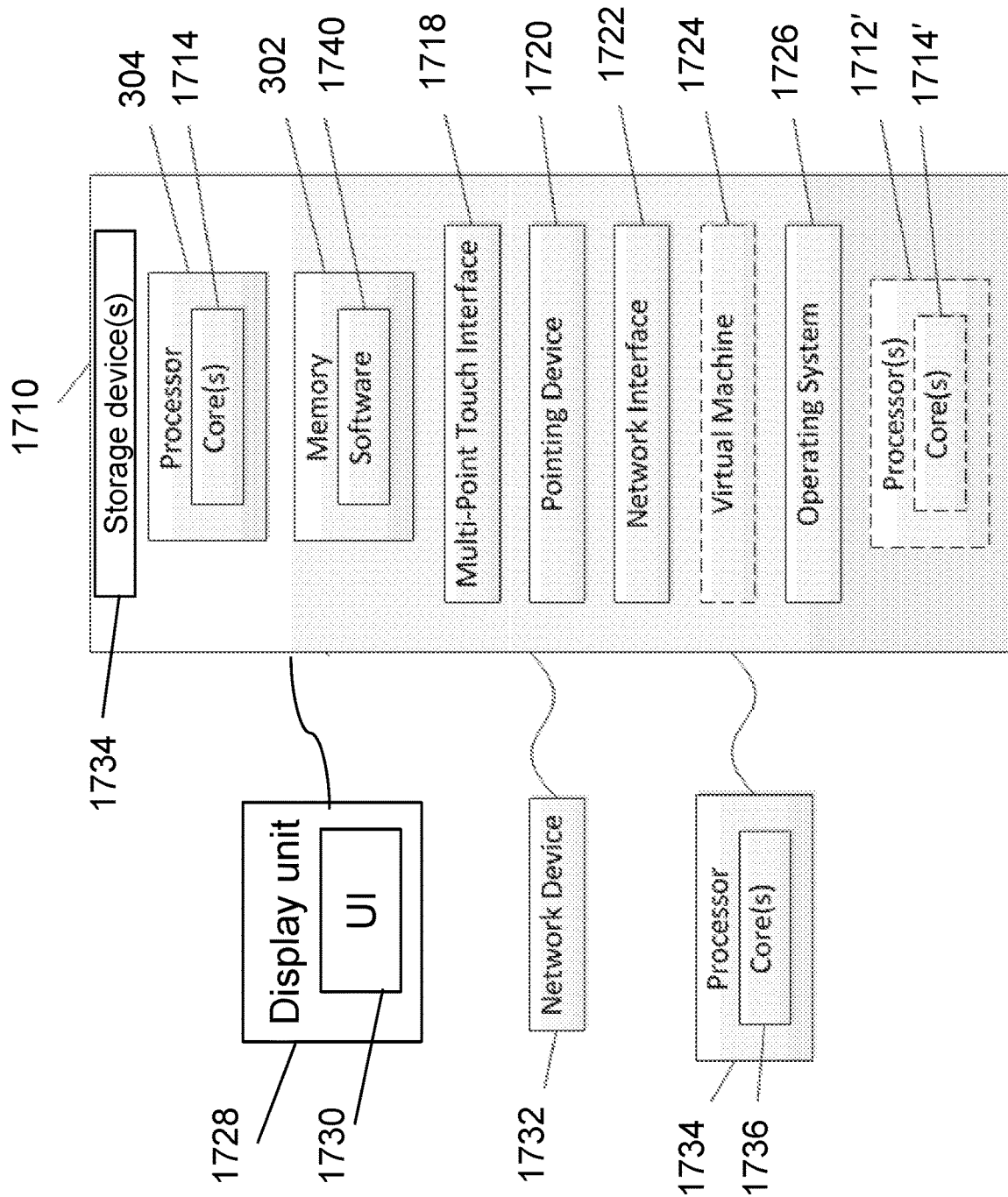
FIG. 17 shows the architecture of an example computer system, according to the principles herein.

FIG. 16C shows a method for enhancing cognitive skills in an individual, using a programmed processing unit. In block 1622, data indicative of one or more of an amount, concentration, or dose titration of a pharmaceutical agent, drug, or biologic being or to be administered to an individual is received. In block 1624, a task with an interference is rendered at a user interface, where the task and/or the interference is time-varying and has a response deadline, such that the user interface imposes a limited time period for receiving at least one type of response from an individual. In block 1626, data indicative of a first response of an individual to the task and a second response of the individual to the interference, from a first session, is received. In block 1628, the data indicative of the first response and the second response is analyzed to compute a first response profile representative of a first performance of the individual. In block 1630, a first decision boundary metric is determined based on the first response profile, where the first decision boundary metric includes a quantitative measure of a tendency of the individual to provide at least one type of response of the two or more differing types of responses to the interference. In block 1632, based on the computed first decision boundary metric and the amount or concentration of a pharmaceutical agent, drug, or biologic, the task and/or the interference is adapted to generate a second session. In block 1634, the collected data indicative of the first response and the second response from the second session is analyzed to compute a second response profile and a second decision boundary metric representative of a second performance of the individual. In block 1636, based on the first decision boundary metric and second decision boundary metric, an output is generated to the user interface indicative of one or more of: (i) a likelihood of the individual experiencing an adverse event in response to administration of the pharmaceutical agent, drug, or biologic, (ii) a recommended change in one or more of the amount, concentration, or dose titration of the pharmaceutical agent, drug, or biologic, and (iii) a change in the individual's cognitive response capabilities, a recommended treatment regimen, or recommending or determining a degree of effectiveness of at least one of a behavioral therapy, counseling, or physical exercise FIG. 17 is a block diagram of an example computing device 1710 that can be used as a computing component according to the principles herein. In any example herein, computing device 1710 can be configured as a console that receives user input to implement the computing component, including to apply the signal detection metrics in computer-implemented adaptive response-deadline procedures. For clarity, FIG. 17 also refers back to and provides greater detail regarding various elements of the example system of FIG. 1 and the example computing device of FIG. 2. The computing device 1710 can include one or more non-transitory computer-readable media for storing one or more computer-executable instructions or software for implementing examples. The non-transitory computer-readable media can include, but are not limited to, one or more types of hardware memory, non-transitory tangible media (for example, one or more magnetic storage disks, one or more optical disks, one or more flash drives), and the like. For example, memory 302 included in the computing device 1710 can store computer-readable and computer-executable instructions or software for performing the operations disclosed herein. For example, the memory 302 can store a software application 1740 which is configured to perform various of the disclosed operations (e.g., analyze cognitive platform measurement data and response data, apply a signal detection metrics in adaptive response-deadline procedures, or performing a computation). The computing device 1710 also includes configurable and/or programmable processor 304 and an associated core 1714, and optionally, one or more additional configurable and/or programmable processing devices, e.g., processor(s) 1712' and associated core(s) 1714' (for example, in the case of computational devices having multiple processors/cores), for executing computer-readable and computer-executable instructions or software stored in the memory 302 and other programs for controlling system hardware. Processor 304 and processor(s) 1712' can each be a single core processor or multiple core (1714 and 1714') processor.

Virtualization can be employed in the computing device 1710 so that infrastructure and resources in the console can be shared dynamically. A virtual machine 1724 can be provided to handle a process running on multiple processors so that the process appears to be using only one computing resource rather than multiple computing resources. Multiple virtual machines can also be used with one processor.

Memory 302 can include a computational device memory or random access memory, such as DRAM, SRAM, EDO RAM, and the like. Memory 302 can include other types of memory as well, or combinations thereof.

A user can interact with the computing device 1710 through a visual display unit 1728, such as a computer monitor, which can display one or more user interfaces (UI) 1730 that can be provided in accordance with example systems and methods. The computing device 1710 can include other I/O devices for receiving input from a user, for example, a keyboard or any suitable multi-point touch interface 1718, a pointing device 1720 (e.g., a mouse). The keyboard 1718 and the pointing device 1720 can be coupled to the visual display unit 1728. The computing device 1710 can include other suitable conventional I/O peripherals.

The computing device 1710 can also include one or more storage devices 1734, such as a hard-drive, CD-ROM, or other computer readable media, for storing data and computer-readable instructions and/or software that perform operations disclosed herein. Example storage device 1734 can also store one or more databases for storing any suitable information required to implement example systems and methods. The databases can be updated manually or automatically at any suitable time to add, delete, and/or update one or more items in the databases.

The computing device 1710 can include a network interface 1722 configured to interface via one or more network devices 1732 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 1722 can include a built-in network adapter, network interface card, PCMCIA network card, card bus network adapter, wireless network adapter, USB network adapter, modem or any other device suitable for interfacing the computing device 1710 to any type of network capable of communication and performing the operations described herein. Moreover, the computing device 1710 can be any computational device, such as a workstation, desktop computer, server, laptop, handheld computer, tablet computer, or other form of computing or telecommunications device that is capable of communication and that has sufficient processor power and memory capacity to perform the operations described herein.

The computing device 1710 can run any operating system 1726, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, or any other operating system capable of running on the console and performing the operations described herein. In some examples, the operating system 1726 can be run in native mode or emulated mode. In an example, the operating system 1726 can be run on one or more cloud machine instances.

Examples of the systems, methods and operations described herein can be implemented in digital electronic circuitry, or in computer software, firmware, or hardware, including the structures disclosed in this specification and their structural equivalents, or in combinations of one or more thereof. Examples of the systems, methods and operations described herein can be implemented as one or more computer programs, i.e., one or more modules of computer program instructions, encoded on computer storage medium for execution by, or to control the operation of, data processing apparatus. The program instructions can be encoded on an artificially generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" or "computing device" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them.

A computer program (also known as a program, software, software application, script, application or code) can be written in any form of programming language, including compiled or interpreted languages, declarative or procedural languages, and it can be deployed in any form, including as a stand alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing on one or more computer programs to perform actions by operating on input data and generating output. The processes and logic flows can also be performed by, and apparatuses can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), for example. Devices suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto-optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, for displaying information to the user and a keyboard and a pointing device, e.g., a mouse, a stylus, touch screen or a trackball, by which the user can provide input to the computer. Other kinds of devices can be used to provide for interaction with a user as well. For example, feedback (i.e., output) provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

In some examples, a system, method or operation herein can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

Example computing system 400 can include clients and servers. A client and server are generally remote from each other and typically interact through a communication network. The relationship of client and server arises by virtue of computer programs running on the respective computers and having a client-server relationship to each other. In some embodiments, a server transmits data to a client device (e.g., for purposes of displaying data to and receiving user input from a user interacting with the client device). Data generated at the client device (e.g., a result of the user interaction) can be received from the client device at the server.

CONCLUSION

While this specification contains many specific implementation details, these should not be construed as limitations on the scope of any inventions or of what may be claimed, but rather as descriptions of features specific to particular embodiments of the systems and methods described herein. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In some cases, the actions recited in the claims can be performed in a different order and still achieve desirable results. In addition, the processes depicted in the accompanying figures do not necessarily require the particular order shown, or sequential order, to achieve desirable results.

In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products The above-described embodiments can be implemented in any of numerous ways. For example, some embodiments may be implemented using hardware, software or a combination thereof. When any aspect of an embodiment is implemented at least in part in software, the software code can be executed on any suitable processor or collection of processors, whether provided in a single computer or distributed among multiple computers.

The above-described embodiments can be implemented in any of numerous ways. For example, some embodiments may be implemented using hardware, software or a combination thereof. When any aspect of an embodiment is implemented at least in part in software, the software code can be executed on any suitable processor or collection of processors, whether provided in a single computer or distributed among multiple computers.

In this respect, various aspects of the invention may be embodied at least in part as a computer readable storage medium (or multiple computer readable storage media) (e.g., a computer memory, compact disks, optical disks, magnetic tapes, flash memories, circuit configurations in Field Programmable Gate Arrays or other semiconductor devices, or other tangible computer storage medium or non-transitory medium) encoded with one or more programs that, when executed on one or more computers or other processors, perform methods that implement the various embodiments of the technology discussed above. The computer readable medium or media can be transportable, such that the program or programs stored thereon can be loaded onto one or more different computers or other processors to implement various aspects of the present technology as discussed above.

The terms "program" or "software" are used herein in a generic sense to refer to any type of computer code or set of computer-executable instructions that can be employed to program a computer or other processor to implement various aspects of the present technology as discussed above. Additionally, it should be appreciated that according to one aspect of this embodiment, one or more computer programs that when executed perform methods of the present technology need not reside on a single computer or processor, but may be distributed in a modular fashion amongst a number of different computers or processors to implement various aspects of the present technology.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, the technology described herein may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An apparatus for generating a quantifier of cognitive skills in an individual using a response classifier, said apparatus comprising:
    a user interface;
    a memory to store processor-executable instructions; and
    a processing unit communicatively coupled to the user interface and the memory, wherein upon execution of the processor-executable instructions by the processing unit, the processing unit is configured to:
    render a task with an interference at the user interface, one or more of the task and the interference being time-varying and having a response deadline, such that the user interface imposes a limited time period for receiving at least one type of response from an individual, wherein the user interface is configured to measure data indicative of two or more differing types of responses to the task or to the interference;
    receive data indicative of a first response of an individual to the task and a second response of the individual to the interference at the user interface;
    analyze the data indicative of the first response and the second response to compute at least one response profile representative of a performance of the individual;
    determine a decision boundary metric from the at least one response profile, the decision boundary metric comprising a quantitative measure of a tendency of the individual to provide at least one of an impulsive response to the task with the interference and a conservative response to the task with the interference;
    execute the response classifier based at least in part on the computed values of the decision boundary metric to generate a classifier output indicative of the cognitive response capabilities of the individual; and
    apply at least one adaptive procedure to modify the task and/or the interference at the user interface, such that analysis of the data indicative of the first response and/or the second response indicates a modification of the at least one response profile,
    wherein the at least one adaptive procedure is configured to modify a time-varying characteristic of the task and/or the interference at the user interface,
    wherein the at least one adaptive procedure modifies the response deadline to modify a performance characteristic of the individual to an impulsive response profile or a conservative response profile, such that measurements at different response deadlines provide different data as to a first decision boundary or a second decision boundary of the decision boundary metric,
    wherein modifying the time-varying characteristic of the task and/or the interference at the user interface is configured to modify the first decision boundary or the second decision boundary of the decision boundary metric,
    wherein the impulsive response profile represents an impulsive response strategy of the individual to the task or the interference, and the conservative response profile represents a conservative response strategy of the individual to the task or the interference.

2. The apparatus of claim 1, further comprising at least one actuating component, wherein the processing unit further controls the actuating component to effect one or more of an auditory stimulus, a tactile stimulus, and a vibrational stimulus, and wherein the task and/or the interference comprises one or more of the auditory stimulus, the tactile stimulus, and the vibrational stimulus.

3. The apparatus of claim 1, wherein the processing unit is further configured to compute as the classifier output parameters indicative of one or more of a bias sensitivity derived from the data indicative of the first response and the second response, a non-decision time sensitivity to parallel tasks, a belief accumulation sensitivity to parallel task demands, a reward rate sensitivity, or a response window estimation efficiency.

4. The apparatus of claim 1, wherein the processing unit is configured to control the user interface to render the task as a continuous visuo-motor tracking task.

5. The apparatus of claim 1, wherein the processing unit is configured to control the user interface to render the interference as a target discrimination interference.

6. The apparatus of claim 1, wherein the processing unit is configured to render the task with the interference by configuring the user interface to:
render the task in the presence of the interference such that the interference diverts the individual's attention from the task, in which the interference is selected from a group consisting of a distraction and an interrupter.

7. The apparatus of claim 1, wherein the response classifier is trained using a plurality of training datasets, each training dataset corresponding to a previously classified individual of a plurality of individuals, and each training dataset comprising data indicative of a first response of the classified individual to the task, data indicative of a second response of the classified individual to the interference, and one or more of (i) data indicative of a performance of the classified individual at one or more of a cognitive test or a behavioral test, and (ii) data indicative of a diagnosis of a status or progression of a cognitive condition, a disease or an executive function disorder of the classified individual.

8. The apparatus of claim 1, wherein the classifier output comprises an indication of a degree of impulsiveness or conservativeness of the individual's cognitive response capabilities.

9. The apparatus of claim 1, wherein the processing unit is configured to transmit the classifier output to the individual and/or display the classifier output on the user interface.

10. The apparatus of claim 1, wherein the classifier output comprises a measure of attention deficit or impulsivity of the individual.

11. The apparatus of claim 1, wherein the processing unit is further configured to use the classifier output for cognitive monitoring of one or more of a cognitive condition, a disease, or an executive function disorder.

12. The apparatus of claim 1, wherein the apparatus comprises one or more sensor components, and wherein the processing unit is configured to control the one or more sensor components to receive the data indicative of the first response and the second response.

13. The apparatus of claim 1, wherein the processing unit is further configured to use the classifier output for one or more of (i) changing one or more of a recommended amount, concentration, or dose titration of a pharmaceutical agent, drug, or biologic, (ii) identifying a likelihood of the individual experiencing an adverse event in response to administration of the pharmaceutical agent, drug, or biologic, (iii) identifying a change in the individual's cognitive response capabilities, (iv) recommending a treatment regimen, (v) recommending at least one of a behavioral therapy, counseling, or physical exercise, or (vi) determining a degree of effectiveness of at least one of a behavioral therapy, counseling, or physical exercise.

14. A computer-implemented method for generating a quantifier of cognitive skills in an individual using a response classifier, said method comprising:
rendering, using at least one processing unit, a task with an interference at a user interface;
measuring data indicative of two or more differing types of responses to the task or to the interference at the user interface;
receiving, via the user interface, data indicative of a first response of an individual to the task and a second response of the individual to the interference;
analyzing, using the at least one processing unit, the data indicative of the first response and the second response to compute at least one response profile representative of a performance of the individual;
determining, using the at least one processing unit, a decision boundary metric from the response profile, the decision boundary metric comprising a quantitative measure of a tendency of the individual to provide at least one of an impulsive response to the task with the interference and a conservative response to the task with the interference;
executing the response classifier based at least in part on the decision boundary metric, to generate a classifier output indicative of the individual's cognitive response capabilities; and
applying, with the at least one processing unit, at least one adaptive procedure to modify the task and/or the interference at the user interface, such that analysis of the data indicative of the first response and/or the second response indicates a modification of the at least one response profile,
wherein the at least one adaptive procedure is configured to modify a time-varying characteristic of the task and/or interference at the user interface,
wherein the at least one adaptive procedure modifies the response deadline to modify a performance characteristic of the individual to an impulsive response profile or a conservative response profile, such that measurements at different response deadlines provide different data as to a first decision boundary or a second decision boundary of the decision boundary metric,
wherein modifying the time-varying characteristic of the task and/or the interference at the user interface is configured to modify the first decision boundary or the second decision boundary of the decision boundary metric,
wherein the impulsive response profile represents an impulsive response strategy of the individual to the task or the interference, and the conservative response profile represents a conservative response strategy of the individual to the task or the interference.

15. The method of claim 14, wherein the at least one processing unit is further configured to control at least one actuating component to effect one or more of an auditory stimulus, a tactile stimulus, and a vibrational stimulus, and wherein the task and/or the interference comprises one or more of the auditory stimulus, the tactile stimulus, and the vibrational stimulus.

16. The method of claim 14, wherein the at least one processing unit is further configured to compute as the classifier output parameters indicative of one or more of a bias sensitivity derived from the data indicative of the first response and the second response, a non-decision time sensitivity to parallel tasks, a belief accumulation sensitivity to parallel task demands, a reward rate sensitivity, or a response window estimation efficiency.

17. The method of claim 14, wherein the at least one processing unit is configured to control the user interface to render the task as a continuous visuo-motor tracking task.

18. The method of claim 14, wherein the at least one processing unit is configured to control the user interface to render the interference as a target discrimination interference.

19. The method of claim 14, wherein rendering the task with the interference comprises:
rendering the task in the presence of the interference such that the interference diverts the individual's attention from the task, the interference selected from the group consisting of a distraction and an interrupter.

20. The method of claim 14, wherein the response classifier is trained using a plurality of training datasets, each training dataset corresponding to a previously classified individual of a plurality of individuals, and each training dataset comprising data indicative of the first response of the classified individual to the task, data indicative of the second response of the classified individual to the interference, and one or more of (i) data indicative of a performance of the classified individual at one or more of a cognitive test or a behavioral test, and (ii) data indicative of a diagnosis of a status or progression of a cognitive condition, a disease or an executive function disorder of the classified individual.

21. The method of claim 14, wherein the classifier output comprises an indication of a degree of impulsiveness or conservativeness of the individual's cognitive response capabilities.

22. The method of claim 14, wherein the classifier output is transmitted to the individual and/or displayed to the user interface.

23. The method of claim 14, wherein the classifier output comprises a measure of attention deficit or impulsivity of the individual.

24. The method of claim 14, further comprising using the classifier output for cognitive monitoring of one or more of a cognitive condition, a disease, or an executive function disorder.

25. The method of claim 14, wherein receiving the data indicative of the first response and the second response comprises using one or more sensor components to receive the data indicative of the first response and the second response.

26. The method of claim 14, further comprising using the classifier output for one or more of changing one or more of an amount, concentration, or dose titration of a pharmaceutical agent, drug, or biologic, identifying a likelihood of the individual experiencing an adverse event in response to administration of the pharmaceutical agent, drug, or biologic, identifying a change in the individual's cognitive response capabilities, recommending a treatment regimen, or recommending or determining a degree of effectiveness of at least one of a behavioral therapy, counseling, or physical exercise.

27. An apparatus for enhancing cognitive skills in an individual, said apparatus comprising:
a user interface;
a memory to store processor-executable instructions; and
a processing unit communicatively coupled to the user interface and the memory, wherein upon execution of the processor-executable instructions by the processing unit, the processing unit is configured to:
render a primary task with an interference at the user interface,
one or more of the primary task and the interference being time-varying and having a response deadline, such that the user interface imposes a limited time period for receiving at least one type of response from an individual; and
the user interface being configured to measure data indicative of two or more differing types of responses to the primary task or to the interference;
receive data indicative of a first response of an individual to the primary task and a second response of the individual to the interference at the user interface;
analyze the data indicative of the first response and the second response to compute at least one response profile representative of a performance of the individual;
determine a decision boundary metric based at least in part on the at least one response profile, the decision boundary metric comprising a quantitative measure of a tendency of the individual to provide at least one of an impulsive response to the task with the interference and a conservative response to the task with the interference;
based at least in part on the computed decision boundary metric, adapt the primary task and/or the interference to derive a modification in the computed decision boundary metric such that a further response to the primary task and/or a further response to the interference is modified at the user interface as compared to an earlier response to the primary task and/or an earlier response to the interference, thereby indicating a modification of the cognitive response capabilities of the individual; and
apply at least one adaptive procedure to modify the primary task and/or the interference at the user interface, such that analysis of the data indicative of the first response and/or the second response indicates a modification of the at least one response profile,
wherein the at least one adaptive procedure is configured to modify a time-varying characteristic of the task and/or interference at the user interface,
wherein the at least one adaptive procedure modifies the response deadline to modify a performance characteristic of the individual to an impulsive response profile or a conservative response profile, such that measurements at different response deadlines provide different data as to a first decision boundary or a second decision boundary of the decision boundary metric,
wherein modifying the time-varying characteristic of the task and/or the interference at the user interface is configured to modify the first decision boundary or the second decision boundary of the decision boundary metric,
wherein the impulsive response profile represents an impulsive response strategy of the individual to the task or the interference, and the conservative response profile represents a conservative response strategy of the individual to the task or the interference.

28. The apparatus of claim 27, wherein the indication of the modification of the cognitive response capabilities comprises a change in a measure of a degree of impulsiveness or conservativeness of the individual's cognitive response capabilities.

29. The apparatus of claim 27, wherein the indication of the modification of the cognitive response capabilities comprises a change in a measure of one or more of sustained attention, selective attention, attention deficit, impulsivity, inhibition, perceptive abilities, reaction and other motor functions, visual acuity, long-term memory, working memory, short-term memory, logic, and decision-making.

30. The apparatus of claim 27, wherein adapting the primary task and/or the interference based at least in part on the decision boundary metric comprises one or more of modifying a temporal length of a response window, modifying a type of reward or rate of presentation of rewards to the individual, and modifying a time-varying characteristic of the primary task and/or the interference.

31. The apparatus of claim 27, wherein the processing unit is configured to render the primary task with the interference by configuring the user interface to:
 render the primary task in the presence of the interference such that the interference diverts the individual's attention from the primary task and is selected from the group consisting of a distraction and an interrupter.

32. A computer-implemented method for enhancing cognitive skills in an individual, said method comprising:
 rendering a task with an interference at a user interface;
 measuring data indicative of two or more differing types of responses to the task or to the interference;
 receiving, via the user interface, data indicative of a first response of the individual to the task and a second response of the individual to the interference;
 analyzing, using at least one processing unit, the data indicative of the first response and the second response to compute at least one response profile representative of a performance of the individual;
 determining a decision boundary metric based at least in part on the at least one response profile, the decision boundary metric comprising a quantitative measure of a tendency of the individual to provide at least one of an impulsive response to the task with the interference and a conservative response to the task with the interference;
 based at least in part on the determined decision boundary metric, adapting the task and/or the interference to derive a modification in the determined decision boundary metric such that the first response and/or the second response is modified, thereby indicating a modification of the cognitive response capabilities of the individual; and
 applying at least one adaptive procedure to modify the task and/or the interference at the user interface, such that analysis of the data indicative of the first response and/or the second response indicates a modification of the at least one response profile,
 wherein the at least one adaptive procedure is configured to modify a time-varying characteristic of the task and/or the interference at the user interface,
 wherein the at least one adaptive procedure modifies the response deadline to modify a performance characteristic of the individual to an impulsive response profile or a conservative response profile, such that measurements at different response deadlines provide different data as to a first decision boundary or a second decision boundary of the decision boundary metric,
 wherein modifying the time-varying characteristic of the task and/or the interference at the user interface is configured to modify the first decision boundary or the second decision boundary of the decision boundary metric,
 wherein the impulsive response profile represents an impulsive response strategy of the individual to the task or the interference, and the conservative response profile represents a conservative response strategy of the individual to the task or the interference.

* * * * *